US008962657B2

(12) United States Patent
Heffernan et al.

(10) Patent No.: US 8,962,657 B2
(45) Date of Patent: Feb. 24, 2015

(54) ARYL DERIVATIVES AND USES THEREOF

(71) Applicant: Jacobus Pharmaceutical Company, Inc., Princeton, NJ (US)

(72) Inventors: Gavin David Heffernan, Florence, NJ (US); David Penman Jacobus, Princeton, NJ (US); Guy Alan Schiehser, Washington Crossing, PA (US); Hong-Ming Shieh, Newtown, PA (US); Wenyi Zhao, Monroe Township, NJ (US)

(73) Assignee: Jacobus Pharmaceutical Company, Inc., Princeton, NJ (US)

( * ) Notice: Subject to any disclaimer, the term of this patent is extended or adjusted under 35 U.S.C. 154(b) by 0 days.

(21) Appl. No.: 14/074,830

(22) Filed: Nov. 8, 2013

(65) Prior Publication Data
US 2014/0135360 A1 May 15, 2014

Related U.S. Application Data

(60) Provisional application No. 61/724,339, filed on Nov. 9, 2012.

(51) Int. Cl.
| | |
|---|---|
| *C07C 211/00* | (2006.01) |
| *A61K 31/445* | (2006.01) |
| *C07D 307/81* | (2006.01) |
| *A61K 31/135* | (2006.01) |
| *A61K 31/343* | (2006.01) |
| *A61K 31/357* | (2006.01) |
| *A61K 31/44* | (2006.01) |
| *A61K 31/4453* | (2006.01) |
| *A61K 45/06* | (2006.01) |
| *C07C 215/50* | (2006.01) |
| *C07D 213/38* | (2006.01) |
| *C07D 213/64* | (2006.01) |
| *C07D 317/58* | (2006.01) |
| *C07C 317/32* | (2006.01) |
| *C07D 213/26* | (2006.01) |
| *C07D 213/65* | (2006.01) |
| *C07C 217/54* | (2006.01) |
| *C07C 217/58* | (2006.01) |
| *C07D 295/088* | (2006.01) |

(52) U.S. Cl.
CPC ............ *C07D 307/81* (2013.01); *A61K 31/135* (2013.01); *A61K 31/343* (2013.01); *A61K 31/357* (2013.01); *A61K 31/44* (2013.01); *A61K 31/4453* (2013.01); *A61K 45/06* (2013.01); *C07C 215/50* (2013.01); *C07D 213/38* (2013.01); *C07D 213/64* (2013.01); *C07D 317/58* (2013.01); *C07C 317/32* (2013.01); *C07D 213/26* (2013.01); *C07D 213/65* (2013.01); *C07C 217/54* (2013.01); *C07C 217/58* (2013.01); *C07D 295/088* (2013.01); *C07C 2101/04* (2013.01); *C07C 2101/08* (2013.01); *C07C 2101/14* (2013.01); *C07C 2102/42* (2013.01); *C07C 2103/74* (2013.01)
USPC ........................................... 514/317; 564/384

(58) Field of Classification Search
None
See application file for complete search history.

(56) References Cited

U.S. PATENT DOCUMENTS

| | | | |
|---|---|---|---|
| 7,589,127 B2 | 9/2009 | Dorn | |
| 8,367,078 B2 * | 2/2013 | Sayeski et al. | ................ 424/400 |

FOREIGN PATENT DOCUMENTS

WO WO 2014/074778 5/2014

OTHER PUBLICATIONS

Childs, G. et al., Am. H. Trop. Med. Hyg. 1988, vol. 38, pp. 19-23.*
Silverman, R. "The Organic Chemistry of Drug Design and Drug Action," 2004, Elsevier, pp. 29-32.*
Burckhalter, J. et al., J. Amer Chem. Soc. 1946, vol. 68, pp. 1894-190.*
Duncan, W. et al., J. Med. Chem. (1969), 12, 711-12.*
Burckhalter, J. H., et al, "Aminoalkylphenols as Antimalarials (heterocyclicamino)-Alpha-Amino-o-Cresols; The Synthesis of Camoquin", J. Am. Chem. Soc., Apr. 1948, 70(4), 1363-1373.
Hung et al, "Camoform Analogs As Potential Agents Against Mefloquine Resistant Malaria", Eur. J. Med. Chem., Chimie Therapeutique, Editions Dimeo, Arcueil, FR, Jan. 1, 1983, 18(1), 61-66.
Karle, J. M., et al., "crystal and molecular structure of the Antimalarial agent 4-(tert-butyl)-2-(tert-butylaminomethyl)-6-(4-chlorophenyl)phenol dihydrogen phosphate (WR 194,965 phosphate)", Antimicrobial Agents and Chemotherapy, Apr. 1988, 32, 540-546.
Peters, W., et al, "The Chemotherapy of Rodent Malaria, XXXVIII. Studies on the Activity of Three New Antimalarials (WR 194,965, WR 228,258 and WR 225,448) Against Rodent and Human Malaria Parasites (*Plasmodium berghei* and *P. falciparum*", 1984, 78, 567-579.
Peters, W., et al., "The chemotherapy of rodent malaria, XXXVII. The In Vivo Action of Two Mannich Bases, WR 194,965 and WR 228,258 and an 8-aminoquinoline WR 225,448", Annals of Tropical Medicine & Parasitology, Dec. 1984, 78(6), 561-565.
Powles, M.A., et al., "MK-4815, a Potential New Oral Agent for Treatment of Malaria" Antimicrobial Agents and Chemotherapy, Feb. 2012, 56(5), 2414-2419.

(Continued)

*Primary Examiner* — Heidi Reese
(74) *Attorney, Agent, or Firm* — Baker & Hostetler LLP

(57) ABSTRACT

The present invention relates to antimalarial compounds and their use against protozoa of the genus *Plasmodium*, including drug-resistant Plasmodia strains. This invention further relates to compositions containing such compounds and a process for making the compounds.

26 Claims, No Drawings

(56) References Cited

OTHER PUBLICATIONS

Schmidt, L. H., et al., "Antimalarial Activities of WR-194,965, an α-Amino-o-Cresol Derivative", Antimicrobial Agents and Chemotherapy, 1978, 14(5), 672-679.

Werbel et al, "Synthesis Antimalarial Activity and Quantitative Structure-Activity-Relationship of Tebuquine and a Series of Related 5-[(7-Chloro-4-quinolinyl)amino]-3-[(alkyl amino)methyl][1,1' Biphenyl]-2-o1 s and N-Oxidesu", Journal of Medicinal Chemistry, American Chemical Society, Jan. 1, 1986, 29(6), 924-939.

* cited by examiner

ARYL DERIVATIVES AND USES THEREOF

CROSS REFERENCE TO RELATED APPLICATIONS

This application claims the benefit of U.S. Provisional Application No. 61/724,339, filed Nov. 9, 2012, the entirety of which is incorporated herein by reference.

TECHNICAL FIELD

The present invention relates to antimalarial compounds and their use against protozoa of the genus *Plasmodium*, including drug-resistant Plasmodia strains. This invention further relates to compositions containing such compounds and a process for making the compounds.

BACKGROUND

Malaria is an infectious febrile disease caused by the protozoa of the genus *Plasmodium*, which are parasitic in the red blood cells, and are transmitted by the bites of infected mosquitoes of the genus *Anopheles*. The disease is characterized by attacks of chills, fever, and sweating, occurring at intervals which depend on the time required for development of a new generation parasites in the body. After recovery from acute attack, the disease has a tendency to become chronic, with occasional relapses. There are four human species *Plasmodium falciparum* (*P. falciparum*), *Plasmodium vivax* (*P. vivax*), *Plasmodium malariae* (*P. malariae*) and *Plasmodium ovale* (*P. ovale*).

Among the various forms of human malaria, malaria caused by *P. falciparum*, characterized by severe constitutional symptoms and sometimes causing death, is responsible for the majority of the mortality in humans. *P. falciparum* is dangerous not only because it digests the red blood cell's hemoglobin, but also because it changes the adhesive properties of the cell it inhabits, which causes the cell to stick to the walls of blood vessels. This becomes dangerous when the infected blood cells stick to blood vessels, obstructing blood flow. The disease is prevalent in tropical and subtropical areas of the world including the Amazon region of Brazil, East and Southern Africa and Southeast Asia. According to the World Health Organization World Malaria Report 2011 there were 216 million cases of malaria in 2010 and 81% of these were in the WHO African Region. There were an estimated 655,000 malaria related deaths in 2010 with 86% of the victims being children under 5 years of age.

Malaria has been treated with various drugs throughout recent history including combinations of drugs. However, the emergence of drug resistant strains of malaria has become a significant problem in the treatment of malaria. The WHO recommends artemisinins in combination with other classes of antimalarials (artemisinin-based combination therapies (ACTs)) as the first line treatment for malaria caused by *P. falciparum*. The emergence of *P. falciparum* resistant to artemisinins, confirmed on the Cambodia-Thailand border in 2009 and suspected in parts of Myanmar and Vietnam, highlights the critical need for new malaria drugs from novel chemical classes.

Since the original work of Burckhalter (Burckhalter, J. H., et al., J. Am. Chem. Soc. 1946, 68, 1894-1901 and J. Am. Chem. Soc. 1948, 70, 1363-1373), aminoalkyl phenols have been studied extensively as antimalarial agents (See Wiselogle, F. Y., Ed.; Survey of Antimalarial Drugs, 1941-1945, Vols. I and II, Edwards Bros., Ann Arbor, Mich., and Duncan, W. G., et al., J. Med. Chem. 1969, 12, 711-712). Optimization of the original α-(dialkylamino)-o-cresol template led to the identification of WR-194,965 (Schmidt, L. H., et al., Antimicrobial Agents and Chemotherapy 1978, 14, 672-679, Peters, W., et al., Annals of Tropical Medicine & Parasitology 1984, 78, 561-565, and 1984, 78, 567-579) which was profiled in human clinical trials (Karle, J. M., et al., Antimicrobial Agents and Chemotherapy 1988, 32, 540-546). Further modifications involved addition of the known antimalarial 4-aminoquinoline moiety to the aminoalkyl phenol template and led to the identification of antimalarial compounds such as Amodiaquine (Burckhalter, J. H., et al., J. Am. Chem. Soc. 1948, 70, 1363-1373) and Tebuquine (Werbel, L. M., et al., J. Med. Chem. 1986, 29, 924-939). Recently, 3,5-disubstituted-2-aminoalkylphenols with antimalarial activity have been reported (U.S. Pat. No. 7,589,127, issued Sep. 15, 2009 and Powles, M. A., et al., Antimicrobial Agents and Chemotherapy 2012, 56, 2414-2419).

New antimalarial compounds with exceptional potency, high activity against resistant strains, and good safety profiles are still needed.

SUMMARY

The compounds of the invention are antiprotozoal agents effective in vitro and in vivo against protozoa of the genus *Plasmodium* (*P. falciparum*, *P. bergei*, etc.), the infectious agent responsible for malaria.

The invention is directed to compounds of Formula I:

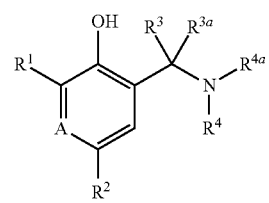

Formula I wherein:
$R^1$ is $C_{6-10}$ aryl optionally substituted with 1, 2, or 3 $R^5$;
A is CH or N;
$R^2$ is $C_{1-10}$ alkyl, $C_{1-10}$ haloalkyl, $C_{1-10}$ alkoxy, $C_{1-10}$haloalkoxy, $C_{6-10}$ aryl substituted with 0-3 $R^5$, heteroaryl substituted with 0-3 $R^5$, or arylalkyl optionally substituted with 1, 2, or 3 $R^5$;
$R^3$ and $R^{3a}$ are, independently, hydrogen, $C_{1-10}$ alkyl or $C_{1-10}$ haloalkyl;
$R^4$ and $R^{4a}$ are, independently, hydrogen, $C_{1-10}$ alkyl or $C_{1-10}$ haloalkyl,
or
$R^4$ and $R^{4a}$ together with the nitrogen atom through which they are attached, form a heterocyclic ring of 4 to 7 ring atoms, where one carbon ring atom may be optionally replaced with $NR^6$, O, S, or $SO_2$, and where any carbon ring atom may be optionally substituted with $C_{1-10}$ alkyl, $C_{1-10}$ haloalkyl, $C_{1-10}$ alkoxy, or $C_{1-10}$ haloalkoxy;
each $R^5$ is independently halo, cyano, hydroxy, $C_{1-10}$ alkyl, $C_{1-10}$ haloalkyl, $C_{1-10}$ alkoxy, $C_{1-10}$ haloalkoxy, aryloxy substituted with 0-3 $R^2$, amino, $C_{1-10}$ alkylamino, $C_{1-10}$ dialkylamino, $C_{1-10}$alkylsulfonyl, sulfamoyl, $C_{1-10}$ alkylsulfamoyl or $C_{1-10}$ dialkylsulfamoyl;
or
two adjacent $R^5$ groups taken together equal methylenedioxy;
$R^6$ is $C_{1-10}$ alkyl or $C_{1-10}$ haloalkyl;
$R^7$ is halo, cyano, hydroxy, $C_{1-10}$ alkyl, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$alkylsulfonyl, sulfamoyl, $C_{1-10}$alkylsulfamoyl or $C_{1-10}$ dialkylsulfamoyl;

provided that when $R^1$ is unsubstituted phenyl, $R^2$ is $C_{6-10}$ aryl substituted with 1, 2, or 3 $R^5$ or heteroaryl optionally substituted with 1, 2, or 3 $R^5$;

or a pharmaceutically acceptable salt, enantiomer, or diastereoisomer thereof; and provided that the compound of Formula I is not:

5-(tert-butyl)-3',4'-dichloro-3-(pyrrolidin-1-ylmethyl)-[1,1'-biphenyl]-2-ol;

5-((3r,5r,7r)-adamantan-1-yl)-4'-chloro-3-((dimethylamino)methyl)-[1,1'-biphenyl]-2-ol;

5-(tert-butyl)-4'-(dimethylamino)-3-((dimethylamino)methyl)-[1,1'-biphenyl]-2-ol;

5-(tert-butyl)-3-((tert-butylamino)methyl)-4'-chloro-[1,1'-biphenyl]-2-ol;

3,3',5,5'-tetrakis((diethylamino)methyl)-[1,1'-biphenyl]-2,2'-diol;

4,4'''-dichloro-5',5''-bis(pyrrolidin-1-ylmethyl)-[1,1':3',1'':3'',1'''-quaterphenyl]-4'',6'-diol;

3,3',5,5'-tetrakis(morpholinomethyl)-[1,1'-biphenyl]-2,2'-diol;

3,3'-bis((diethylamino)methyl)-5,5'-dimethoxy-[1,1'-biphenyl]-2,2'-diol;

or 3-((diethylamino)methyl)-5,5'-dimethoxy-[1,1'-biphenyl]-2,2'-diol.

Methods of making the compounds of Formula I, as well as methods of using the compounds Formula I for treating malaria are also described.

DETAILED DESCRIPTION OF ILLUSTRATIVE EMBODIMENTS

The present invention may be understood more readily by reference to the following description taken in connection with the accompanying Figures and Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement.

The present invention is directed to compounds of Formula I:

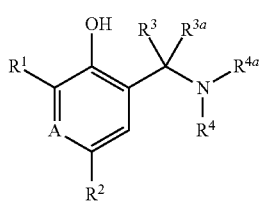

I wherein:

$R^1$ is $C_{6-10}$ aryl optionally substituted with 1, 2, or 3 $R^5$;

A is CH or N;

$R^2$ is $C_{1-10}$ alkyl, $C_{1-10}$ haloalkyl, $C_{1-10}$ alkoxy, $C_{1-10}$ haloalkoxy, $C_{6-10}$ aryl substituted with 0-3 $R^5$, heteroaryl substituted with 0-3 $R^5$, or arylalkyl optionally substituted with 1, 2, or 3 $R^5$;

$R^3$ and $R^{3a}$ are, independently, hydrogen, $C_{1-10}$ alkyl or $C_{1-10}$ haloalkyl;

$R^4$ and $R^{4a}$ are, independently, hydrogen, $C_{1-10}$ alkyl or $C_{1-10}$ haloalkyl, or $R^4$ and $R^{4a}$ together with the nitrogen atom through which they are attached, form a heterocyclic ring of 4 to 7 ring atoms, where one carbon ring atom may be optionally replaced with $NR^6$, O, S, or $SO_2$, and where any carbon ring atom may be optionally substituted with $C_{1-10}$ alkyl, $C_{1-10}$ haloalkyl, $C_{1-10}$ alkoxy, or $C_{1-10}$ haloalkoxy;

each $R^5$ is independently halo, cyano, hydroxy, $C_{1-10}$ alkyl, $C_{1-10}$ haloalkyl, $C_{1-10}$ alkoxy, $C_{1-10}$ haloalkoxy, aryloxy substituted with 0-3 $R^7$, amino, $C_{1-10}$ alkylamino, $C_{1-10}$ dialkylamino, $C_{1-10}$ alkylsulfonyl, sulfamoyl, $C_{1-10}$ alkylsulfamoyl or $C_{1-10}$ dialkylsulfamoyl;

or two adjacent $R^5$ groups taken together equal methylenedioxy;

$R^6$ is $C_{1-10}$ alkyl or $C_{1-10}$ haloalkyl;

$R^7$ is halo, cyano, hydroxy, $C_{1-10}$ alkyl, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylsulfonyl, sulfamoyl, $C_{1-10}$ alkylsulfamoyl or $C_{1-10}$ dialkylsulfamoyl;

provided that when $R^1$ is unsubstituted phenyl, $R^2$ is $C_{6-10}$ aryl substituted with 1, 2 or 3 $R^5$ or heteroaryl optionally substituted with 1, 2, or 3 $R^5$;

or a pharmaceutically acceptable salt, enantiomer, or diastereoisomer thereof;

provided that the compound of Formula I is not:

5-(tert-butyl)-3',4'-dichloro-3-(pyrrolidin-1-ylmethyl)-[1,1'-biphenyl]-2-ol;

5-((3r,5r,7r)-adamantan-1-yl)-4'-chloro-3-((dimethylamino)methyl)-[1,1'-biphenyl]-2-ol;

5-(tert-butyl)-4'-(dimethylamino)-3-((dimethylamino)methyl)-[1,1'-biphenyl]-2-ol;

5-(tert-butyl)-3-((tert-butylamino)methyl)-4'-chloro-[1,1'-biphenyl]-2-ol;

3,3',5,5'-tetrakis((diethylamino)methyl)-[1,1'-biphenyl]-2,2'-diol;

4,4'''-dichloro-5',5''-bis(pyrrolidin-1-ylmethyl)-[1,1':3',1'':3'',1'''-quaterphenyl]-4'',6'-diol;

3,3',5,5'-tetrakis(morpholinomethyl)-[1,1'-biphenyl]-2,2'-diol;

3,3'-bis((diethylamino)methyl)-5,5'-dimethoxy-[1,1'-biphenyl]-2,2'-diol;

or 3-((diethylamino)methyl)-5,5'-dimethoxy-[1,1'-biphenyl]-2,2'-diol;

or a pharmaceutically acceptable salt, enantiomer, or diastereoisomer thereof.

In preferred embodiments of Formula I, A is CH. In other embodiments, A is N.

In other embodiments of Formula I, $R^3$ and $R^{3a}$ are H. In some embodiments $R^{3a}$ is H and $R^3$ is $C_{1-10}$ alkyl or $C_{1-10}$ haloalkyl.

In some embodiments of Formula I, $R^4$ is $C_{1-10}$ alkyl and $R^{4a}$ is H. In other embodiments, $R^4$ is $C_{1-10}$haloalkyl and $R^{4a}$ is H. Preferably, $R^4$ is tert-butyl or 1-methylcyclobutyl and $R^{4a}$ is H.

In still other embodiments of Formula I, $R^2$ is tert-butyl, $R^1$ is $C_{6-10}$ aryl optionally substituted with 1, 2, or 3 $R^5$ or heteroaryl optionally substituted with 1, 2, or 3 $R^5$.

In exemplary embodiments of Formula I, $R^2$ is $C_{1-10}$ alkyl, preferably tert-butyl.

In preferred embodiments of Formula I, $R^1$ is phenyl substituted with 1-3 groups of $R^5$, wherein $R^5$ is halo, cyano, $—CF_3$ or $—OCF_3$.

In some embodiments of Formula I, $R^1$ is phenyl substituted with 1-3 groups of $R^5$; A is CH; $R^3$ and $R^{3a}$ are H; $R^4$ is tert-butyl or 1-methylcyclobutyl and $R^{4a}$ is H; $R^2$ is tert-butyl, $C_{6-10}$ aryl optionally substituted with 1, 2, or 3 $R^5$ or heteroaryl optionally substituted with 1, 2, or 3 $R^5$.

In other embodiments of Formula I, $R^1$ is phenyl substituted with 1, 2, or 3 groups of $R^5$, A is CH; $R^3$ and $R^{3a}$ are H; $R^4$ is tert-butyl and $R^{4a}$ is H; and $R^2$ is tert-butyl.

In preferred embodiments, $R^2$ is pyridyl optionally substituted with 1, 2, or 3 $R^5$. In other embodiments, $R^2$ is benzofuranyl optionally substituted with 1, 2, or 3 $R^5$. In still other embodiments, $R^2$ is —$OCF_3$ or —Oalkaryl.

Preferred embodiments of the invention include compounds of Formula I that are compounds of Formula IA;

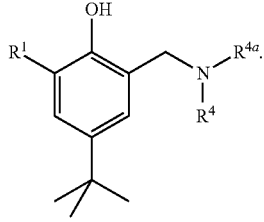

IA

In embodiments including compounds of Formula IA $R^4$ and $R^{4a}$ are, independently, hydrogen or $C_{1-10}$ alkyl or $R^4$ and $R^{4a}$, together with the nitrogen atom through which they are attached, form a heterocyclic ring of 4 to 7 ring atoms.

In preferred embodiments of Formula IA, $R^1$ is unsubstituted naphthyl. In other embodiments, $R^1$ is substituted phenyl.

In other embodiments of Formula IA, $R^1$ is substituted with 1, 2, or 3 of $R^5$, wherein each $R^5$ is independently —$CF_3$, —$OCF_3$, —$SO_2C_{1-6}$alkyl, F, Cl, Br, —Ophenyl.

In other preferred embodiments of the invention, the compound of Formula I is a compound of Formula IB:

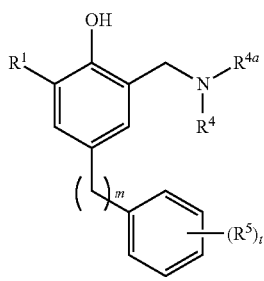

IB wherein m is from 0 to 4 and t is from 0 to 3.

In preferred compounds of Formula IB, m is 0. In other embodiments, m is from 1 to 4.

In some embodiments of compounds of Formula IB, $R^1$ is substituted phenyl. In others, $R^1$ is unsubstituted naphthyl.

In other preferred embodiments of Formula IB, $R^4$ and $R^{4a}$ are, independently, hydrogen or $C_{1-10}$ alkyl or $R^4$ and $R^{4a}$, together with the nitrogen atom through which they are attached, form a heterocyclic ring of 4 to 7 ring atoms.

In some embodiments of Formula IB, t is 0. In other embodiments, t is from 1 to 3. In such embodiments, $R^5$ can be independently —$CF_3$, —$OCF_3$, —$SO_2C_{1-6}$alkyl, F, Cl, Br, —Ophenyl.

Preferred compounds of Formula I include:

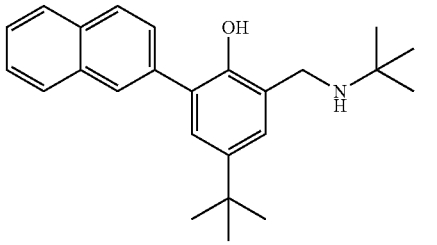 [SMILES: CC(C)(C)NCc1cc(C(C)(C)C)cc(-c2ccc3ccccc3c2)c1O]

4-(tert-butyl)-2-((tert-butylamino)methyl)-6-(naphthalen-2-yl)phenol,

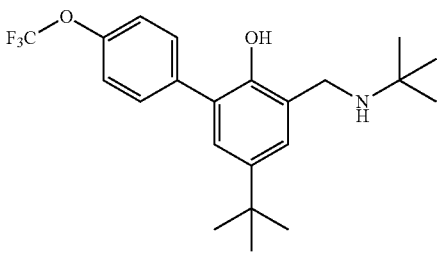 [SMILES: CC(C)(C)NCc1cc(C(C)(C)C)cc(-c2ccc(OC(F)(F)F)cc2)c1O]

5-(tert-butyl)-3-((tert-butylamino)methyl)-4'-(trifluoromethoxy)-[1,1'-biphenyl]-2-ol,

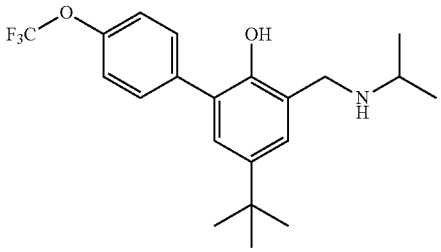 [SMILES: CC(C)NCc1cc(C(C)(C)C)cc(-c2ccc(OC(F)(F)F)cc2)c1O]

5-(tert-butyl)-3-((isopropylamino)methyl)-4'-(trifluoromethoxy)-[1,1'-biphenyl]-2-ol,

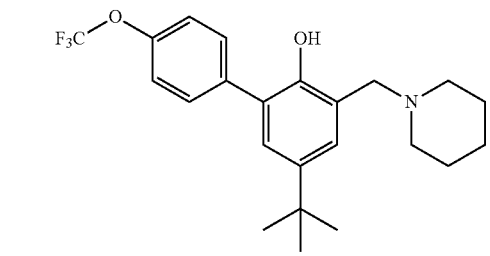 [SMILES: CC(C)(C)c1cc(CN2CCCCC2)c(O)c(-c2ccc(OC(F)(F)F)cc2)c1]

5-(tert-butyl)-3-(piperidin-1-ylmethyl)-4'-(trifluoromethoxy)-[1,1'-biphenyl]-2-ol,

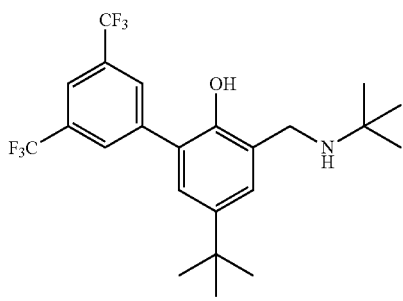 [SMILES: CC(C)(C)NCc1cc(C(C)(C)C)cc(-c2cc(C(F)(F)F)cc(C(F)(F)F)c2)c1O]

5-(tert-butyl)-3-((tert-butylamino)methyl)-3',5'-bis(trifluoromethyl)-[1,1'-biphenyl]-2-ol,

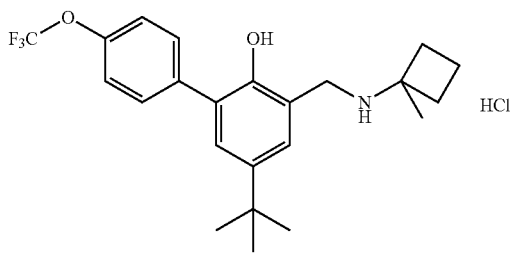 [SMILES: CC1(NCc2cc(C(C)(C)C)cc(-c3ccc(OC(F)(F)F)cc3)c2O)CCC1 ; Cl]

5-(tert-butyl)-3-(((1-methylcyclobutyl)amino)methyl)-4'-(trifluoromethoxy)-[1,1'-biphenyl]-2-ol hydrochloride,

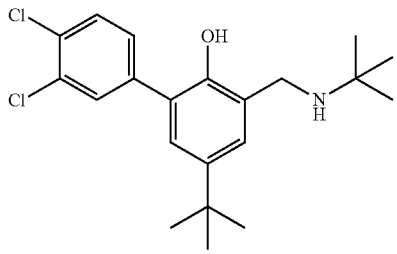 [SMILES: CC(C)(C)NCc1cc(C(C)(C)C)cc(-c2ccc(Cl)c(Cl)c2)c1O]

5-(tert-butyl)-3-((tert-butylamino)methyl)-3',4'-dichloro-[1,1'-biphenyl]-2-ol,

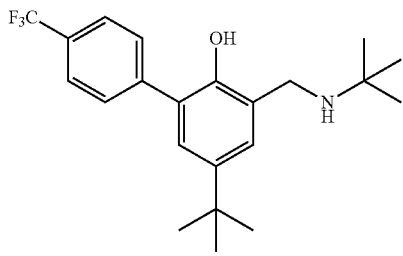

5-(tert-butyl)-3-((tert-butylamino)methyl)-4'-(trifluoromethyl)-[1,1'-biphenyl]-2-ol,

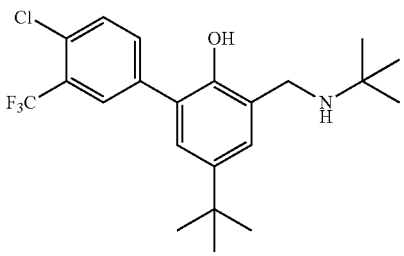

5-(tert-butyl)-3-((tert-butylamino)methyl)-4'-chloro-3'-(trifluoromethyl)-[1,1'-biphenyl]-2-ol,

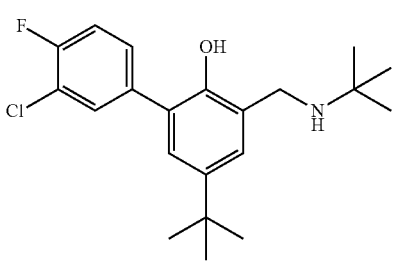 [SMILES: CC(C)(C)NCc1cc(C(C)(C)C)cc(-c2ccc(F)c(Cl)c2)c1O]

5-(tert-butyl)-3-((tert-butylamino)methyl)-3'-chloro-4'-fluoro-[1,1'-biphenyl]-2-ol,

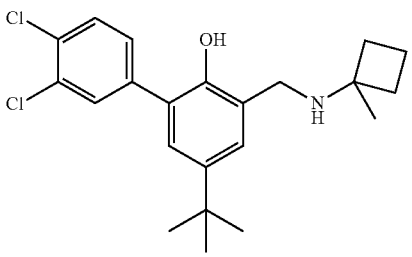 [SMILES: CC1(NCc2cc(C(C)(C)C)cc(-c3ccc(Cl)c(Cl)c3)c2O)CCC1]

5-(tert-butyl)-3',4'-dichloro-3-(((1-methylcyclobutyl)amino)methyl)-[1,1'-biphenyl]-2-ol,

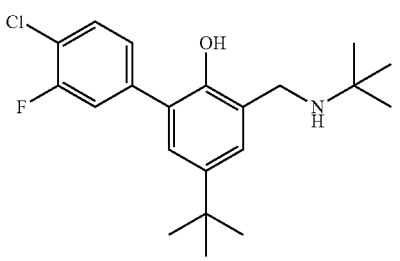

5-(tert-butyl)-3-((tert-butylamino)methyl)-4'-chloro-3'-fluoro-[1,1'-biphenyl]-2-ol,

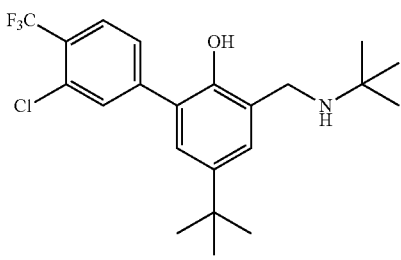 [SMILES: CC(C)(C)NCc1cc(C(C)(C)C)cc(-c2ccc(C(F)(F)F)c(Cl)c2)c1O]

5-(tert-butyl)-3-((tert-butylamino)methyl)-3'-chloro-4'-(trifluoromethyl)-[1,1'-biphenyl]-2-ol,

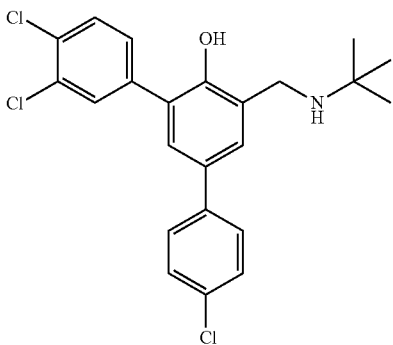 [SMILES: CC(C)(C)NCc1cc(-c2ccc(Cl)cc2)cc(-c2ccc(Cl)c(Cl)c2)c1O]

5'-((tert-butylamino)methyl)-3",4,4"-trichloro-[1,1':3',1"-terphenyl]-4'-ol,

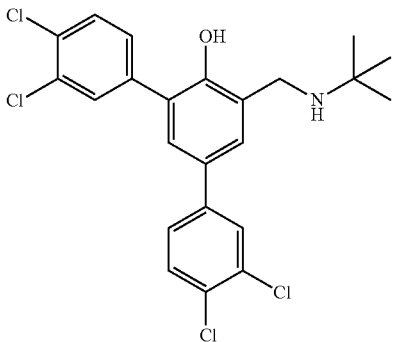 [SMILES: CC(C)(C)NCc1cc(-c2ccc(Cl)c(Cl)c2)cc(-c2ccc(Cl)c(Cl)c2)c1O]

5'-((tert-butylamino)methyl)-3,3",4,4"-tetrachloro-[1,1':3',1"-terphenyl]-4'-ol,

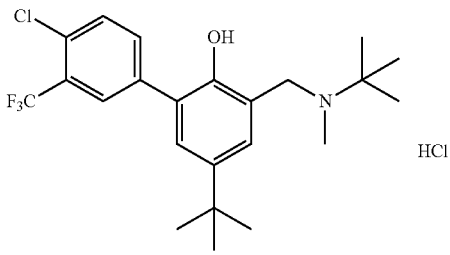 [SMILES: CN(Cc1cc(C(C)(C)C)cc(-c2ccc(Cl)c(C(F)(F)F)c2)c1O)C(C)(C)C ; Cl]

5-(tert-butyl)-3-((tert-butyl(methyl)amino)methyl)-4'-chloro-3'-(trifluoromethyl)-[1,1'-biphenyl]-2-ol,

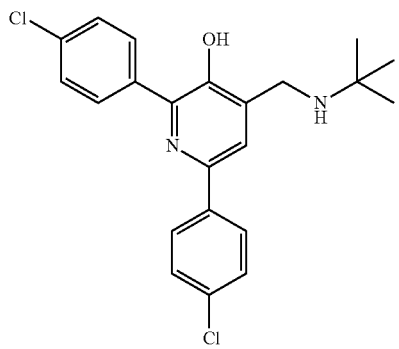 [SMILES: CC(C)(C)NCc1cc(-c2ccc(Cl)cc2)nc(-c2ccc(Cl)cc2)c1O]

4-((tert-butylamino)methyl)-2,6-bis(4-chlorophenyl)pyridin-3-ol, and pharmaceutically acceptable salts thereof.

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

As employed above and throughout the disclosure, the following terms, unless otherwise indicated, shall be understood to have the following meanings.

The terms "*Plasmodium* falciparum" and "*P. falciparum*" are interchangeably used herein and refer to the parasite that is transmitted to human and animal hosts, resulting in the host showing one or more symptoms of malaria. More specifically, *P. falciparum* is a protozoan that causes malaria.

As used herein, "alkyl" includes a saturated straight, branched, cyclic, or multicyclic hydrocarbon having from 1 to about 20 carbon atoms (and all combinations and subcombinations of ranges and specific numbers of carbon atoms therein). The term "lower alkyl" herein refers to those alkyl groups having from about 1 to about 10 carbon atoms, these being preferred. Alkyl groups include, but are not limited to, methyl, ethyl, n-propyl, isopropyl, cyclopropyl, n-butyl, isobutyl, t-butyl, cyclobutyl, n-pentyl, cyclopentyl, isopentyl, neopentyl, n-hexyl, isohexyl, cyclohexyl, cycloheptyl, cyclooctyl, decahydronaphthalenyl, adamantyl, 3-methylpentyl, 2,2-dimethylbutyl, and 2,3-dimethylbutyl. Alkyl groups can be substituted or unsubstituted.

As used herein, "halogen" or "halo" includes fluoro, chloro, bromo and iodo.

As used herein, "haloalkyl" includes an alkyl group substituted with one or more halo groups selected from —F or —Cl. An example of a haloalkyl group includes —$CF_3$.

As used herein, "alkoxy" includes an alkyl-O— moiety, wherein "alkyl" is defined as above.

As used herein, "haloalkoxy" includes an alkoxy group substituted with one or more halo groups selected from —F and —Cl. An example of a haloalkoxy group includes —$OCF_3$.

As used herein, "aryl" includes a mono-, di-, tri-, or other multicyclic aromatic ring system having from about 5 to about 30 carbon atoms (and all combinations and subcombinations of ranges and specific numbers of carbon atoms therein), with from about 6 to about 14 carbons being preferred. Non-limiting examples include phenyl, naphthyl, anthracenyl, and phenanthrenyl. Aryl groups can be substituted or unsubstituted.

As used herein, "aralkyl" or "arylalkyl" includes aryl-substituted alkyl radicals having from about 6 to about 50 carbon atoms (and all combinations and subcombinations of ranges and specific numbers of carbon atoms therein), with from about 6 to about 20 carbon atoms being preferred. Non-limiting examples include, for example, benzyl, phenylethyl, 3-phenylprop-1-yl, tetrahydronaphthalenyl, 3-phenylprop-2-yl, and 4-naphthylhex-1-yl.

Aralkyl groups can be substituted or unsubstituted. Substitution may occur on the aryl ring carbons or alkyl carbons of the aralkyl.

As used herein, "heteroaryl" includes a mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples include, for example, monocyclic heteroaryl groups such as pyrrolyl, furyl, pyridyl, 1,2,4-thiadiazolyl, pyrimidyl, isothiazolyl, thiazolyl, triazolyl, imidazolyl, tetrazolyl, pyrazinyl, thienyl, pyrazolyl, oxazolyl, and isoxazolyl, and the fused bicyclic moieties formed by fusing one of these monocyclic groups with a phenyl ring or with any of the heteroaromatic monocyclic groups to form a bicyclic group such as indolyl, indazolyl, benzimidazolyl, benzotriazolyl, benzothienyl, benzofuryl, isobenzofuryl, benzothiazolyl, quinolyl, isoquinolyl, purinyl, pyrazolopyridyl, quinazolinyl, quinoxalinyl, and the like. Heteroaryl groups can be substituted or unsubstituted.

Typically, substituted chemical moieties include one or more substituents that replace hydrogen. Exemplary substituents include, for example, halo (e.g., —F, —Cl, —Br), (provided that when halo is —Br, the —Br is attached to an sp2 carbon such as on a carbon of an alkenyl or a ring carbon of aryl or heteroaryl group), alkoxy, haloalkoxy, —$OCF_3$, alkylthio, monohaloalkylthio, polyhaloalkylthio, —$SCF_3$, alkyl, —$CF_3$, haloalkyl, lower alkyl, spiroalkyl, alkenyl, alkynyl, aralkyl, aryl, heteroaryl, heterocyclyl, hydroxyl (—OH), nitro (—$NO_2$), cyano (—CN), sulfonyl (—$SO_2R$), sulfamoyl (—$SO_2NR^aR^b$), —$NR^aSO_2R^b$, —SR, amino (—$NH_2$, —NHR, —$NR^aR^b$), —$CO_2R$, —COR, —CH(OH)R, —C(OH)$R^aR^b$, —CONR$^aR^b$, —NHCOR, —NR$^a$COR$^b$, and the like.

As used herein, "pharmaceutically acceptable" includes those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" includes derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Certain acidic or basic compounds of the present invention may exist as zwitterions. All forms of the compounds, including free acid, free base, and zwitterions, are contemplated to be within the scope of the present invention.

All forms of the compounds, including free acid, free base, and zwitterions, isomorphic crystalline forms, all chiral and racemic forms, hydrates, solvates, and acid salt hydrates, are contemplated to be within the scope of the present invention.

"Patient" refers to an animal, including a mammal, preferably a human.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer.

When any variable occurs more than one time in any constituent or in any formula, its definition in each occurrence is independent of its definition at every other occurrence. Thus, for example, if an $R^1$ group is shown to be substituted with, for example, 1 to 5 of —CN, —OCF$_3$, haloalkoxy, —SCF$_3$, haloalkylthio, —SR$^4$, —NR$^5$R$^6$, —SO$_2$R$^4$, —SO$_2$NR$^5$R$^{6a}$, heteroaryl, or heterocyclyl, then the $R^1$ group may optionally be substituted with up to five of the above mentioned substituents, and the substituent at each occurrence is selected independently from the above defined list of possible substituents. Combinations of substituents and/or variables are permissible only if such combinations result in stable compounds. It is further understood that, while certain substituents are minimally required, such as, for example in the $R^1$ moiety, the moiety may be further substituted with the same substituent(s), another substituent(s) from the group of required substituents, or other substituent(s) not from the group of required substituents.

Compounds of the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

In certain embodiments, the invention is directed to compositions, comprising: at least one compound of formula I or a pharmaceutically acceptable salt thereof; and at least one pharmaceutically acceptable carrier.

Such compositions are prepared in accordance with acceptable pharmaceutical procedures, such as described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The water solubility of the hydrochloride salts and most other salts of the parent compounds may be limited, so when solutions are required it may be preferable to add solubilizing agents to the water, such as non-aqueous solvents. Alternatively, a more soluble salt may be used or a very dilute solution prepared.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Oral formulations are preferred and this invention has the advantage over related products of being readily absorbed by mammals at sufficient levels to make the compounds of the present invention orally active as therapeutic agents. Formulations for oral or injected use are based on sufficient solubility as to allow the therapeutic agent to enter solution in the stomach or in an injectable medium. Suitable drug formulations include, but are not limited to, tablets, pills, capsules, sachets, granules, powders, chewing gums, suspensions, emulsions, suppositories, and solutions. Particularly preferred for oral use are tablets and capsules of all varieties and microbe-free solutions for injection or infusion. Where appropriate and necessary the formulations may include diluents, binding agents, dispersing agents, surfaceactive agents, lubricating agents, coating materials, flavoring agents, coloring agents, controlled release formulations, sweeteners or any other pharmaceutically acceptable additives, for example, gelatin, sodium starch glycolate, lactose, starch, talc, magnesium stearate, microcrystalline cellulose, Povidone, hydrogenated or unsaturated oils, polyglycols, syrups or other aqueous solutions. Where the formulations are tablets or capsules and the like the formulations may be presented as premeasured unit doses or in multidose containers from which the appropriate unit dose may be withdrawn.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions, which are sterile solutions or suspensions, can be administered by, for example, intramuscular, intraperitoneal or subcutaneous injection.

Sterile solutions can also be administered intravenously. Oral administration may be either liquid or solid composition form. The injectable form may be an aqueous or nonaqueous solution, suspension or emulsion in a pharmaceutically acceptable liquid, e.g. sterile pyrogen-free water or parenterally acceptable oils or mixture of liquids which may contain bacteriostatic agents, antioxidants or other preservatives and stabilizers, buffers (preferably but not limited to a physiological pH range of 6.5-7.7, solutes to render the solution isotonic with the blood, thickening agents, suspending agents or other pharmaceutically acceptable additives. Such forms will be presented in unit dose form such as ampules or disposable injection devices or in multi-dose forms such as a bottle from which the appropriate dose may be withdrawn, or as a solid form or concentrate that can be used to quickly prepare an injectable formulation. All formulations for injection are preferable as sterile and pyrogen free. Suppositories containing the compound will also contain suitable carriers, e.g. cocoa butter, polyglycols or other state-of-the-art carriers.

Preferably, the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In addition to standard pharmaceutical additives there may be included within formulations of the compound other therapeutic agents, particularly including other antimalarial agents and antiinfective agents.

The compounds of the present invention may be prepared in a number of ways well known to those skilled in the art of which the following generally applicable multi-step processes are preferred. These multi-step processes typically utilize readily available starting materials. Intermediate products, if commercially available, may simplify or obviate some of the process steps. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups can be employed with the present invention. Protecting groups that may be employed in accordance with the present invention may be described in Wuts, P. G. M. and Greene, T. W., Greene's Protective Groups in Organic Synthesis 4th Ed., Wiley & Sons, 2007.

A preferred synthesis of the compounds of Formula I ($R^3$, $R^{3a}$, $R^{4a}$=H) is shown in Scheme 1.

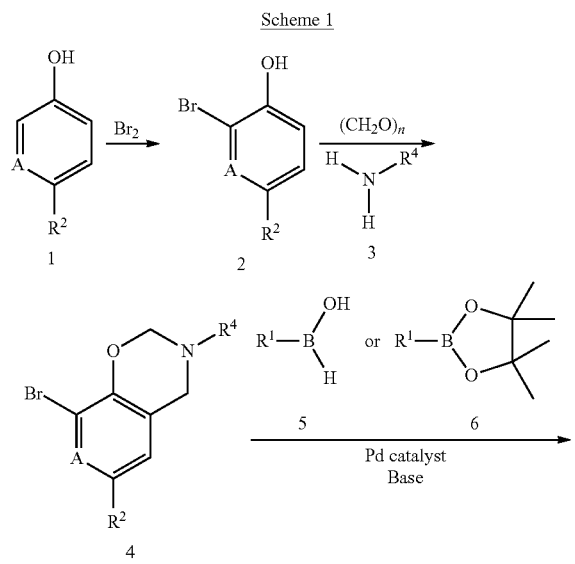

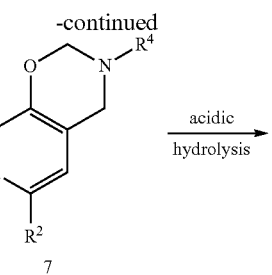

Selective ortho-bromination of a substituted phenol of general formula 1 gives the 2-bromophenol of general formula 2. Any conventional method for brominating a phenol can be utilized. In accordance with the preferred embodiment of this invention, a solution of phenol of general formula 1 in chlorinated solvent is treated with one equivalent of bromine at 0° C. to about 40° C. to give the 2-bromophenol of general formula 2. The next step involves a Mannich reaction of the 2-bromophenol of general formula 2 with excess paraformaldehyde and primary amine of general formula 3 to give the 8-bromo-3,4-dihydro-2H-benzo[e][1,3]oxazine of general formula 4. The reaction may be conducted at a variety of temperatures which depend on the relative reactivity of the 2-bromophenol 2 and imine formed from reaction of the primary amine 3 with paraformaldehyde. In accordance with the preferred embodiment of this invention, the 2-bromophenol of general formula 2 is treated with 5 equivalents of paraformaldehyde and 5 equivalents of primary amine of general formula 3 in isopropanol as solvent at around 80° C. The initially formed 2-aminomethylphenol reacts with additional imine to give the 8-bromo-3,4-dihydro-2H-benzo[e][1,3]oxazine of general formula 4. The next step involves a Suzuki reaction of the 8-bromo-3,4-dihydro-2H-benzo[e][1,3]oxazine of general formula 4 with either an arylboronic acid of general formula 5 or arylboronic ester of general formula 6 in the presence of a palladium catalyst and base in a suitable solvent to give the 8-aryl-3,4-dihydro-2H-benzo[e][1,3]oxazine of general formula 7. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine. A wide variety of solvents can be utilized including dimethoxyethane, tetrahydrofuran, dioxane, toluene and water. The reaction may be conducted at a variety of temperatures that range from ambient temperature to about 120° C. In accordance with the preferred embodiment of this invention, the 8-bromo-3,4-dihydro-2H-benzo[e][1,3]oxazine of general formula 4 is treated with one equivalent of arylboronic acid of general formula 5 or arylboronic ester of general formula 6 and 1.5 equivalents of potassium carbonate in the presence of catalytic (tetrakistriphenylphosphine)palladium (0) in a solvent mixture of dimethoxyethane and water at around 80° C. to give the 8-aryl-3,4-dihydro-2H-benzo[e][1,3]oxazine of general formula 7. The final step in the synthesis of the novel compounds of general Formula I is the hydrolysis of the 8-aryl-3,4-dihydro-2H-benzo[e][1,3]oxazine intermediate of general formula 7 to give compounds of general Formula I ($R^3$, $R^{3a}$, $R^{4a}$=H). The hydrolysis is generally conducted under acidic conditions in the presence of a mineral acid such as aqueous hydrochloric or sulfuric acid. A co-solvent such as an alcohol is usually added to the reaction mixture and the reaction is conducted at temperatures between ambient temperature and about 100° C. for periods of a few hours to a few days.

In some instances it may be advantageous to reverse the coupling partners in the Suzuki reaction and an alternative synthesis of the intermediate 8-aryl-3,4-dihydro-2H-benzo[e][1,3]oxazine of general formula 7 is shown in Scheme 2.

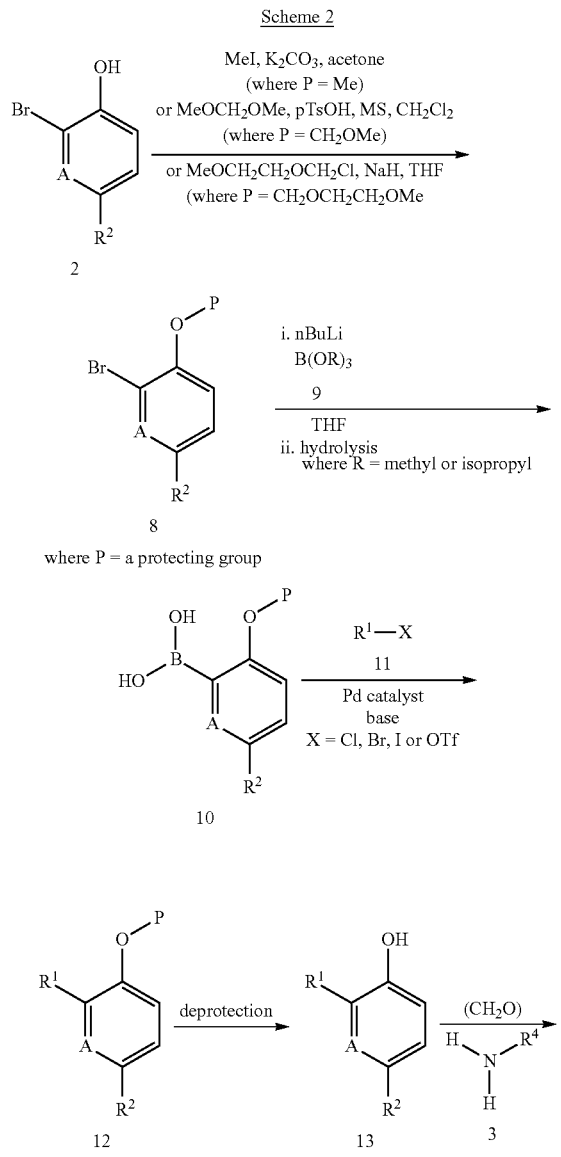

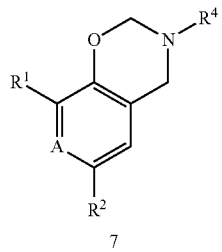

In order to allow for the use of an alkyl lithium in the synthetic route the 2-bromophenol of general formula 2 is protected. A large variety of phenol protecting groups that are stable in the presence of alkyl lithiums could be employed, for example those described in Wuts, P. G. M. and Greene, T. W., Greene's Protective Groups in Organic Synthesis 4$^{th}$ Ed., Wiley & Sons, 2007. In accordance with the preferred embodiment of this invention, the 2-bromophenol of general formula 2 is protected as a methyl ether, methoxymethyl ether (MOM ether) or methoxyethoxymethyl ether (MEM ether). Reaction conditions to achieve the desired phenol protection are described in Wuts, P. G. M. and Greene, T. W., Greene's Protective Groups in Organic Synthesis 4$^{th}$ Ed., Wiley & Sons, 2007. In accordance with the preferred embodiment of this invention, the methyl ether of general formula 8 (where P=Me) is prepared by treatment of the 2-bromophenol of general formula 2 with potassium carbonate and iodomethane or dimethylsulfate in acetone at temperatures ranging between ambient temperature and the reflux temperature of the solvent. Alternatively, to prepare the methoxymethyl ether of general formula 8 (where P=MOM), the 2-bromophenol of general formula 2 is treated with dimethoxymethane and para-toluenesulfonic acid in chlorinated solvent, in the presence of molecular sieves to absorb methanol, at temperatures ranging between ambient temperature and the reflux temperature of the solvent. To prepare the methoxyethoxymethyl ether of general formula 8 (where P=MEM), the 2-bromophenol of general formula 2 is treated with sodium hydride in tetrahydrofuran followed by 2-methoxyethoxymethyl chloride at temperatures ranging from 0° C. to the reflux temperature of the solvent. The next step involves a halogen metal exchange reaction of the bromide of general formula 8 with an alkyl lithium to give an aryl lithium which is reacted directly with a trialkyl borate of general formula 9 to give a boronic acid of general formula 10 after aqueous hydrolysis. In accordance with the preferred embodiment of this invention, a solution bromide of general formula 8 and trimethyl or triisopropyl borate in tetrahydrofuran at −78° C. under inert atmosphere is treated with butyllithium solution in hexanes. The reaction is allowed to warm to around −10° C. then quenched with water to give the boronic acid of general formula 10. The next step involves a Suzuki reaction of the boronic acid of general formula 10 with an aryl chloride, bromide, iodide or trifluoromethanesulfonate of general formula 11 (X=Cl, Br, I, or OTf) in the presence of a palladium catalyst and base in a suitable solvent to give a compound of general formula 12. A wide variety of catalyst systems can be utilized with the optimal catalyst, base and solvent dependant on the chemical composition of the boronic acid 10 and aryl chloride, bromide, iodide or trifluoromethanesulfonate 11 coupling partners. Non-limiting examples of suitable palladium catalysts include tetrakis (triphenylphosphine)palladium (0), dichloro[1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine. A wide variety of solvents can be utilized including dimethoxyethane, tetrahydrofuran, dioxane, toluene and water. The reaction may be conducted at a variety of temperatures that range from ambient temperature to about 120° C. The next step involves removal of the preferred methyl, methoxymethyl (MOM) or methoxyethoxymethyl (MEM) protecting group. Reaction conditions to achieve the desired phenol deprotection are described in Wuts, P. G. M. and Greene, T. W., Greene's Protective Groups in Organic Synthesis 4th Ed., Wiley & Sons, 2007. In accordance with the preferred embodiment of this invention, a solution of methyl ether of general formula 12 (where P=Me) in chlorinated solvent is treated with boron tribromide at temperatures ranging between 0° C. and the reflux temperature of the solvent for several hours to several days to give the 2-arylphenol of general formula 13. The final step in the alternative synthesis of intermediate 8-aryl-3,4-dihydro-2H-benzo[e][1,3]oxazine of general formula 7 involves a Mannich reaction of the 2-arylphenol of general formula 13 with excess paraformaldehyde and primary amine of general formula 3. The reaction may be conducted at a variety of temperatures that depend on the relative reactivity of the phenol 13 and imine formed from reaction of the primary amine 3 with paraformaldehyde. In accordance with the preferred embodiment of this invention, the 2-arylphenol of general formula 13 is treated with 5 equivalents of paraformaldehyde and 5 equivalents of primary amine in isopropanol as solvent at around 80° C. The initially formed 2-aminomethylphenol reacts with additional imine to give the 8-aryl-3,4-dihydro-2H-benzo[e][1,3]oxazine of general formula 7.

A preferred synthesis of novel compounds of general Formula I ($R^3$, $R^{3a}$=H) is shown in Scheme 3.

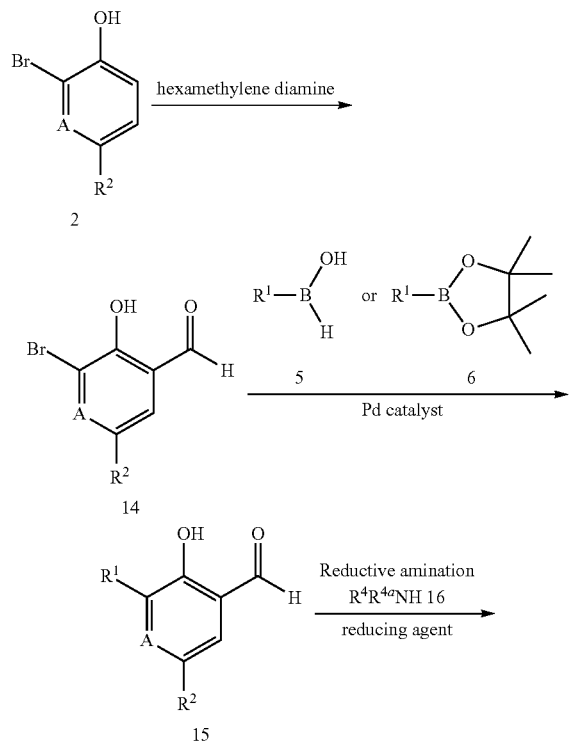

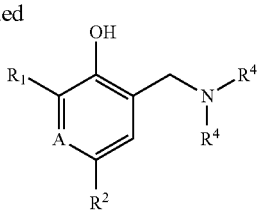

Formula I (where $R^3$, $R^{3a}$ = H)

Ortho-formylation of a 2-bromophenol of general formula 2 gives the 3-bromo-2-hydroxybenzaldehyde of general formula 14. A number of reactions are available to accomplish this transformation including the Reimer-Tiemann reaction of a phenol with chloroform in the presence of a strong base (for a review see Wynberg, H and Meijer, E. W. Org. React. 1982, 28, 2) or Duff reaction of a phenol with hexamethylenetetramine in the presence of acid. In accordance with the preferred embodiment of this invention, a solution of 2-bromophenol of general formula 2 and excess hexamethylenetetratramine in trifluoroacetic acid is refluxed under an inert atmosphere for a period of several hours to several days to give the 3-bromo-2-hydroxybenzaldehyde of general formula 14. The next step involves a Suzuki reaction of the 3-bromo-2-hydroxybenzaldehyde of general formula 14 with either an arylboronic acid of general formula 5 or arylboronic ester of general formula 6 in the presence of a palladium catalyst and base in a suitable solvent to give the 3-aryl-2-hydroxybenzaldehyde of general formula 15. A wide variety of catalyst systems can be utilized with the optimal catalyst, base and solvent dependant on the chemical composition of the bromide and boronic acid or ester coupling partners. Non-limiting examples of suitable palladium catalysts include tetrakis(triphenylphosphine)palladium (0), dichloro [1,1'-bis(diphenylphosphino)ferrocene]palladium(II) dichloromethane adduct, and trans-dichlorobis(triphenylphosphine)palladium (II). Potential bases include potassium carbonate, sodium carbonate, cesium carbonate, potassium acetate, potassium phosphate and triethylamine. A wide variety of solvents can be utilized including dimethoxyethane, tetrahydrofuran, dioxane, toluene, 2-propanol and water. The reaction may be conducted at a variety of temperatures that range from ambient temperature to about 120° C. In accordance with the preferred embodiment of this invention, the 3-bromo-2-hydroxybenzaldehyde of general formula 14 is treated with 1.1 equivalents of arylboronic acid of general formula 5 or arylboronic ester of general formula 6 and 2.5 equivalents of potassium carbonate in the presence of catalytic (tetrakistriphenylphosphine)palladium (0) in a solvent mixture of dimethoxyethane and water at around 80° C. to give the 3-aryl-2-hydroxybenzaldehyde of general formula 15. Reductive amination of the 3-aryl-2-hydroxybenzaldehyde of general formula 15 with an amine of general formula 16 in the presence of a reducing agent in a suitable solvent such as methanol, ethanol, tetrahydrofuran of dichloroethane gives the novel compounds of general Formula I ($R^3$, $R^{3a}$=H). Examples of reducing agents include hydrogen in the presence of a hydrogenation catalyst, for example palladium or platinum on carbon, sodium cyanoborohydride (for a review see Lane, C. F., Synthesis 1975, 135) or sodium triacetoxyborohydride (Abdel-Magid, A. F. et al. J. Org. Chem. 1996, 61, 3849). Alternatively, when the amine of general formula 16 is a primary amine the intermediate imine can be preformed then reduced in situ with sodium borohydride (Abdel-Magid, A. F. et al. J. Org. Chem. 1996, 61, 3849). In accordance with the preferred embodiment of this invention, the 3-aryl-2-hydroxybenzaldehyde of general formula 15 is treated with 1 to 4 equivalents of an amine of general formula 16, 1 to 3 equivalents of sodium triacetoxyborohydride and 0 to 2 equivalents of acetic acid in dichloroethane to give the novel compounds of general Formula I ($R^3$, $R^{3a}$=H). When the amine of general formula 16 is a primary amine, a solution of 3-aryl-2-hydroxybenzaldehyde of general formula 15 in methanol is treated with 1 to 4 equivalents of primary amine of general formula for a period of a few hours to a few days to preform the intermediate imine Addition of sodium borohydride then gives the novel compounds of general Formula I ($R^3$, $R^{3a}$=H).

Another aspect of the invention includes methods for the treatment of malaria. In some embodiments methods for the treatment of malaria comprise administering to a patient in need of such treatment a compound of Formula I. Such treatment may also comprise administration of a pharmaceutical composition comprising a compound of Formula I.

In some embodiments methods for treatment of malaria comprise coadministration of one or more anti-malarial agents with a compound of Formula I. Anti-malarial agents suitable for co-administration with a compound of Formula I include, for example, Amodiaquine, Arteether, Arteflene, Artemether, Artemisinin, Artesunate, Atovaquone, Chloroquine, Clindamycin, Dihydroartemisinin, Doxycycline, Halofantrine, Lumefantrine, Mefloquine, Pamaquine, Piperaquine, Primaquine, Proguanil, Pyrimethamine, Pyronaridine, Quinine, and Tafenoquine, and combinations thereof.

EXPERIMENTAL SECTION

The following examples are illustrative of how to prepare various novel active ingredients of this invention. However, said examples are merely illustrative and should not be construed as limiting the scope of the invention. All substituents are as defined above unless indicated otherwise.

General Procedures.

The HPLC/MS analyses were performed using a Hewlett Packard 1100 mass spectrometer coupled to a Hewlett Packard 1100 series HPLC utilizing a Phenomenex Kinetex XB-C18 50×4.60 mm column eluting a 1 mL/min with a solvent gradient of 70:30 A:B for 1.0 min, then 70:30 to 10:90 A:B over 6.5 min, then 10:90 A:B for 2.0 min, then 10:90 to 70:30 A:B over 0.5 min: solvent A=0.05% formic acid in water, solvent B=acetonitrile.

Proton NMR spectra were obtained with a 400 MHz Varian Unity Inova Spectrometer in chloroform-d, methanol-$d_4$ or dimethyl sulfoxide-$d_6$ and chemical shifts are reported as using the deuterium solvent as a standard and coupling constants are reported in hertz.

Intermediate 1: 8-Bromo-3,6-di-tert-butyl-3,4-dihydro-2H-benzo[e][1,3]oxazine

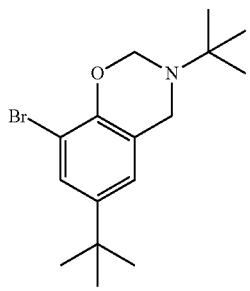 [SMILES: CC(C)(C)c1cc(Br)c2c(c1)CN(C(C)(C)C)CO2]

Step 1: 2-Bromo-4-(tert-butyl)phenol

A solution of bromine (7.18 mL, 0.14 mol) in chloroform (25 mL) was added dropwise over 2 hours to a solution of 4-tert-butyl-phenol (20 g, 0.133 mol) in 1:1 v/v chloroform: carbon tetrachloride (64 mL) at 0° C. under nitrogen until a slight red coloration persisted (approximately 1 mL of bromine solution remained). The reaction mixture was then purged with nitrogen overnight. The resulting tan solution was diluted with dichloromethane (50 mL), washed with 1% aqueous sodium thiosulfate solution (100 mL) and saturated brine (100 mL), dried ($MgSO_4$), filtered and concentrated under reduced pressure to give 2-bromo-4-(tert-butyl)phenol (30.5 g, quantitative yield) as a colorless oil.

Step 2: 8-Bromo-3,6-di-tert-butyl-3,4-dihydro-2H-benzo[e][1,3]oxazine

A mixture of paraformaldehyde (19.99 g, 0.666 mol) and tert-butylamine (70.26 mL, 0.666 mol) in isopropanol (260 mL) was heated to gentle reflux under nitrogen for 75 minutes. A solution of 2-bromo-4-(tert-butyl)phenol (30.5 g, 0.133 mol) in isopropanol (40 mL) was then added and the mixture refluxed for a further 20 hours. The cooled reaction mixture was then concentrated to afford a yellow solid. The crude product was re-crystallized from methanol (100 mL) to give 8-bromo-3,6-di-tert-butyl-3,4-dihydro-2H-benzo[e][1,3]oxazine (36.74 g, 85% yield) as a cream crystalline solid.

Analysis calculated for $C_{16}H_{24}BrNO$: C, 58.90; H, 7.41; N, 4.29, Br 24.49. found: C, 59.02; H, 7.42; N, 4.26, Br 24.87.

Intermediate 2: (5-(tert-Butyl)-2-methoxyphenyl)boronic acid

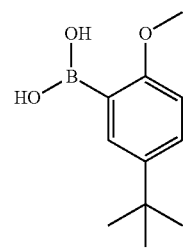

Step 1: 2-Bromo-4-(tert-butyl)-1-methoxybenzene

Iodomethane (10.0 mL, 0.161 mol) was added to a mixture of 2-bromo-4-(tert-butyl)phenol [Intermediate 1, Step 1] (29.5 g, 0.129 mol) and potassium carbonate (42.7 g, 0.309 mol) in dry acetone (400 mL) and the reaction mixture refluxed under nitrogen for 22 hours. The cooled reaction mixture was then concentrated and the residue partitioned between ethyl acetate (400 mL) and 0.3 M aqueous sodium hydroxide solution (300 mL). The organic phase was separated, washed with water (300 mL) and saturated brine (300 mL), dried ($MgSO_4$), filtered and concentrated under reduced pressure to give 2-bromo-4-(tert-butyl)-1-methoxybenzene (32.09 g, 100% yield) as a light yellow oil.

HPLC/MS $R_t$=7.47 min.

Step 2: (5-(tert-Butyl)-2-methoxyphenyl)boronic acid n-Butyllithium in hexane (2.5 M, 18.1 mL, 45.24 mmol) was added dropwise to a solution of 2-bromo-4-(tert-butyl)-1-methoxybenzene (10.0 g, 41.13 mmol) and triisopropyl borate (11.39 mL, 49.35 mmol) in tetrahydrofuran (90 mL) at −78° C. under nitrogen. The reaction mixture was stirred at −78° C. for 3 hours then allowed to warm slowly to 0° C. over 90 minutes. The reaction was then quenched by the addition of water (90 mL) and the tetrahydrofuran removed under reduced pressure. The resulting aqueous suspension was partitioned between diethyl ether (80 mL) and 1.0 M aqueous sodium hydroxide solution (100 mL). The aqueous phase was separated, cooled to 0° C. then acidified to pH 1 by the addition of concentrated hydrochloric acid. The resulting white suspension was stood at 0° C. for 15 minutes then filtered washing the solid product with water and cold hexane to give (5-(tert-butyl)-2-methoxyphenyl)boronic acid (6.349 g, 74% yield) as a white crystalline solid.

HPLC/MS $R_t$=5.04 min, m/z 209.1 (M+H$^+$).

Intermediate 3: (5-(tert-Butyl)-2-((2-methoxyethoxy)methoxy)phenyl)boronic acid

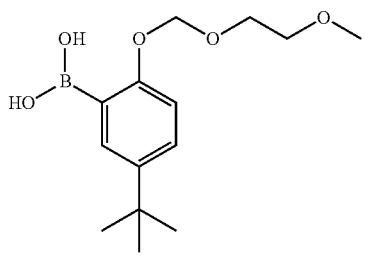 [SMILES: COCCOCOc1ccc(C(C)(C)C)cc1B(O)O]

Step 1: 2-Bromo-4-(tert-butyl)-1-((2-methoxyethoxy)methoxy)benzene

To a solution of 2-bromo-4-(tert-butyl)phenol [Intermediate 1, Step 1] (5.0 g, 21.8 mmol) and triethylamine (4.4 g, 43.5 mmol) in anhydrous dichloromethane (20 mL) at room temperature under nitrogen was added dropwise 2-methoxyethoxymethyl chloride (2.5 mL, 21.9 mmol) and the reaction mixture stirred overnight. The reaction mixture was poured into water (100 mL), the organic phase separated, dried (MgSO$_4$), filtered and concentrated under reduced pressure to give 2-bromo-4-(tert-butyl)-1-((2-methoxyethoxy)methoxy)benzene (5.0 g, 72% yield).

MS m/z 317 and 319 (M+H$^+$).

Step 2: (5-(tert-Butyl)-2-((2-methoxyethoxy)methoxy)phenyl)boronic acid n-Butyllithium in hexane (2.5 M, 4.2 mL, 10.5 mmol) was added dropwise to a solution of give 2-bromo-4-(tert-butyl)-1-((2-methoxyethoxy)methoxy)benzene (3.0 g, 9.46 mmol) and trimethyl borate (1.2 mL, 10.76 mmol) in anhydrous tetrahydrofuran (20 mL) at −78° C. under nitrogen. The reaction mixture was stirred at −78° C. for 20 minutes then at 0° C. for an additional 20 minutes. The reaction was then quenched by the addition of water (20 mL) and the mixture extracted with ether (100 mL). The organic layer was separated, dried (MgSO$_4$), filtered and concentrated under reduced pressure to give (5-(tert-butyl)-2-((2-methoxyethoxy)methoxy)phenyl)boronic acid (2.61 g, 98% yield).

MS m/z 283 (M+H$^+$).

Intermediate 4: 3-Bromo-5-(tert-butyl)-2-hydroxybenzaldehyde

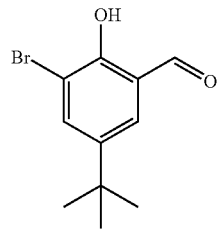

A mixture of 2-bromo-4-(tert-butyl)phenol [Intermediate 1, Step 1] (6.87 g, 30 mmol) and hexamethylenetetramine (20 g, 143 mmol) in trifluoroacetic acid (60 mL) was heated at 90° C. under nitrogen for 22 hours. The hot reaction mixture was poured into 1M aqueous hydrochloric acid (200 mL) and the mixture stirred vigorously for 6 hours. The resulting suspension was filtered to give 3-bromo-5-(tert-butyl)-2-hydroxybenzaldehyde (6.79 g, 88% yield) as a yellow solid.

HPLC/MS $R_t$=6.92 min, m/z 257.0 and 259.0 (M+H$^+$).

Intermediate 5: 5-(tert-Butyl)-2-hydroxy-4'-(trifluoromethoxy)-[1,1'-biphenyl]-3-carbaldehyde

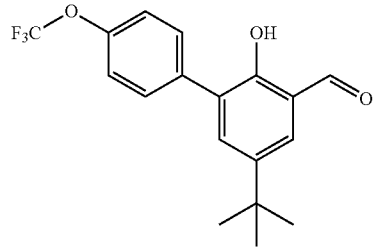 [SMILES: CC(C)(C)c1cc(C=O)c(O)c(-c2ccc(OC(F)(F)F)cc2)c1]

A solution of 3-bromo-5-(tert-butyl)-2-hydroxybenzaldehyde (Intermediate 4) (4 g, 15.56 mmol) in DME (30 mL) and water (10 mL) was purged with nitrogen for 15 minutes. Potassium carbonate (3.2 g, 23.15 mmol), 4-trifluoromethoxybenzeneboronic acid (3.2 g, 15.54 mmol) and tetrakis(triphenylphosphine)palladium(0) (0.78 g, 0.675 mmol) were added and the reaction mixture heated to reflux under nitrogen overnight. The cooled reaction mixture was then filtered through celite washing through with diethyl ether. The filtrate was dried (MgSO$_4$), filtered and concentrated under reduced pressure. The product was purified using flash chromatography on silica eluting with a solvent gradient of 0 to 100% ethyl acetate in hexanes to give 5-(tert-butyl)-2-hydroxy-4'-(trifluoromethoxy)-[1,1'-biphenyl]-3-carbaldehyde (4.5 g, 85%).

HPLC/MS m/z 339.2 (M+H$^+$).

Example 1

4-(tert-Butyl)-2-((tert-butylamino)methyl)-6-(naphthalen-1-yl)phenol hydrochloride

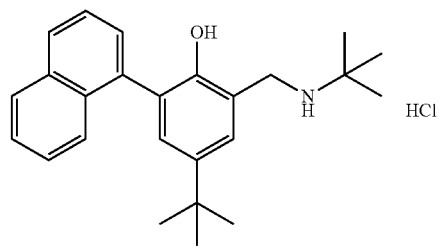 [SMILES: CC(C)(C)NCc1cc(C(C)(C)C)cc(-c2cccc3ccccc23)c1O ; Cl]

A mixture of 8-bromo-3,6-di-tert-butyl-3,4-dihydro-2H-benzo[e][1,3]oxazine (Intermediate 1) (2.0 g, 6.13 mmol), naphthalene-1-boronic acid [purchased from Frontier Scientific] (1.107 g, 6.44 mmol) and potassium carbonate (1.27 g, 9.19 mmol) in dimethoxyethane (15 mL) and water (5 mL) was purged with nitrogen for 20 minutes. Tetrakis(triphenylphosphine)palladium(0) (354 mg, 0.306 mmol) was then added and the mixture heated at 80° C. in a sealed vial for 19 hours. The cooled reaction mixture was then partitioned between ethyl acetate (80 mL) and 1M aqueous sodium hydroxide (80 mL). The organic phase was separated, washed with water (80 mL) and saturated brine (80 mL), dried (MgSO$_4$), filtered and concentrated under reduced pressure to give a brown foam. The product 3,4-dihydro-2H-benzo[e][1,3]oxazine (~6.13 mmol) was dissolved in ethanol (60 mL), 1.0 M aqueous hydrochloric acid (30 mL) added and the reaction mixture stirred at room temperature for 4 days. The reaction mixture was then concentrated under reduced pressure to remove ethanol and the resulting aqueous suspension partitioned between ethyl acetate (200 mL) and 10% w/v aqueous sodium carbonate solution (200 mL). The organic phase was separated, washed with water (200 mL) and saturated brine (200 mL), dried (MgSO$_4$), filtered and concentrated under reduced pressure to give a brown oil. The product was purified using flash chromatography on silica eluting with a solvent gradient of 0 to 40% ethyl acetate in hexanes to give the product as a light brown foam (2.35 g). The product was dissolved in absolute ethanol (40 mL), 1.0 M aqueous hydrochloric acid (18.4 mL, 18.4 mmol) added, the mixture stood for 20 minutes then concentrated under reduced pressure and the product azeotroped with absolute ethanol (3×60 mL) to give an orange foam. Diethyl ether (30 mL) and methanol (3 mL) were added and the resulting suspension stirred vigorously for 4 hours then filtered to afford 4-(tert-butyl)-2-((tert-butylamino)methyl)-6-(naphthalen-1-yl)phenol hydrochloride (1.957 g, 80% yield) as a cream solid.

HPLC/MS R$_t$=3.97 min, m/z 362.3 (M+H$^+$); analysis calculated for C$_{25}$H$_{31}$NO HCl: C, 75.45; H, 8.10; N, 3.52; Cl, 8.91. found: C, 75.35; H, 8.57; N, 3.44; Cl, 9.11.

Example 2

4-(tert-Butyl)-2-((tert-butylamino)methyl)-6-(naphthalen-2-yl)phenol hydrochloride

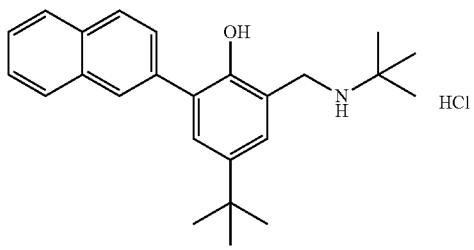 [SMILES: CC(C)(C)NCc1cc(C(C)(C)C)cc(-c2ccc3ccccc3c2)c1O ; Cl]

4-(tert-Butyl)-2-((tert-butylamino)methyl)-6-(naphthalen-2-yl)phenol hydrochloride was prepared as a cream solid using the procedure described in Example 1 from 8-bromo-3,6-di-tert-butyl-3,4-dihydro-2H-benzo[e][1,3]oxazine (Intermediate 1) and naphthalene-1-boronic acid [purchased from Frontier Scientific].

HPLC/MS R$_t$=4.17 min, m/z 362.3 (M+H$^+$); analysis calculated for C$_{25}$H$_{31}$NO HCl: C, 75.45; H, 8.10; N, 3.52; Cl, 8.91. found: C, 75.47; H, 8.00; N, 3.54; Cl, 8.91.

Example 3

2-(Benzo[d][1,3]dioxol-5-yl)-4-(tert-butyl)-6-((tert-butylamino)methyl)phenol hydrochloride

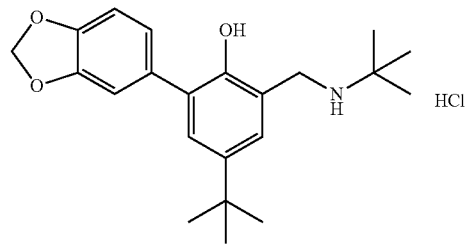 [SMILES: CC(C)(C)NCc1cc(C(C)(C)C)cc(-c2ccc3c(c2)OCO3)c1O ; Cl]

2-(Benzo[d][1,3]dioxol-5-yl)-4-(tert-butyl)-6-((tert-butylamino)methyl)phenol hydrochloride was prepared as a white solid using the procedure described in Example 1 from 8-bromo-3,6-di-tert-butyl-3,4-dihydro-2H-benzo[e][1,3]oxazine (Intermediate 1) and 3,4-(Methylenedioxy)phenylboronic acid [purchased from Frontier Scientific].

HPLC/MS R$_t$=3.13 min, m/z 356.3 (M+H$^+$).

Example 4

5-(tert-Butyl)-3-((tert-butylamino)methyl)-4'-(methylsulfonyl)-[1,1'-biphenyl]-2-ol hydrochloride

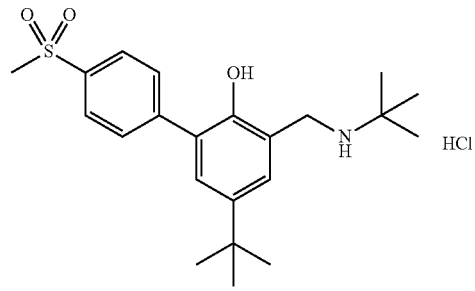 [SMILES: CC(C)(C)NCc1cc(C(C)(C)C)cc(-c2ccc(S(C)(=O)=O)cc2)c1O ; Cl]

5-(tert-Butyl)-3-((tert-butylamino)methyl)-4'-(methylsulfonyl)-[1,1'-biphenyl]-2-ol hydrochloride was prepared as a white solid using the procedure described in Example 1 from 8-bromo-3,6-di-tert-butyl-3,4-dihydro-2H-benzo[e][1,3]oxazine (Intermediate 1) and 4-(methylsulfonyl)phenylboronic acid [purchased from Frontier Scientific].

HPLC/MS R$_t$=2.83 min, m/z 390.2 (M+H$^+$); analysis calculated for C$_{22}$H$_{31}$NO$_3$S HCl: C, 59.51; H, 7.72; N, 3.15; Cl, 7.98. found: C, 59.88; H, 7.66; N, 3.13; Cl, 8.06.

Example 5

5-(tert-Butyl)-3-((tert-butylamino)methyl)-4'-(trifluoromethoxy)-[1,1'-biphenyl]-2-ol

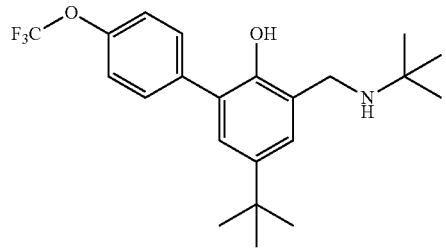 [SMILES: CC(C)(C)NCc1cc(C(C)(C)C)cc(-c2ccc(OC(F)(F)F)cc2)c1O]

5-(tert-butyl)-3-((tert-butylamino)methyl)-4'-(trifluoromethoxy)-[1,1'-biphenyl]-2-ol A solution of 5-(tert-butyl)-2-hydroxy-4'-(trifluoromethoxy)-[1,1'-biphenyl]-3-carbaldehyde (Intermediate 5) (0.7 g) and tert-butylamine (0.9 mL) in ethanol (50 mL) was refluxed for one hour, then the reaction mixture was cooled to room temperature. Sodium borohydride (0.31 g) was added slowly to the reaction and the resulting solution was stirred at 50° C. for one hour. The reaction was quenched by addition of 5% aqueous hydrochloric acid (10 mL). The desired product was extracted with ethyl acetate (30 mL), the organic layer separated, dried (MgSO$_4$), filtered and concentrated under reduced pressure to give the product (1 g). The product was re-crystallized from aqueous ethanol to afford 5-(tert-butyl)-3-((tert-butylamino)methyl)-4'-(trifluoromethoxy)-[1,1'-biphenyl]-2-ol (0.7 g).

HPLC/MS m/z=396.2 (M+H$^+$).

Example 6

3-(((3s,5s,7s)-Adamantan-1-ylamino)methyl)-5-(tert-butyl)-4'-(trifluoromethoxy)-[1,1'-biphenyl]-2-ol

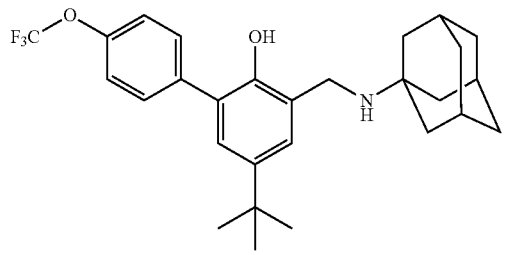 [SMILES: CC(C)(C)c1cc(CNC23CC4CC(CC(C4)C2)C3)c(O)c(-c2ccc(OC(F)(F)F)cc2)c1]

3-(((3s,5s,7s)-Adamantan-1-ylamino)methyl)-5-(tert-butyl)-4'-(trifluoromethoxy)-[1,1'-biphenyl]-2-ol was prepared as a white solid using the procedure described in Example 5 from 5-(tert-butyl)-2-hydroxy-4'-(trifluoromethoxy)-[1,1'-biphenyl]-3-carbaldehyde (Intermediate 5) and 1-adamantylamine.

HPLC/MS m/z=474.2 (M+H$^+$).

Example 7

3-((Bicyclo[2.2.1]heptan-2-ylamino)methyl)-5-(tert-butyl)-4'-(trifluoromethoxy)-[1,1'-biphenyl]-2-ol

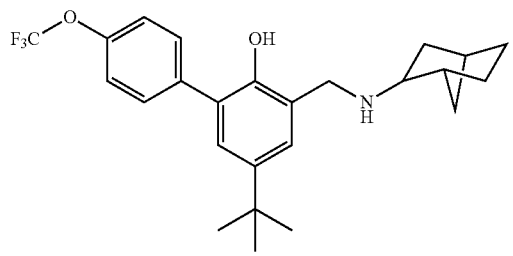 [SMILES: CC(C)(C)c1cc(CNC2CC3CCC2C3)c(O)c(-c2ccc(OC(F)(F)F)cc2)c1]

3-((Bicyclo[2.2.1]heptan-2-ylamino)methyl)-5-(tert-butyl)-4'-(trifluoromethoxy)-[1,1'-biphenyl]-2-ol was prepared as a white solid using the procedure described in Example 5 from 5-(tert-butyl)-2-hydroxy-4'-(trifluoromethoxy)-[1,1'-biphenyl]-3-carbaldehyde (Intermediate 5) and exo-2-aminonorbornane.

HPLC/MS m/z=434.2 (M+H$^+$); analysis calculated for $C_{25}H_{30}F_3NO_2$: C, 69.26; H, 6.98; N, 3.23; F, 13.15. found: C, 69.20; H, 6.99; N, 3.19; F, 13.10.

Example 8

5-(tert-Butyl)-4'-(trifluoromethoxy)-3-(((2,4,4-trimethylpentan-2-yl)amino)methyl)-[1,1'-biphenyl]-2-ol hydrochloride

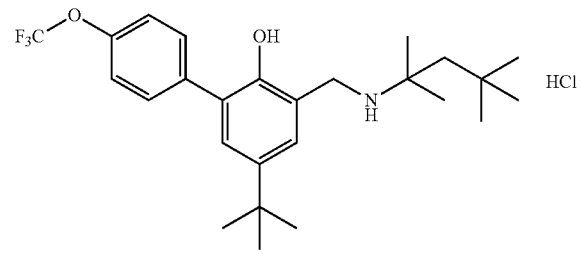 [SMILES: CC(C)(C)CC(C)(C)NCc1cc(C(C)(C)C)cc(-c2ccc(OC(F)(F)F)cc2)c1O ; Cl]

5-(tert-Butyl)-4'-(trifluoromethoxy)-3-(((2,4,4-trimethylpentan-2-yl)amino)methyl)-[1,1'-biphenyl]-2-ol hydrochloride was prepared as a white solid using the procedure described in Example 5 from 5-(tert-butyl)-2-hydroxy-4'-(trifluoromethoxy)-[1,1'-biphenyl]-3-carbaldehyde (Intermediate 5) and 2,4,4-trimethyl-2-pentanamine.

HPLC/MS m/z=452.3 (M+H$^+$).

Example 9

5-(tert-Butyl)-3-((cyclobutylamino)methyl)-4'-(trifluoromethoxy)-[1,1'-biphenyl]-2-ol hydrochloride

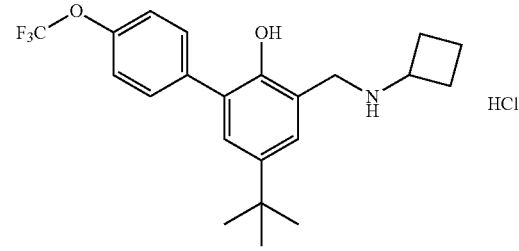 [SMILES: CC(C)(C)c1cc(CNC2CCC2)c(O)c(-c2ccc(OC(F)(F)F)cc2)c1 ; Cl]

A mixture of 5-(tert-butyl)-2-hydroxy-4'-(trifluoromethoxy)-[1,1'-biphenyl]-3-carbaldehyde (Intermediate 5) (1.0 g, 2.96 mmol) and cyclobutylamine (1.01 mL, 11.83 mmol) in absolute ethanol (10 mL) was stirred at 70° C. for 1 hour. The reaction mixture was cooled to room temperature, sodium borohydride (0.22 g, 5.81 mmol) added and the reaction mixture stirred for 30 minutes the quenched by the addition of 6.0 M aqueous hydrochloric acid (3.0 mL). The reaction mixture was concentrated under reduced pressure to remove ethanol and the residue partitioned between ethyl acetate and saturated aqueous sodium hydrogen carbonate. The organic phase was separated, washed with saturated brine, dried (MgSO$_4$), filtered and concentrated under reduced pressure. The product was dissolved in ethanol (5 mL), concentrated hydrochloric acid in ethanol (0.5 mL)

added, the mixture concentrated under reduced pressure and the resulting solid recrystallized from ethyl acetate to give 5-(tert-butyl)-3-((cyclobutylamino)methyl)-4'-(trifluoromethoxy)-[1,1'-biphenyl]-2-ol hydrochloride (0.79 g, 62% yield) as a white crystalline solid.

HPLC/MS $R_t$=6.03 min, m/z 394.4.4 (M+H$^+$).

Example 10

5-(tert-Butyl)-3-((isopropylamino)methyl)-4'-(trifluoromethoxy)-[1,1'-biphenyl]-2-ol hydrochloride

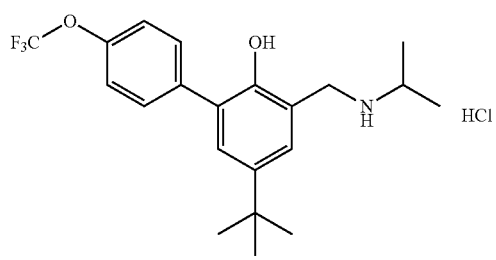 [SMILES: CC(C)NCc1cc(C(C)(C)C)cc(-c2ccc(OC(F)(F)F)cc2)c1O ; Cl]

5-(tert-Butyl)-3-((isopropylamino)methyl)-4'-(trifluoromethoxy)-[1,1'-biphenyl]-2-ol hydrochloride was prepared as a white solid using the procedure described in Example 9 from 5-(tert-butyl)-2-hydroxy-4'-(trifluoromethoxy)-[1,1'-biphenyl]-3-carbaldehyde (Intermediate 5) and isopropylamine.

HPLC/MS $R_t$=5.77 min, m/z 382.4 (M+H$^+$).

Example 11

5-(tert-Butyl)-3-((cyclohexylamino)methyl)-4'-(trifluoromethoxy)-[1,1'-biphenyl]-2-ol hydrochloride

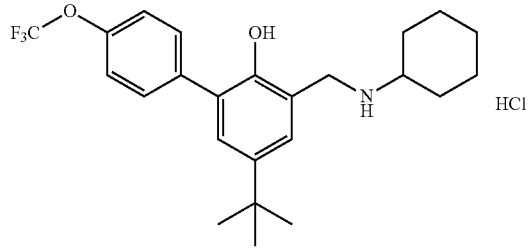 [SMILES: CC(C)(C)c1cc(CNC2CCCCC2)c(O)c(-c2ccc(OC(F)(F)F)cc2)c1 ; Cl]

5-(tert-Butyl)-3-((cyclohexylamino)methyl)-4'-(trifluoromethoxy)-[1,1'-biphenyl]-2-ol hydrochloride was prepared as a white solid using the procedure described in Example 9 from 5-(tert-butyl)-2-hydroxy-4'-(trifluoromethoxy)-[1,1'-biphenyl]-3-carbaldehyde (Intermediate 5) and cyclohexylamine.

HPLC/MS $R_t$=6.22 min, m/z 422.4 (M+H$^+$).

Example 12

5-(tert-Butyl)-3-(piperidin-1-ylmethyl)-4'-(trifluoromethoxy)-[1,1'-biphenyl]-2-ol hydrochloride

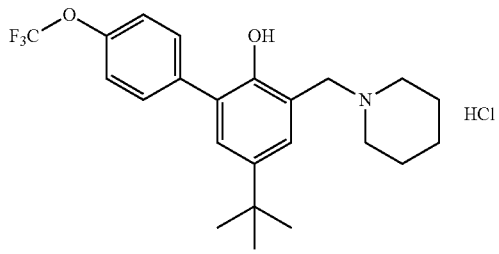 [SMILES: CC(C)(C)c1cc(CN2CCCCC2)c(O)c(-c2ccc(OC(F)(F)F)cc2)c1 ; Cl]

5-(tert-Butyl)-3-(piperidin-1-ylmethyl)-4'-(trifluoromethoxy)-[1,1'-biphenyl]-2-ol hydrochloride was prepared as a white solid using the procedure described in Example 9 from 5-(tert-butyl)-2-hydroxy-4'-(trifluoromethoxy)-[1,1'-biphenyl]-3-carbaldehyde (Intermediate 5) and piperidine.

HPLC/MS $R_t$=6.03 min, m/z 408.4 (M+H$^+$).

Example 13

5-(tert-Butyl)-3-((tert-butylamino)methyl)-4'-phenoxy-[1,1'-biphenyl]-2-ol hydrochloride

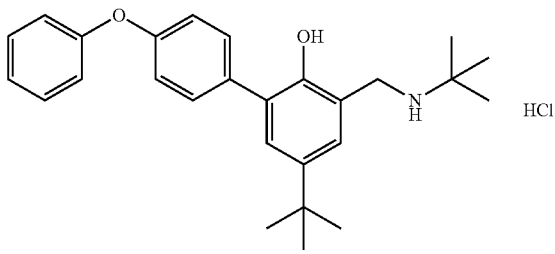 [SMILES: CC(C)(C)NCc1cc(C(C)(C)C)cc(-c2ccc(Oc3ccccc3)cc2)c1O ; Cl]

Step 1: 5-(tert-Butyl)-2-hydroxy-4'-phenoxy-[1,1'-biphenyl]-3-carbaldehyde was prepared as an orange oil using the procedure described in Intermediate 5 from 3-bromo-5-(tert-butyl)-2-hydroxybenzaldehyde (Intermediate 4) and 4-phenoxyphenylboronic acid.

Step 2: 5-(tert-Butyl)-3-((tert-butylamino)methyl)-4'-phenoxy-[1,1'-biphenyl]-2-ol hydrochloride was prepared as a white solid using the procedure described in Example 9 from 5-(tert-butyl)-2-hydroxy-4'-phenoxy-[1,1'-biphenyl]-3-carbaldehyde and tert-butylamine.

Example 14

5-(tert-Butyl)-3-((tert-butylamino)methyl)-2',4'-bis(trifluoromethyl)-[1,1'-biphenyl]-2-ol hydrochloride

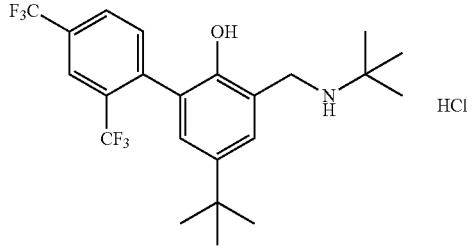 [SMILES: CC(C)(C)NCc1cc(C(C)(C)C)cc(-c2ccc(C(F)(F)F)cc2C(F)(F)F)c1O ; Cl]

Step 1: 5-(tert-Butyl)-2-hydroxy-2',4'-bis(trifluoromethyl)-[1,1'-biphenyl]-3-carbaldehyde was prepared as an orange oil using the procedure described in Intermediate 5 from 3-bromo-5-(tert-butyl)-2-hydroxybenzaldehyde (Intermediate 4) and 2,4-bis(trifluoromethyl)phenylboronic acid.

Step 2: 5-(tert-Butyl)-3-((tert-butylamino)methyl)-4'-phenoxy-[1,1'-biphenyl]-2-ol hydrochloride was prepared as a white solid using the procedure described in Example 9 from 5-(tert-butyl)-2-hydroxy-2',4'-bis(trifluoromethyl)-[1,1'-biphenyl]-3-carbaldehyde and tert-butylamine.

Example 15

5-(tert-Butyl)-3-(((1-methylcyclohexyl)amino)methyl)-4'-(trifluoromethoxy)-[1,1'-biphenyl]-2-ol hydrochloride

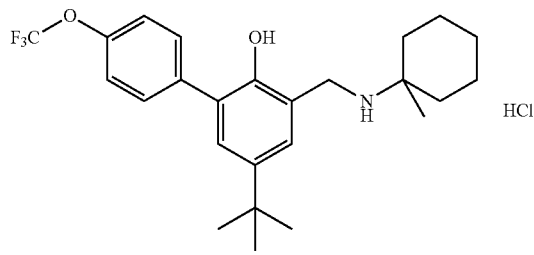 [SMILES: CC1(NCc2cc(C(C)(C)C)cc(-c3ccc(OC(F)(F)F)cc3)c2O)CCCCC1 ; Cl]

5-(tert-Butyl)-3-(((1-methylcyclohexyl)amino)methyl)-4'-(trifluoromethoxy)-[1,1'-biphenyl]-2-ol hydrochloride was prepared as a white solid using the procedure described in Example 9 from 5-(tert-butyl)-2-hydroxy-4'-(trifluoromethoxy)-[1,1'-biphenyl]-3-carbaldehyde (Intermediate 5) and 1-methyl-1-cyclohexanamine.
HPLC/MS $R_t$=6.69 min, m/z 436.4 (M+H$^+$).

Example 16

5-(tert-Butyl)-3-((tert-butylamino)methyl)-3',5'-bis(trifluoromethyl)-[1,1'-biphenyl]-2-ol hydrochloride

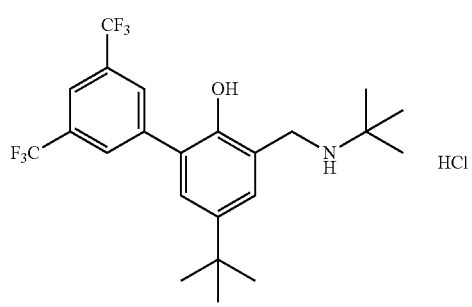 [SMILES: CC(C)(C)NCc1cc(C(C)(C)C)cc(-c2cc(C(F)(F)F)cc(C(F)(F)F)c2)c1O ; Cl]

Step 1: 5-(tert-Butyl)-2-hydroxy-3',5'-bis(trifluoromethyl)-[1,1'-biphenyl]-3-carbaldehyde was prepared as an orange oil using the procedure described in Intermediate 5 from 3-bromo-5-(tert-butyl)-2-hydroxybenzaldehyde (Intermediate 4) and 3,5-bis(trifluoromethyl)phenylboronic acid.

Step 2: 5-(tert-Butyl)-3-((tert-butylamino)methyl)-4'-phenoxy-[1,1'-biphenyl]-2-ol hydrochloride was prepared as a white solid using the procedure described in Example 9 from 5-(tert-butyl)-2-hydroxy-3',5'-bis(trifluoromethyl)-[1,1'-biphenyl]-3-carbaldehyde and tert-butylamine.

Example 17

5-(tert-Butyl)-3-(((1-methylcyclopentyl)amino)methyl)-4'-(trifluoromethoxy)-[1,1'-biphenyl]-2-ol hydrochloride

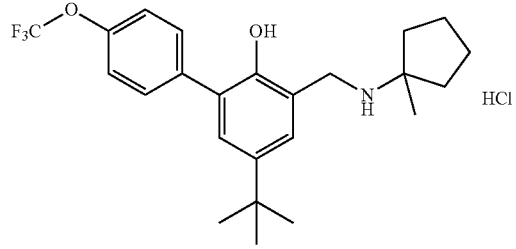 [SMILES: CC1(NCc2cc(C(C)(C)C)cc(-c3ccc(OC(F)(F)F)cc3)c2O)CCCC1 ; Cl]

5-(tert-Butyl)-3-(((1-methylcyclopentyl)amino)methyl)-4'-(trifluoromethoxy)-[1,1'-biphenyl]-2-ol hydrochloride was prepared as a white solid using the procedure described in Example 9 from 5-(tert-butyl)-2-hydroxy-4'-(trifluoromethoxy)-[1,1'-biphenyl]-3-carbaldehyde (Intermediate 5) and 1-methylcyclopentan-1-amine.

Example 18

5-(tert-Butyl)-3-(((1-methylcyclobutyl)amino)methyl)-4'-(trifluoromethoxy)-[1,1'-biphenyl]-2-ol hydrochloride

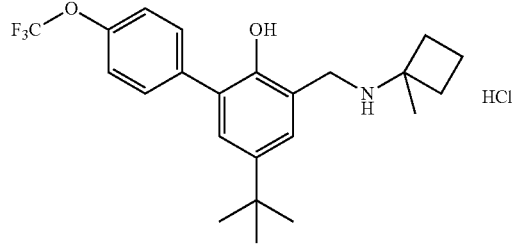 [SMILES: CC1(NCc2cc(C(C)(C)C)cc(-c3ccc(OC(F)(F)F)cc3)c2O)CCC1 ; Cl]

5-(tert-Butyl)-3-(((1-methylcyclobutyl)amino)methyl)-4'-(trifluoromethoxy)-[1,1'-biphenyl]-2-ol hydrochloride was prepared as a white solid using the procedure described in Example 9 from 5-(tert-butyl)-2-hydroxy-4'-(trifluoromethoxy)-[1,1'-biphenyl]-3-carbaldehyde (Intermediate 5) and 1-Methylcyclobutanamine HPLC/MS m/z 408 (M+H$^+$).

Example 19

5-(tert-Butyl)-3-((tert-butylamino)methyl)-3',4'-dichloro-[1,1'-biphenyl]-2-ol hydrochloride

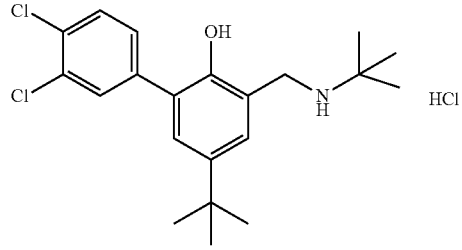 [SMILES: CC(C)(C)NCc1cc(C(C)(C)C)cc(-c2ccc(Cl)c(Cl)c2)c1O ; Cl]

Step 1: 5-(tert-Butyl)-3',4'-dichloro-2-hydroxy-[1,1'-biphenyl]-3-carbaldehyde was prepared as a yellow solid using the procedure described in Intermediate 5 from 3-bromo-5-(tert-butyl)-2-hydroxybenzaldehyde (Intermediate 4) and 3,4-dichlorophenylboronic acid.

Step 2: 5-(tert-Butyl)-3-((tert-butylamino)methyl)-3',4'-dichloro-[1,1'-biphenyl]-2-ol hydrochloride was prepared as a white solid using the procedure described in Example 9 from 5-(tert-butyl)-3',4'-dichloro-2-hydroxy-[1,1'-biphenyl]-3-carbaldehyde and tert-butylamine.

Example 20

5-(tert-Butyl)-3-((tert-butylamino)methyl)-2',4'-dichloro-[1,1'-biphenyl]-2-ol hydrochloride

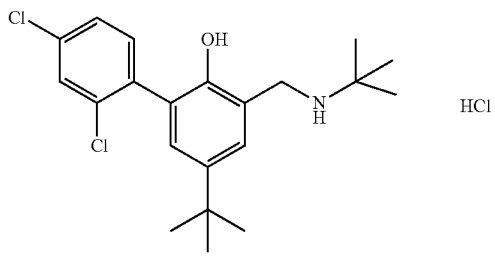 [SMILES: CC(C)(C)NCc1cc(C(C)(C)C)cc(-c2ccc(Cl)cc2Cl)c1O ; Cl]

Step 1: 5-(tert-Butyl)-2',4'-dichloro-2-hydroxy-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 2,4-dichlorophenylboronic acid.

Step 2: 5-(tert-Butyl)-3-((tert-butylamino)methyl)-2',4'-dichloro-[1,1'-biphenyl]-2-ol hydrochloride was prepared as a gray solid using the procedure described in Example 9 from 5-(tert-butyl)-2',4'-dichloro-2-hydroxy-[1,1'-biphenyl]-3-carbaldehyde and tert-butylamine.

HPLC/MS $R_t$=5.25 min, m/z 380.2 and 382.3 (M+H$^+$).

Example 21

5-(tert-Butyl)-3-((tert-butylamino)methyl)-2'-chloro-4'-(trifluoromethyl)-[1,1'-biphenyl]-2-ol hydrochloride

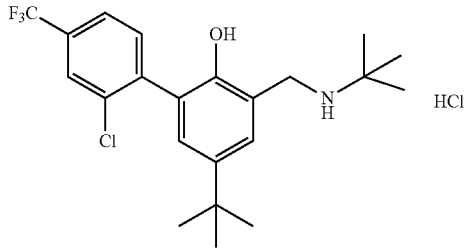 [SMILES: CC(C)(C)NCc1cc(C(C)(C)C)cc(-c2ccc(C(F)(F)F)cc2Cl)c1O ; Cl]

Step 1: 5-(tert-Butyl)-2'-chloro-2-hydroxy-4'-(trifluoromethyl)-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 2-chloro-4-(trifluoromethyl)phenylboronic acid.

Step 2: 5-(tert-Butyl)-3-((tert-butylamino)methyl)-2'-chloro-4'-(trifluoromethyl)-[1,1'-biphenyl]-2-ol hydrochloride was prepared as a white solid using the procedure described in Example 9 from 5-(tert-butyl)-2'-chloro-2-hydroxy-4'-(trifluoromethyl)-[1,1'-biphenyl]-3-carbaldehyde and tert-butylamine.

Example 22

5-(tert-Butyl)-3-((tert-butylamino)methyl)-4'-(trifluoromethyl)-[1,1'-biphenyl]-2-ol hydrochloride

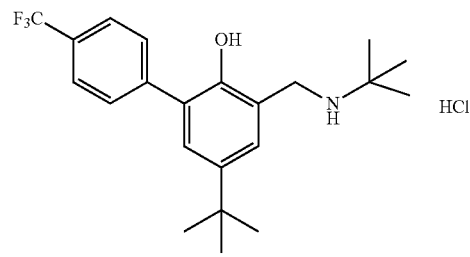 [SMILES: CC(C)(C)NCc1cc(C(C)(C)C)cc(-c2ccc(C(F)(F)F)cc2)c1O ; Cl]

Step 1: 5-(tert-Butyl)-2-hydroxy-4'-(trifluoromethyl)-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 4-(trifluoromethyl)phenylboronic acid.

Step 2: 5-(tert-Butyl)-3-((tert-butylamino)methyl)-4'-(trifluoromethyl)-[1,1'-biphenyl]-2-ol hydrochloride was prepared as a white solid using the procedure described in Example 9 from 5-(tert-butyl)-2-hydroxy-4'-(trifluoromethyl)-[1,1'-biphenyl]-3-carbaldehyde and tert-butylamine.

HPLC/MS $R_t$=5.25 min, m/z 380.4 (M+H$^+$).

Example 23

5-(tert-Butyl)-3-((tert-butylamino)methyl)-4'-chloro-3'-(trifluoromethyl)-[1,1'-biphenyl]-2-ol hydrochloride

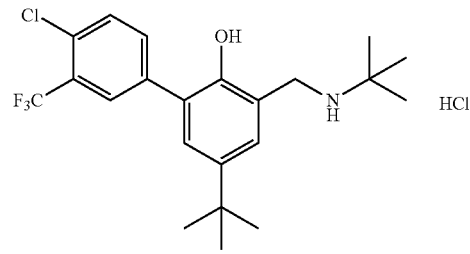 [SMILES: CC(C)(C)NCc1cc(C(C)(C)C)cc(-c2ccc(Cl)c(C(F)(F)F)c2)c1O ; Cl]

Step 1: 5-(tert-Butyl)-4'-chloro-2-hydroxy-3'-(trifluoromethyl)-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 4-chloro-3-(trifluoromethyl)phenylboronic acid.

Step 2: 5-(tert-Butyl)-3-((tert-butylamino)methyl)-4'-chloro-3'-(trifluoromethyl)-[1,1'-biphenyl]-2-ol hydrochloride was prepared as a white solid using the procedure described in Example 9 from 5-(tert-butyl)-4'-chloro-2-hydroxy-3'-(trifluoromethyl)-[1,1'-biphenyl]-3-carbaldehyde and tert-butylamine. HPLC/MS $R_t$=7.41 min, m/z 414.1 and 416.1 (M+H$^+$).

Example 24

5-(tert-Butyl)-3-((tert-butylamino)methyl)-3'-chloro-4'-fluoro-[1,1'-biphenyl]-2-ol hydrochloride

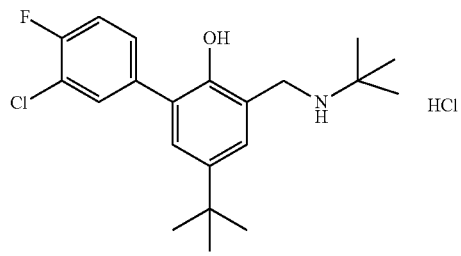 [SMILES: CC(C)(C)NCc1cc(C(C)(C)C)cc(-c2ccc(F)c(Cl)c2)c1O ; Cl]

Step 1: 5-(tert-Butyl)-3'-chloro-4'-fluoro-2-hydroxy-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 3-chloro-4-fluorophenylboronic acid.

Step 2: 5-(tert-Butyl)-3-((tert-butylamino)methyl)-3'-chloro-4'-fluoro-[1,1'-biphenyl]-2-ol hydrochloride was prepared as a white solid using the procedure described in Example 9 from 5-(tert-Butyl)-3'-chloro-4'-fluoro-2-hydroxy-[1,1'-biphenyl]-3-carbaldehyde and tert-butylamine.

Example 25

5-(tert-Butyl)-3',4'-dichloro-3-(((1-methylcyclobutyl)amino)methyl)-[1,1'-biphenyl]-2-ol

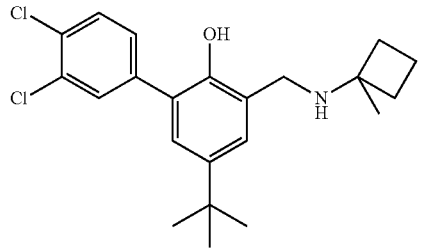 [SMILES: CC1(NCc2cc(C(C)(C)C)cc(-c3ccc(Cl)c(Cl)c3)c2O)CCC1]

5-(tert-Butyl)-3',4'-dichloro-3-(((1-methylcyclobutyl)amino)methyl)-[1,1'-biphenyl]-2-ol was prepared as a white solid using the procedure described in Example 5 from 5-(tert-butyl)-3',4'-dichloro-2-hydroxy-[1,1'-biphenyl]-3-carbaldehyde (from Example 19, Step 1) and 1-methylcyclobutylamine.

HPLC/MS m/z 392.2 (M+H$^+$).

Example 26

5-(tert-Butyl)-3-((tert-butylamino)methyl)-4'-chloro-3'-fluoro-[1,1'-biphenyl]-2-ol hydrochloride

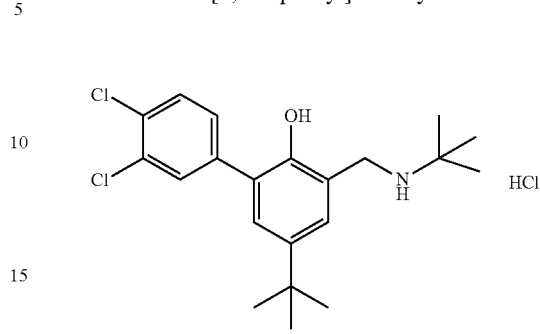

Step 1: 5-(tert-Butyl)-4'-chloro-3'-fluoro-2-hydroxy-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 4-chloro-3-fluorophenylboronic acid.

Step 2: 5-(tert-Butyl)-3-((tert-butylamino)methyl)-4'-chloro-3'-fluoro-[1,1'-biphenyl]-2-ol hydrochloride was prepared as a white solid using the procedure described in Example 9 from 5-(tert-butyl)-4'-chloro-3'-fluoro-2-hydroxy-[1,1'-biphenyl]-3-carbaldehyde and tert-butylamine.

HPLC/MS $R_t$=5.85 min, m/z 364.4 and 366.4 (M+H$^+$).

Example 27

5-(tert-Butyl)-3-((tert-butylamino)methyl)-3'-chloro-4'-(trifluoromethyl)-[1,1'-biphenyl]-2-ol

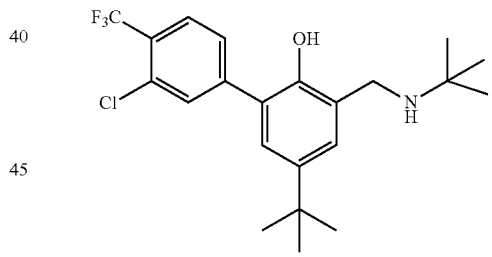

Step 1: 5-(tert-Butyl)-3'-chloro-2-hydroxy-4'-(trifluoromethyl)-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 3-chloro-4-(trifluoromethyl)phenylboronic acid.

Step 2: 5-(tert-Butyl)-3-((tert-butylamino)methyl)-3'-chloro-4'-(trifluoromethyl)-[1,1'-biphenyl]-2-ol To a solution of 5-(tert-butyl)-3'-chloro-2-hydroxy-4'-(trifluoromethyl)-[1,1'-biphenyl]-3-carbaldehyde (674 mg, 1.89 mmol) and tert-butylamine (138 mg, 1.89 mmol) in dichloroethane (10 mL) at room temperature under nitrogen was added sodium triacetoxyborohydride (1.20 g, 5.67 mmol) and the reaction mixture stirred for 28 hours. The reaction mixture was partitioned between dichloromethane (100 mL) and saturated brine (50 mL). The organic phase was separated, dried (MgSO$_4$), filtered and concentrated under reduced pressure to give a white solid (741 mg). The product was re-crystallized from diethyl ether to give 5-(tert-Butyl)-3-((tert-butylamino)methyl)-3'-chloro-4'-(trifluoromethyl)-[1,1'-biphenyl]-2-ol (340 mg, 43% yield) as a white solid. HPLC/MS R$_t$=7.13 min, m/z 414.1 and 416.1 (M+H$^+$).

Example 28

5-(tert-Butyl)-3-((tert-butylamino)methyl)-4'-fluoro-3'-(trifluoromethyl)-[1,1'-biphenyl]-2-ol acetic acid salt

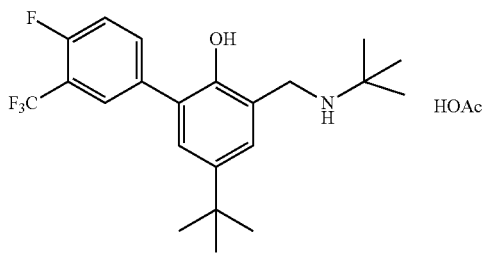 [SMILES: CC(C)(C)NCc1cc(C(C)(C)C)cc(-c2ccc(F)c(C(F)(F)F)c2)c1O ; "HOAc"]

Step 1: 5-(tert-Butyl)-4'-fluoro-2-hydroxy-3'-(trifluoromethyl)-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 4-fluoro-3-(trifluoromethyl)phenylboronic acid.

Step 2: 5-(tert-Butyl)-3-((tert-butylamino)methyl)-4'-chloro-3'-fluoro-[1,1'-biphenyl]-2-ol acetic acid salt was prepared as a white solid using the procedure described in Example 27, Step 2 from 5-(tert-butyl)-4'-fluoro-2-hydroxy-3'-(trifluoromethyl)-[1,1'-biphenyl]-3-carbaldehyde and tert-butylamine HPLC/MS R$_t$=7.75 min, m/z 398.1 (M+H$^+$).

Example 29

5-(tert-Butyl)-3-((tert-butylamino)methyl)-3'-(trifluoromethyl)-[1,1'-biphenyl]-2-ol

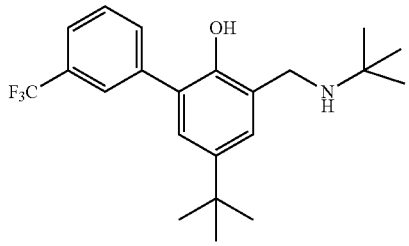 [SMILES: CC(C)(C)NCc1cc(C(C)(C)C)cc(-c2cccc(C(F)(F)F)c2)c1O]

Step 1: 5-(tert-Butyl)-2-hydroxy-3'-(trifluoromethyl)-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 3-(trifluoromethyl)phenylboronic acid.

Step 2: 5-(tert-Butyl)-3-((tert-butylamino)methyl)-3'-(trifluoromethyl)-[1,1'-biphenyl]-2-ol was prepared as a white solid using the procedure described in Example 27, Step 2 from 5-(tert-butyl)-2-hydroxy-3'-(trifluoromethyl)-[1,1'-biphenyl]-3-carbaldehyde and tert-butylamine HPLC/MS R$_t$=6.64 min, m/z 380.2 (M+H$^+$).

Example 30

5-(tert-Butyl)-3-((tert-butylamino)methyl)-3',4'-difluoro-[1,1'-biphenyl]-2-ol acetic acid salt

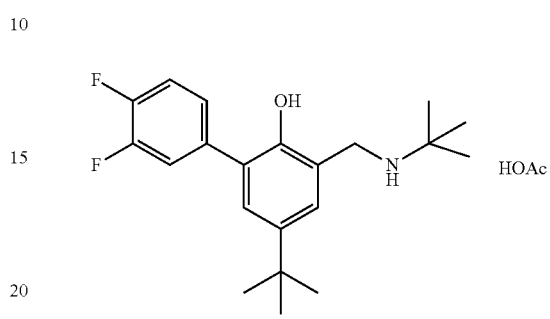

Step 1: 5-(tert-Butyl)-3',4'-difluoro-2-hydroxy-[1,1'-biphenyl]-3-carbaldehyde was prepared as a yellow oil using the procedure described in Intermediate 5 from 3-bromo-5-(tert-butyl)-2-hydroxybenzaldehyde (Intermediate 4) and 3,4-difluorophenylboronic acid.

Step 2: 5-(tert-Butyl)-3-((tert-butylamino)methyl)-3',4'-difluoro-[1,1'-biphenyl]-2-ol acetic acid salt was prepared as a white solid using the procedure described in Example 27, Step 2 5-(tert-butyl)-2-hydroxy-3'-(trifluoromethyl)-[1,1'-biphenyl]-3-carbaldehyde and tert-butylamine HPLC/MS R$_t$=6.84 min, m/z 348.1 (M+H$^+$).

Example 31

3-((tert-Butylamino)methyl)-3',4'-dichloro-5-(trifluoromethyl)-[1,1'-biphenyl]-2-ol hydrochloride

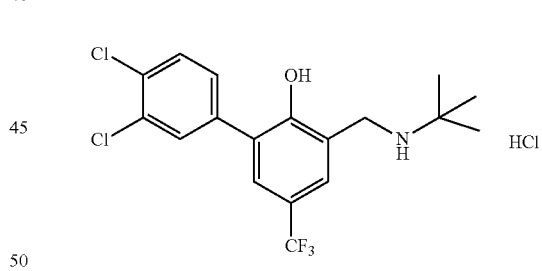

Step 1: 3',4'-Dichloro-5-(trifluoromethyl)-[1,1'-biphenyl]-2-ol was prepared as a yellow oil using the procedure described in Intermediate 5 from 2-bromo-4-(trifluoromethyl)phenol (Tetrahedron 2003, 59, 6545) and 3,4-dichlorophenylboronic acid.

Step 2: A solution of 3',4'-dichloro-5-(trifluoromethyl)-[1,1'-biphenyl]-2-ol (100 mg, 0.326 mmol), 37% aqueous formaldehyde (0.03 ml, 0.403 mmol) and tert-butylamine (0.042 g, 0.574 mmol) in isobutyl alcohol (40 mL) was heated to 100° C. under nitrogen for 22 hours. The cooled reaction mixture was concentrated under reduced pressure and the residue partitioned between ethyl acetate and saturated aqueous sodium bicarbonate solution. The organic phase was separated, dried (MgSO$_4$), filtered and concentrated under reduced pressure to give a yellow oil (0.121 g). The product was dissolved in ethanol, concentrated hydrochloric acid in ethanol added, the mixture concentrated under reduced pressure and the resulting solid re-crystallized from hexanes with a minimum amount of ethyl acetate to give 3-((tert-butylamino)methyl)-3',4'-dichloro-5-(trifluoromethyl)-[1,1'-biphenyl]-2-ol hydrochloride (130 mg, 93% yield) as a white crystalline solid.

Example 32

5-Butyl-3-((tert-butylamino)methyl)-3',4'-dichloro-[1,1'-biphenyl]-2-ol hydrochloride

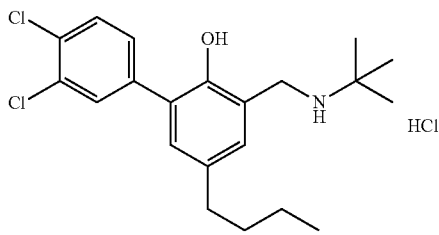 [SMILES: CCCCc1cc(CNC(C)(C)C)c(O)c(-c2ccc(Cl)c(Cl)c2)c1 ; Cl]

5-Butyl-3-((tert-butylamino)methyl)-3',4'-dichloro-[1,1'-biphenyl]-2-ol hydrochloride was prepared as a white solid using the procedure described in Example 9 from 5-butyl-3',4'-dichloro-2-hydroxy-[1,1'-biphenyl]-3-carbaldehyde and tert-butylamine.

HPLC/MS m/z 380.4 and 382.4 (M+H$^+$).

Example 33

3-((tert-Butylamino)methyl)-3',4'-dichloro-5-(3-phenylpropyl)-[1,1'-biphenyl]-2-ol hydrochloride

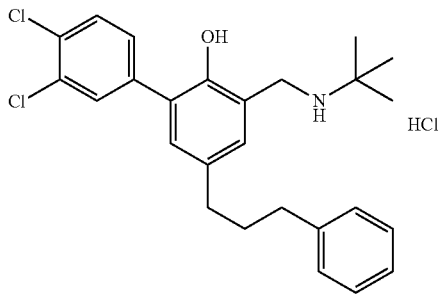 [SMILES: CC(C)(C)NCc1cc(CCCc2ccccc2)cc(-c2ccc(Cl)c(Cl)c2)c1O ; Cl]

3-((tert-Butylamino)methyl)-3',4'-dichloro-5-(3-phenylpropyl)-[1,1'-biphenyl]-2-ol hydrochloride was prepared as a white solid using the procedure described in Example 9 from 3',4'-dichloro-2-hydroxy-5-(3-phenylpropyl)-[1,1'-biphenyl]-3-carbaldehyde and tert-butylamine.

HPLC/MS m/z 442 (M+H$^+$).

Example 34

3-((tert-Butylamino)methyl)-3',4'-dichloro-5-(4-chlorophenethyl)-[1,1'-biphenyl]-2-ol hydrochloride

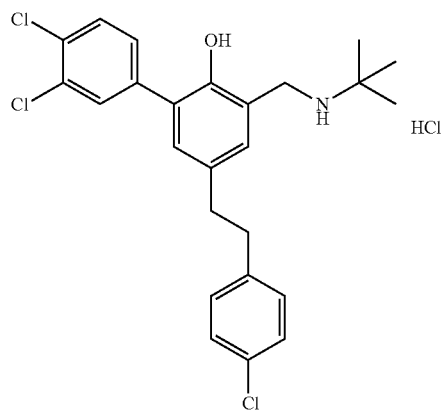 [SMILES: CC(C)(C)NCc1cc(CCc2ccc(Cl)cc2)cc(-c2ccc(Cl)c(Cl)c2)c1O ; Cl]

3-((tert-Butylamino)methyl)-3',4'-dichloro-5-(4-chlorophenethyl)-[1,1'-biphenyl]-2-ol hydrochloride was prepared as a white solid using the procedure described in Example 9 from 3',4'-dichloro-5-(4-chlorophenethyl)-2-hydroxy-[1,1'-biphenyl]-3-carbaldehyde and tert-butylamine.

HPLC/MS m/z 462.4 and 464.4 (M+H$^+$).

Example 35

3-((tert-Butylamino)methyl)-3',4'-dichloro-5-(3-(4-(trifluoromethyl)phenyl)propyl)-[1,1'-biphenyl]-2-ol hydrochloride

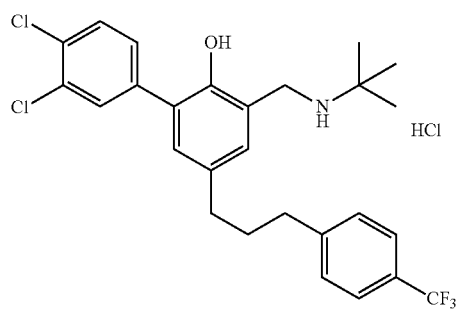 [SMILES: CC(C)(C)NCc1cc(CCCc2ccc(C(F)(F)F)cc2)cc(-c2ccc(Cl)c(Cl)c2)c1O ; Cl]

3-((tert-Butylamino)methyl)-3',4'-dichloro-5-(3-(4-(trifluoromethyl)phenyl)propyl)-[1,1'-biphenyl]-2-ol hydrochloride was prepared as a white solid using the procedure described in Example 9 from 3',4'-dichloro-2-hydroxy-5-(3-(4-(trifluoromethyl)phenyl)propyl)-[1,1'-biphenyl]-3-carbaldehyde and tert-butylamine.

HPLC/MS m/z 510.5 (M+H$^+$).

Example 36

3-((tert-Butylamino)methyl)-3',4'-dichloro-5-(4-(4-chlorophenyl)butyl)-[1,1'-biphenyl]-2-ol hydrochloride

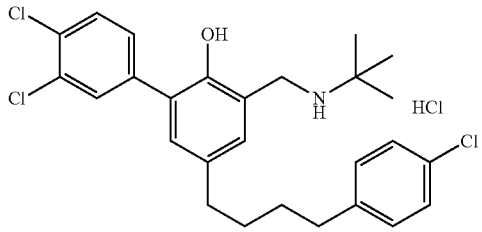 [SMILES: CC(C)(C)NCc1cc(CCCCc2ccc(Cl)cc2)cc(-c2ccc(Cl)c(Cl)c2)c1O ; Cl]

3-((tert-Butylamino)methyl)-3',4'-dichloro-5-(4-(4-chlorophenyl)butyl)-[1,1'-biphenyl]-2-ol hydrochloride was prepared as a white solid using the procedure described in Example 9 from 3',4'-dichloro-5-(4-(4-chlorophenyl)butyl)-2-hydroxy-[1,1'-biphenyl]-3-carbaldehyde and tert-butylamine.

HPLC/MS m/z 490.3 and 492.6 (M+H$^+$).

Example 37

3-((tert-Butylamino)methyl)-3',4'-dichloro-5-(trifluoromethoxy)-[1,1'-biphenyl]-2-ol hydrochloride

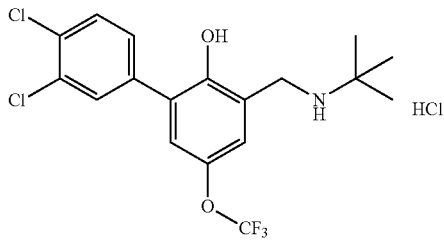 [SMILES: CC(C)(C)NCc1cc(OC(F)(F)F)cc(-c2ccc(Cl)c(Cl)c2)c1O ; Cl]

3-((tert-Butylamino)methyl)-3',4'-dichloro-5-(trifluoromethoxy)-[1,1'-biphenyl]-2-ol hydrochloride was prepared as a white solid using the procedure described in Example 9 from 3',4'-dichloro-2-hydroxy-5-(trifluoromethoxy)-[1,1'-biphenyl]-3-carbaldehyde and tert-butylamine.

HPLC/MS m/z 408 and 410 (M+H$^+$).

Example 38

5-(Benzyloxy)-3-((tert-butylamino)methyl)-3',4'-dichloro-[1,1'-biphenyl]-2-ol hydrochloride

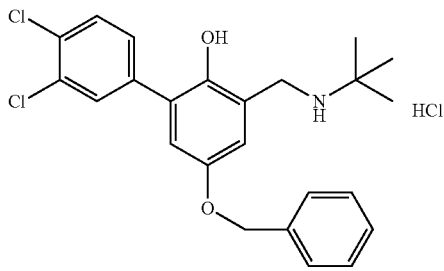 [SMILES: CC(C)(C)NCc1cc(OCc2ccccc2)cc(-c2ccc(Cl)c(Cl)c2)c1O ; Cl]

5-(Benzyloxy)-3-((tert-butylamino)methyl)-3',4'-dichloro-[1,1'-biphenyl]-2-ol hydrochloride was prepared as a white solid using the procedure described in Example 9 from 5-(benzyloxy)-3',4'-dichloro-2-hydroxy-[1,1'-biphenyl]-3-carbaldehyde and tert-butylamine.

HPLC/MS m/z 430 (M+H$^+$).

Example 39

5'-((tert-Butylamino)methyl)-3'',4,4''-trichloro-[1,1':3',1''-terphenyl]-4'-ol hydrochloride

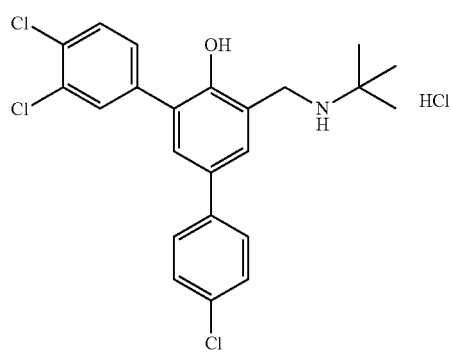 [SMILES: CC(C)(C)NCc1cc(-c2ccc(Cl)cc2)cc(-c2ccc(Cl)c(Cl)c2)c1O ; Cl]

Step 1: 3',4'-Dichloro-2-hydroxy-[1,1'-biphenyl]-3-carbaldehyde was prepared from 3-bromosalicylaldehyde and 3,4-dichlorophenylboronic acid using the same procedure described in Intermediate 5.

Step 2: 5-Bromo-3',4'-dichloro-2-hydroxy-[1,1'-biphenyl]-3-carbaldehyde

To a solution of 3',4'-dichloro-2-hydroxy-[1,1'-biphenyl]-3-carbaldehyde (400 mg, 1.5 mmol) and sodium acetate (185 mg, 1.5 mmol) in acetic acid (20 mL), bromine (100 uL, 1.5 mmol) was added slowly. The resulted solution was stirred overnight. The reaction mixture was then concentrated under reduced pressure. The residue was dissolved in ethyl acetate (20 mL), washed with 5% aqueous sodium thiosulfate, the organic layer dried (MgSO$_4$), filtered and concentrated under reduced pressure to give 5-bromo-3',4'-dichloro-2-hydroxy-[1,1'-biphenyl]-3-carbaldehyde.

Step 3: 3,4,4''-Trichloro-6'-hydroxy-[1,1':3',1''-terphenyl]-5'-carbaldehyde was prepared from 5-bromo-3',4'-dichloro-2-hydroxy-[1,1'-biphenyl]-3-carbaldehyde and 4-chlorophenylboronic acid using the same procedure described in Intermediate 5.

Step 4: 5'-((tert-Butylamino)methyl)-3'',4,4''-trichloro-[1,1':3',1''-terphenyl]-4'-ol hydrochloride was prepared from 3,4,4''-trichloro-6'-hydroxy-[1,1':3',1''-terphenyl]-5'-carbaldehyde and tert-butylamine using the same procedure described in Example 5.

HPLC/MS m/z=434.1 (M+H$^+$).

Example 40

5'-((tert-Butylamino)methyl)-3,3",4,4"-tetrachloro-[1,1':3',1"-terphenyl]-4'-ol hydrochloride

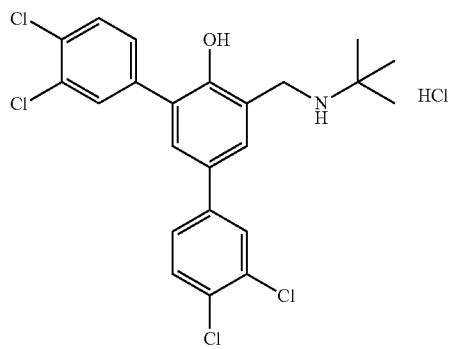 [SMILES: CC(C)(C)NCc1cc(-c2ccc(Cl)c(Cl)c2)cc(-c2ccc(Cl)c(Cl)c2)c1O ; Cl]

Step 1: 3,3",4,4"-Tetrachloro-4'-hydroxy-[1,1':3',1"-terphenyl]-5'-carbaldehyde was prepared using the procedure described in Intermediate 5 from 3,5-dibromosalicylaldehyde and 3,4-chlorophenylboronic acid.

Step 2: 5'-((tert-Butylamino)methyl)-3,3",4,4"-tetrachloro-[1,1':3',1"-terphenyl]-4'-ol hydrochloride was prepared as a white solid using the procedure described in Example 5 from 3,3",4,4"-tetrachloro-4'-hydroxy-[1,1':3',1"-terphenyl]-5'-carbaldehyde and tert-butylamine.

Example 41

5'-((tert-Butylamino)methyl)-3,3"-dichloro-4,4"-bis(trifluoromethyl)-[1,1':3',1"-terphenyl]-4'-ol

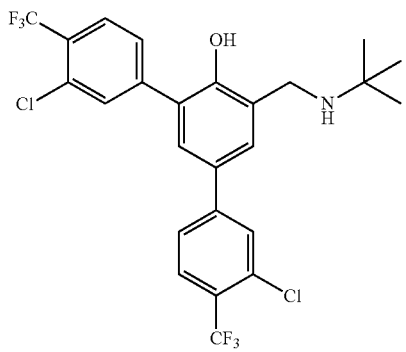 [SMILES: CC(C)(C)NCc1cc(-c2ccc(C(F)(F)F)c(Cl)c2)cc(-c2ccc(C(F)(F)F)c(Cl)c2)c1O]

Step 1: 3,3"-Dichloro-4'-hydroxy-4,4"-bis(trifluoromethyl)-[1,1':3',1"-terphenyl]-5'-carbaldehyde was prepared using the procedure described in Intermediate 5 from 3,5-dibromosalicylaldehyde and 3-chloro-4-(trifluoromethyl)phenylboronic acid.

Step 2: 5'-((tert-Butylamino)methyl)-3,3"-dichloro-4,4"-bis(trifluoromethyl)-[1,1':3',1"-terphenyl]-4'-ol was prepared as a white solid using the procedure described in Example 5 from 3,3"-dichloro-4'-hydroxy-4,4"-bis(trifluoromethyl)-[1,1':3',1"-terphenyl]-5'-carbaldehyde and tert-butylamine.

Example 42

5'-((tert-Butylamino)methyl)-4-chloro-3-(trifluoromethyl)-[1,1':3',1"-terphenyl]-4'-ol hydrochloride

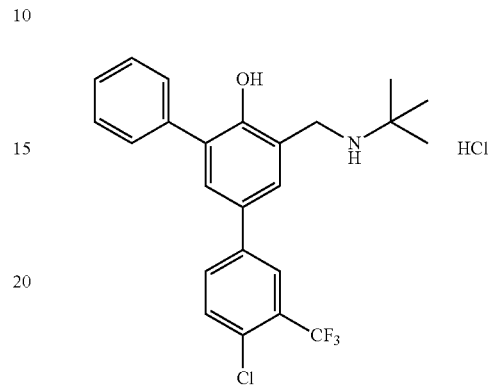

Step 1: 3-(tert-Butyl)-8-phenyl-3,4-dihydro-2H-benzo[e][1,3]oxazine

To a mixture of 2-phenylphenol (17.0 g, 0.1 mol) and paraformaldehyde (15.0 g, 0.5 mol) in isopropanol (100 mL) was added tert-butylamine (36.5 g, 0.5 mol) dropwise. The resulting reaction mixture was refluxed under nitrogen overnight. The cooled reaction mixture was then concentrated under reduced pressure to give a yellow oil. The yellow oil was dissolved in ethyl acetate to form a solution which was washed with water, dried over anhydrous sodium sulfate, filtered and concentrated under reduced pressure to afford 3-(tert-butyl)-8-phenyl-3,4-dihydro-2H-benzo[e][1,3]oxazine (30 g) as yellow oil.

HPLC/MS $R_t$=12.65 min, m/z 256 (M+H$^+$ of hydrolyzed product).

Step 2: 6-Bromo-3-(tert-butyl)-8-phenyl-3,4-dihydro-2H-benzo[e][1,3]oxazine

To a solution of 3-(tert-butyl)-8-phenyl-3,4-dihydro-2H-benzo[e][1,3]oxazine (9.420 g, 77.09 mmol) in acetonitrile (100 mL) was added dropwise bromine (1.8 mL, 1.0 equiv) at 5-10° C. After the addition, the mixture was stirred at 3-5° C. for 130 min. The resulting reaction mixture was allowed to stir at room temperature for 24 hours. To the reaction mixture was added water (200 mL) and the resulting mixture was concentrated under reduced pressure to remove most of the acetonitrile. The aqueous mixture was extracted with ethyl acetate and the combined organic layer was washed with water, dried (Na$_2$SO$_4$), filtered and concentrated under reduced pressure to give a yellow solid. The solid was dissolved in ethanol and treated with 37% HCl (3.65 g). The resulting mixture was concentrated to removed ethanol to give the product which was crystallized from MTBE-EtOH to give 6-bromo-3-(tert-butyl)-8-phenyl-3,4-dihydro-2H-benzo[e][1,3]oxazine (3.118 g).

HPLC/MS $R_t$=14.44 min, m/z 334 (M+H$^+$ of hydrolyzed product).

Step 3: 5'-((tert-Butylamino)methyl)-4-chloro-3-(trifluoromethyl)-[1,1':3',1"-terphenyl]-4'-ol hydrochloride A mixture of 6-bromo-3-(tert-butyl)-8-phenyl-3,4-dihydro-2H-benzo[e][1,3]oxazine (0.578 g, 1.68 mmol), 4-chloro-3-(trifluoromethyl)phenylboronic acid [purchased from Frontier Scientific] (0.376 g, 1.0 equiv), and potassium carbonate (0.926 g, 6.70 mmol, 4.0 equiv) in 2-methoxyethyl ether (10 mL) and water (2 mL) was purged with nitrogen for 20 minutes. Tetrakis(triphenylphosphine)Pd (0) (58.1 mg, 0.05 mmol, 3 mol %) was added and the resulting mixture was heated at 65-76° C. for 2 hours. Additional tetrakis(triphenylphosphine)Pd (0) (0.111 g, 0.096 mmol, 0.057 mol %) was added followed by 4-chloro-3-(trifluoromethyl)phenylboronic acid (0.368 g, 1.64 mmol, 0.98 equiv). The resulting mixture was heated at 75° C. for 1 hour. The cooled reaction mixture was filtered through a pad of silica gel and rinsed with ethyl acetate. The filtrate was concentrated to give a dark oil which was purified by column chromatography to afford the product as a yellow solid (0.347 g). The solid was dissolved in ethanol and 37% hydrochloric acid (0.154 g, 2 equiv) added. The resulting mixture was concentrated to give a pale yellow solid which was slurried in MTBE. The product was collected by filtration and dried at 40° C. under vacuum to furnish 5'-((tert-butylamino)methyl)-4-chloro-3-(trifluoromethyl)-[1,1':3',1"-terphenyl]-4'-ol hydrochloride (0.291 g) as an off-white solid.

HPLC/MS $R_t$=12.19 min, m/z 434 (M+H$^+$).

Example 43

3-((tert-Butylamino)methyl)-5-(6-(trifluoromethyl)pyridin-3-yl)-[1,1'-biphenyl]-2-ol hydrochloride

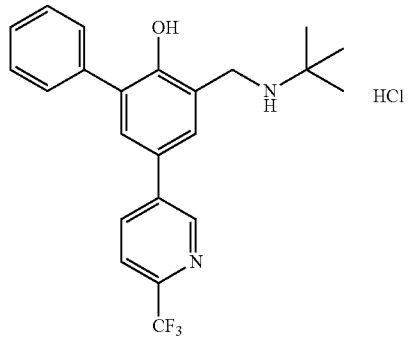 [SMILES: CC(C)(C)NCc1cc(-c2ccc(C(F)(F)F)nc2)cc(-c2ccccc2)c1O ; Cl]

3-((tert-Butylamino)methyl)-5-(6-(trifluoromethyl)pyridin-3-yl)-[1,1'-biphenyl]-2-ol hydrochloride A mixture of 6-bromo-3-(tert-butyl)-8-phenyl-3,4-dihydro-2H-benzo[e][1,3]oxazine (from Example 42, Step 2) (0.611 g, 1.77 mmol), 2-(trifluoromethyl)pyridine-5-boronic acid (0.507 g, 1.5 equiv), and potassium carbonate (0.979 g, 7.1 mmol, 4 equiv) in 2-methoxyethyl ether (10 mL) and water (2 mL) was purged with nitrogen for 20 minutes. Tetrakis(triphenylphosphine)Pd (0) (0.102 g, 5 mol %) was added and the resulting mixture was heated at 60-69° C. for 1 hour. Additional tetrakis(triphenylphosphine)Pd (0) (55 mg, 0.048 mmol, 2.7 mol %) was added followed by 2-(trifluoromethyl)pyridine-5-boronic acid (0.123 g, 0.644 mmol). The resulting mixture was heated at 69° C. for 30 minutes. The cooled reaction mixture was concentrated and the resulting residue was purified by column chromatograph to give an oil (0.420 g). The oil was dissolved in ethanol, and 37% HCl (0.207 g) added. The resulting mixture was concentrated to give an oil which was treated with MTBE. The product was collected by filtration and rinsed with MTBE to give 3-((tert-butylamino)methyl)-5-(6-(trifluoromethyl)pyridin-3-yl)-[1,1'-biphenyl]-2-ol hydrochloride (0.240 g) as a white solid.

HPLC/MS $R_t$=10.56 min, m/z 401 (M+H$^+$).

Example 44

5-(Benzofuran-2-yl)-3-((tert-butylamino)methyl)-[1,1'-biphenyl]-2-ol

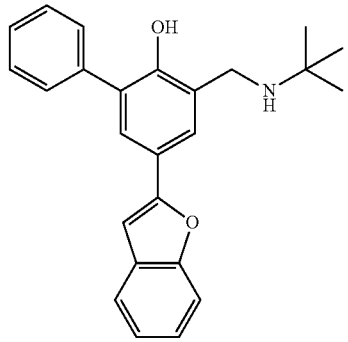 [SMILES: CC(C)(C)NCc1cc(-c2cc3ccccc3o2)cc(-c2ccccc2)c1O]

Step 3: 5-(Benzofuran-2-yl)-3-((tert-butylamino)methyl)-[1,1'-biphenyl]-2-ol A mixture of 6-bromo-3-(tert-butyl)-8-phenyl-3,4-dihydro-2H-benzo[e][1,3]oxazine (from Example 42, Step 2) (0.552 g, 1.6 mmol), benzofuran-2-ylboronic acid (0.387 g, 1.5 equiv), and potassium carbonate (0.885 g, 4 equiv) in 2-methoxyethyl ether (10 mL) and water (2 mL) was purged with nitrogen for 20 minutes. Tetrakis(triphenylphosphine)Pd (0) (82 mg, 0.073 mmol, 4.5 mol %) was added and the resulting mixture was heated at 51-62° C. for 1.5 hours. To the reaction mixture, additional benzofuran-2-ylboronic acid (0.173 g, 1.07 mmol) was added. The resulting mixture was allowed to heat at 60-62° C. overnight. The cooled reaction mixture was concentrated and the resulting residue was purified by column chromatography to give 5-(benzofuran-2-yl)-3-((tert-butylamino)methyl)-[1,1'-biphenyl]-2-ol (0.315 g).

HPLC/MS $R_t$=11.61 min, m/z 372 (M+H$^+$).

Example 45

3-((tert-Butylamino)methyl)-3',4'-dichloro-5-(6-(trifluoromethyl)pyridin-3-yl)-[1,1'-biphenyl]-2-ol hydrochloride

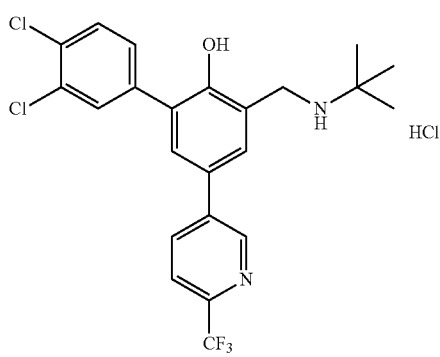 [SMILES: CC(C)(C)NCc1cc(-c2ccc(C(F)(F)F)nc2)cc(-c2ccc(Cl)c(Cl)c2)c1O ; Cl]

Step 1: 8-Bromo-3-(tert-butyl)-3,4-dihydro-2H-benzo[e][1,3]oxazine

To a mixture of 2-bromophenol (10.0 g, 57.8 mmol, 1.0 equiv), paraformaldehyde (8.67 g, 5 equiv) in isopropanol (80 mL) was added tert-butylamine (21.1 g, 5 equiv) dropwise. The resulting reaction mixture was stirred at 67-70° C. under nitrogen for 1.5 hours. The reaction mixture was then cooled to room temperature and concentrated under reduced pressure to give a yellow oil. The yellow oil was purified by column chromatography to give 8-bromo-3-(tert-butyl)-3,4-dihydro-2H-benzo[e][1,3]oxazine (9 g) as yellow oil.
HPLC/MS $R_t$=1.09 min, m/z 258 (M+H$^+$ of hydrolyzed product).

Step 2: 3-(tert-Butyl)-8-(3,4-dichlorophenyl)-3,4-dihydro-2H-benzo[e][1,3]oxazine A mixture of 8-bromo-3-(tert-butyl)-3,4-dihydro-2H-benzo[e][1,3]oxazine (0.46 g, 1.71 mmol), potassium carbonate (0.945 g, 4.0 equiv), 3,4-dichlorophenylboronic acid (0.489 g, 1.5 equiv), and tetrakis(triphenylphosphine)Pd (0) (63 mg, 3.2 mol %) was heated at 53-64° C. for 3 hours, then at 80-87° C. for 2.5 hours. To the mixture was added additional 3,4-dichlorophenylboronic acid (0.2 g) and the resulting mixture was heated at 80-87° C. overnight. Upon cooling to room temperature, the reaction mixture was concentrated. The crude product was purified by column chromatography to give 3-(tert-butyl)-8-(3,4-dichlorophenyl)-3,4-dihydro-2H-benzo[e][1,3]oxazine (0.313 g) as yellow oil.
HPLC/MS $R_t$=8.97 min, m/z 324 (M+H$^+$ of hydrolyzed product).

Step 3: 6-Bromo-3-(tert-butyl)-8-(3,4-dichlorophenyl)-3,4-dihydro-2H-benzo[e][1,3]oxazine To a solution of 3-(tert-butyl)-8-(3,4-dichlorophenyl)-3,4-dihydro-2H-benzo[e][1,3]oxazine (4.09 g, 12.21 mmol) in acetonitrile (130 mL) was added dropwise bromine (0.63 mL, 1.0 equiv) at 2-3° C. Upon completion of the addition, the resulting mixture was stirred at 2-20° C. for 5 hours. The batch was filtered and rinsed with acetonitrile. The filtrate was concentrated to give a yellow solid (5.316 g). The solid was treated with ethyl acetate and filtered to give 6-bromo-3-(tert-butyl)-8-(3,4-dichlorophenyl)-3,4-dihydro-2H-benzo[e][1,3]oxazine (0.767 g) as pale yellow solid.
HPLC/MS $R_t$=11.66 min, m/z 402 (M+H$^+$ of hydrolyzed product).

Step 4: 3-((tert-Butylamino)methyl)-3',4'-dichloro-5-(6-(trifluoromethyl)pyridine-3-yl)-[1,1'-biphenyl]2-ol hydrochloride A mixture of 6-bromo-3-(tert-butyl)-8-(3,4-dichlorophenyl)-3,4-dihydro-2H-benzo[e][1,3]oxazine (0.743 g, 1.80 mmol), (6-(trifluoromethyl)pyridin-3-yl)boronic acid (0.685 g, 2.0 equiv), and potassium carbonate (0.995 g, 4 equiv) in 2-methoxyethyl ether (32 mL) and water (6.5 mL) was purged with nitrogen for 20 minutes. Tetrakis(triphenylphosphine) Pd (0) (0.120 g, 5.8 mol %) was added and the resulting mixture was heated at 65-71° C. for 2 hours. The cooled reaction mixture was concentrated and the resulting residue was purified by column chromatograph to give 3-((tert-butylamino)methyl)-3',4'-dichloro-5-(6-(trifluoromethyl)pyridine-3-yl)-[1,1'-biphenyl]2-ol (0.128 g). The free base was dissolved in methanol, and to the solution 37% HCl was added. The resulting solid was filtered and rinsed with ethyl acetate to give 3-((tert-butylamino)methyl)-3',4'-dichloro-5-(6-(trifluoromethyl)pyridine-3-yl)-[1,1'-biphenyl]2-ol hydrochloride (0.126 g).
HPLC/MS $R_t$=12.26 min, m/z 469 (M+H$^+$).

Example 46

3-((tert-Butylamino)methyl)-5-(pyridin-4-yl)-[1,1'-biphenyl]-2-ol

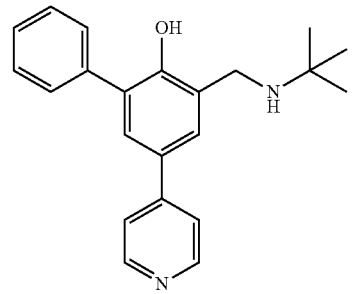 [SMILES: CC(C)(C)NCc1cc(-c2ccncc2)cc(-c2ccccc2)c1O]

Step 3: 3-((tert-Butylamino)methyl)-5-(pyridine-4-yl)-[1,1'-biphenyl]-2-ol

A mixture of 6-bromo-3-(tert-butyl)-8-phenyl-3,4-dihydro-2H-benzo[e][1,3]oxazine (from Example 42, Step 2) (0.404 g, 1.17 mmol), pyridin-4-ylboronic acid (0.288 g, 2.0 equiv), and potassium carbonate (0.647 g, 4 equiv) in isopropanol (30 mL) and water (6 mL) was purged with nitrogen for 20 minutes. Tetrakis(triphenylphosphine)Pd (0) (88 mg, 6.5 mol %) was added and the resulting mixture was heated at 55° C. for 4 hours. The cooled reaction mixture was concentrated and the resulting residue was purified by column chromatograph to give 3-((tert-butylamino)methyl)-5-(pyridine-4-yl)-[1,1'-biphenyl]-2-ol (0.126 g).
HPLC/MS $R_t$=1.07 min, m/z 333 (M+H$^+$).

Example 47

3-((tert-Butylamino)methyl)-5-(pyridin-3-yl)-[1,1'-biphenyl]-2-ol

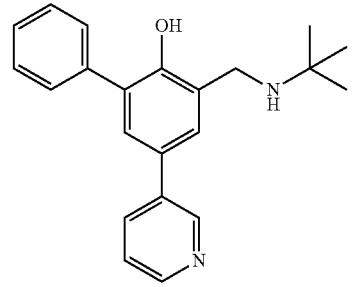 [SMILES: CC(C)(C)NCc1cc(-c2cccnc2)cc(-c2ccccc2)c1O]

Step 3: 3-((tert-Butylamino)methyl)-5-(pyridine-3-yl)-[1,1'-biphenyl]-2-ol

A mixture of 6-bromo-3-(tert-butyl)-8-phenyl-3,4-dihydro-2H-benzo[e][1,3]oxazine (from Example 42, Step 2) (0.485 g, 1.41 mmol), pyridin-3-ylboronic acid (0.346 g, 2.0 equiv), and potassium carbonate (0.777 g, 4 equiv) in isopropanol (30 mL) and water (6 mL) was purged with nitrogen for 20 minutes. Tetrakis(triphenylphosphine)Pd (0) (90 mg, 5.5 mol %) was added and the resulting mixture was heated at 55-66° C. for 3 hours. The cooled reaction mixture was concentrated and the resulting residue was purified by column chromatograph to give 3-((tert-butylamino)methyl)-5-(pyridine-3-yl)-[1,1'-biphenyl]-2-ol (0.233 g).

HPLC/MS $R_t$=1.32 min, m/z 333 (M+H$^+$).

Example 48

3-((tert-Butylamino)methyl)-5-(6-methoxypyridin-3-yl)-[1,1'-biphenyl]-2-ol tartarate

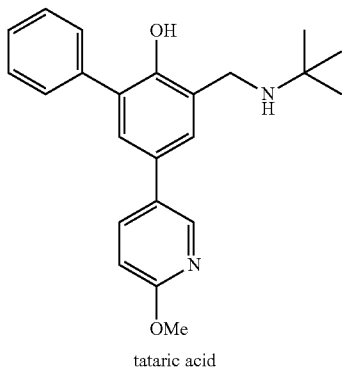 [SMILES: COc1ccc(-c2cc(CNC(C)(C)C)c(O)c(-c3ccccc3)c2)cn1]

tataric acid

Step 3: 3-((tert-Butylamino)methyl)-5-(6-methoxypyridine-3-yl)-[1,1'-biphenyl]-2-ol tartarate A mixture of 6-bromo-3-(tert-butyl)-8-phenyl-3,4-dihydro-2H-benzo[e][1,3]oxazine (0.659 g, 1.91 mmol), (6-methoxypyridin-3-yl)boronic acid (0.438 g, 1.5 equiv), and potassium carbonate (1.056 g, 4 equiv) in 2-methoxyethyl ether (10 mL) and water (2 mL) was purged with nitrogen for 20 minutes. Tetrakis(triphenylphosphine)Pd (0) (110 mg, 5 mol %) was added and the resulting mixture was heated at 61-67° C. for 2.5 hours. The cooled reaction mixture was concentrated and the resulting residue was purified by column chromatograph to give 3-((tert-butylamino)methyl)-5-(6-methoxypyridine-3-yl)-[1,1'-biphenyl]-2-ol (0.555 g) as yellow oil. 0.28 g of the oil was dissolved in ethanol and a solution of tartaric acid (0.108 g) in ethanol was added. The resulting precipitate was filtered and rinsed with ethanol to give 3-((tert-butylamino)methyl)-5-(6-methoxypyridine-3-yl)-[1,1'-biphenyl]-2-ol tartarate (100 mg).

HPLC/MS $R_t$=8.29 min, m/z 363 (M+H$^+$).

Example 49

5'-((tert-Butylamino)methyl)-4,4"-dichloro-3,3"-bis(trifluoromethyl)-[1,1':3',1"-terphenyl]-4'-ol

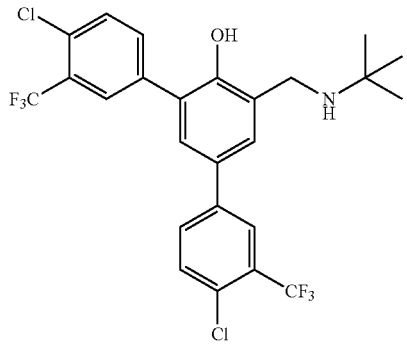 [SMILES: CC(C)(C)NCc1cc(-c2ccc(Cl)c(C(F)(F)F)c2)cc(-c2ccc(Cl)c(C(F)(F)F)c2)c1O]

Step 1: 6,8-Dibromo-3-(tert-butyl)-3,4-dihydro-2H-benzo[e][1,3]oxazine

To a mixture 2,4-dibromphenol (11.099 g, 44.06 mmol, 1.0 equiv) and paraformaldehyde (6.609 g, 5 equiv) in isopropanol (110 mL) was added tert-butylamine (16.112 g, 5 equiv) dropwise. The resulting reaction mixture was refluxed under nitrogen overnight. The reaction mixture was cooled to room temperature, filtered and the product rinsed with isopropanol and dried to give 6,8-dibromo-3-(tert-butyl)-3,4-dihydro-2H-benzo[e][1,3]oxazine (12.65 g).

HPLC/MS $R_t$=3.65 min, m/z 336 (M+H$^+$ of hydrolyzed product).

Step 2: 5'-((tert-Butylamino)methyl)-4,4"-dichloro-3,3"-bis(trifluoromethyl)-[1,1':3',1"-terphenyl]-4'-ol A mixture of 6,8-dibromo-3-(tert-butyl)-3,4-dihydro-2H-benzo[e][1,3]oxazine (0.621 g, 1.79 mmol), 4-chloro-3-(trifluoromethyl)phenylboronic acid (1.205 g, 3 equiv), and potassium carbonate (1.979 g, 4 equiv) in isopropanol (30 mL) and water (6 mL) was purged with nitrogen for 20 minutes. Tetrakis(triphenylphosphine)Pd (0) (0.095 g, 4.6 mol %) was added and the resulting mixture was heated at 69-71° C. for 2 hours. The cooled reaction mixture was concentrated and the residue was passed through a short silica gel to give a light brown solution. After removal of the solvent, the residue was crystallized from ethyl acetate to give the product (0.265 g). The product was further purified by trituration in ethyl acetate and methanol to afford 5'-((tert-butylamino)methyl)-4,4"-dichloro-3,3"-bis(trifluoromethyl)-[1,1':3',1"-terphenyl]-4'-ol (0196 g).

HPLC/MS $R_t$=14.89 min, m/z 536 (M+H$^+$).

Example 50

5-(tert-Butyl)-3-((tert-butyl(isobutyl)amino)methyl)-4'-chloro-3'-(trifluoromethyl)-[1,1'-biphenyl]-2-ol hydrochloride

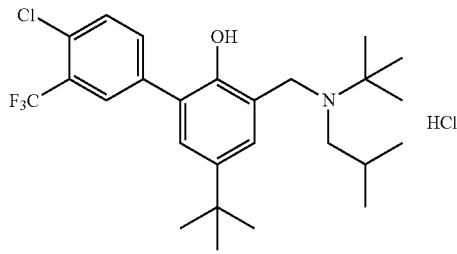 [SMILES: CC(C)CN(Cc1cc(C(C)(C)C)cc(-c2ccc(Cl)c(C(F)(F)F)c2)c1O)C(C)(C)C ; Cl]

Step 1: 3,6-di-tert-Butyl-8-(4-chloro-3-(trifluoromethyl)phenyl)-3,4-dihydro-2H-benzo[e][1,3]oxazine A mixture of 8-bromo-3,6-di-tert-butyl-3,4-dihydro-2H-benzo[e][1,3]oxazine (Intermediate 1) (3.5 g, 10.77 mmol), 4-chloro-3-(trifluoromethyl)phenylboronic acid (2.45 g, 1.0 equiv), and potassium carbonate (3.08 g, 2 equiv) in 2-methoxyethyl ether (28 mL) and water (5.2 mL) was purged with nitrogen for 20 minutes. Tetrakis(triphenylphosphine)Pd (0) (0.630 g, 5 mol %) was added and the resulting mixture was heated at 66-78° C. for 16 hours. The cooled reaction mixture was filtered through a pad of celite. The filtrate was concentrated to give a crude product which was dissolved in 20 mL of ethanol, and 2.1 g of 37% HCl was added. The resulting solid was filtered to give a white solid (3.176 g). The solid was suspended in water (30 mL), and KHCO$_3$ (0.777 g) followed by ethyl acetate (20 mL) added. The aqueous layer was extracted with ethyl acetate, and the combined organic layers were washed with water and dried (Na$_2$SO$_4$). The ethyl acetate solution was concentrated under reduced pressure and the resulting glass material was treated with methanol. The product was collected by filtration to give 3,6-di-tert-butyl-8-(4-chloro-3-(trifluoromethyl)phenyl)-3,4-dihydro-2H-benzo[e][1,3]oxazine (1.600 g).

HPLC/MS $R_t$=12.11 min, m/z 414 (M+H$^+$ of hydrolyzed product).

Step 2: 5-(tert-Butyl)-3-((tert-butyl(isobutyl)amino)methyl)-4'-chloro-3'-(trifluoromethyl)-[1,1'-biphenyl]-2-ol hydrochloride To a solution of 3,6-di-tert-butyl-8-(4-chloro-3-(trifluoromethyl)phenyl)-3,4-dihydro-2H-benzo[e][1,3]oxazine (0.737 g, 1.73 mmol) in (15 mL) was added a solution of isopropylmagnesium chloride in tetrahydrofuran (2.0 M, 1.3 mL, 2.6 mmol) at 3-12° C. The resulting mixture was stirred for 1 hour. Additional Grignard solution (0.5 mL) was added and stirring continued for 40 minutes. The reaction was quenched with aqueous ammonium chloride solution, and extracted with ethyl acetate. The combined organic layers were washed with brine, dried (Na$_2$SO$_4$) and filtered. After concentration under reduced pressure the product was crystallized from heptane to give the product (0.404 g). The free base (0.254 g) was dissolved in a mixture of ethanol and ethyl acetate and 37% HCl (0.107 g) was added. The resulting salt was collected by filtration to give 5-(tert-butyl)-3-((tert-butyl(isobutyl)amino)methyl)-4'-chloro-3'-(trifluoromethyl)-[1,1'-biphenyl]-2-ol hydrochloride (0.250 g).

HPLC/MS $R_t$=15.13 min., m/z 470 (M+H$^+$).

Example 51

5-(tert-Butyl)-3-((tert-butyl(3-phenylpropyl)amino)methyl)-4'-chloro-3'-(trifluoromethyl)-[1,1'-biphenyl]-2-ol hydrochloride

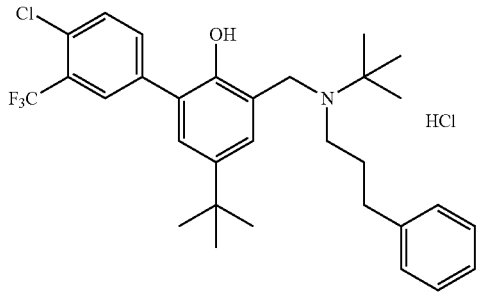 [SMILES: CC(C)(C)c1cc(CN(CCCc2ccccc2)C(C)(C)C)c(O)c(-c2ccc(Cl)c(C(F)(F)F)c2)c1 ; Cl]

5-(tert-Butyl)-3-((tert-butyl(3-phenylpropyl)amino)methyl)-4'-chloro-3'-(trifluoromethyl)-[1,1'-biphenyl]-2-ol hydrochloride To a solution of 3,6-di-tert-butyl-8-(4-chloro-3-(trifluoromethyl)phenyl)-3,4-dihydro-2H-benzo[e][1,3]oxazine (from Example 50, Step 1) (1.263 g, 2.97 mmol) in tetrahydrofuran (15 mL) was added a solution of phenylmagnesium chloride in tetrahydrofuran (1.0 M, 17.6 mL, 17.6 mmol) at 3-9° C. The reaction mixture was stirred at 3-25° C. for 2 hours. The reaction was quenched with aqueous ammonium chloride and extracted with ethyl acetate. The combined organic layers were washed with brine and water, dried (Na$_2$SO$_4$) and filtered. After concentration, the crude product was purified by column chromatography to give the product free base (0.825 g). The free base (0.256 g) was dissolved in ethyl acetate (10 mL) and ethanol (10 mL). To the solution was added 37% HCl (0.095 g), and the resulting slurry was concentrated. The residue was treated with heptane, filtered and dried under vacuum at 40° C. to give 5-(tert-butyl)-3-((tert-butyl(3-phenylpropyl)amino)methyl)-4'-chloro-3'-(trifluoromethyl)-[1,1'-biphenyl]-2-ol hydrochloride (0.226 g) as a white solid.

HPLC/MS $R_t$=16.10 min, m/z 532 (M+H$^+$).

Example 52

5-(tert-Butyl)-3-((tert-butyl(ethyl)amino)methyl)-4'-chloro-3'-(trifluoromethyl)-[1,1'-biphenyl]-2-ol hydrochloride

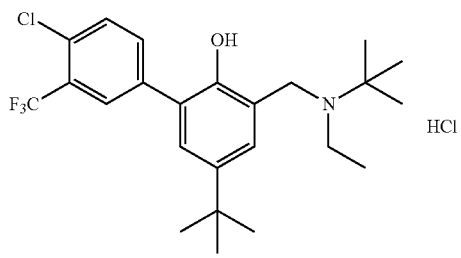 [SMILES: CCN(Cc1cc(C(C)(C)C)cc(-c2ccc(Cl)c(C(F)(F)F)c2)c1O)C(C)(C)C ; Cl]

5-(tert-Butyl)-3-((tert-butyl(ethyl)amino)methyl)-4'-chloro-3'-(trifluoromethyl)-[1,1'-biphenyl]-2-ol hydrochloride To a solution of 3,6-di-tert-butyl-8-(4-chloro-3-(trifluoromethyl)phenyl)-3,4-dihydro-2H-benzo[e][1,3]oxazine (from Example 50, Step 1) (1.293 g, 3.06 mmol) in tetrahydrofuran (15 mL) was added a solution of methylmagnesium chloride in tetrahydrofuran (3.0 M, 3.06 mL, 9.18 mmol) at 4-12° C. The reaction mixture was stirred at 4-10° C. for 30 minutes. The reaction was quenched with aqueous ammonium chloride and extracted with ethyl acetate. The combined organic layers were washed with brine and water, dried (Na$_2$SO$_4$) and filtered. After concentration under reduced pressure, a yellow oil was obtained which was crystallized from methanol to give the product free base (1.032 g). The free base (0.279 g) was dissolved in ethyl acetate (10 mL) and ethanol (10 mL). To the solution was added 37% HCl (0.125 g) and resulting slurry was concentrated. The resulting residue was treated with heptane, filtered and dried under vacuum at 40° C. to give 5-(tert-butyl)-3-((tert-butyl(ethyl)amino)methyl)-4'-chloro-3'-(trifluoromethyl)-[1,1'-biphenyl]-2-ol hydrochloride (0.276 g) as a white solid.

HPLC/MS $R_t$=13.21 min, m/z 442 (M+H$^+$).

Example 53

5-(tert-Butyl)-3-((tert-butyl(cyclohexylmethyl)amino)methyl)-4'-chloro-3'-(trifluoromethyl)-[1,1'-biphenyl]-2-ol hydrochloride

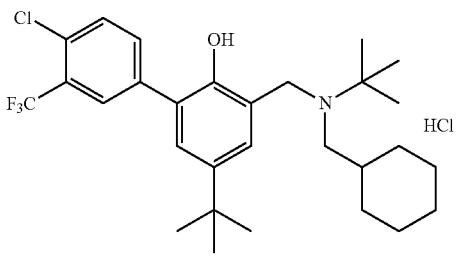 [SMILES: CC(C)(C)c1cc(CN(CC2CCCCC2)C(C)(C)C)c(O)c(-c2ccc(Cl)c(C(F)(F)F)c2)c1 ; Cl]

5-(tert-Butyl)-3-((tert-butyl(cyclohexylmethyl)amino)methyl)-4'-chloro-3'-(trifluoromethyl)-[1,1']biphenyl]-2-ol hydrochloride To a solution of 3,6-di-tert-butyl-8-(4-chloro-3-(trifluoromethyl)phenyl)-3,4-dihydro-2H-benzo[e][1,3]oxazine (from Example 50, Step 1) (1.5 g, 3.53 mmol) in tetrahydrofuran (15 mL) was added a solution of cyclohexylmagnesium chloride in diethyl ether (2.0 M, 3.95 mL, 7.9 mmol) at 3-10° C. The reaction mixture was stirred at 3-25° C. for 2 hours. The reaction was quenched with aqueous ammonium chloride, extracted with ethyl acetate. The combined organic layers were washed with brine and water, dried ($Na_2SO_4$) and filtered. After concentration under reduced pressure, the crude solid was re-crystallized from ethyl acetate to give the product free base (0.918 g). The free base (0.2 g) was dissolved in ethyl acetate (10 mL) and ethanol (10 mL). To the solution was added 37% HCl (0.078 g), and resulting slurry concentrated. The resulting residue was treated with heptane, filtered and dried under vacuum at 40° C. to give 5-(tert-butyl)-3-((tert-butyl(cyclohexylmethyl)amino)methyl)-4'-chloro-3'-(trifluoromethyl)-[1,1'-biphenyl]-2-ol hydrochloride (0.189 g) as a white solid.

HPLC/MS $R_t$=15.91 min, m/z 510 (M+H⁺).

Example 54

3-((Benzyl(tert-butyl)amino)methyl)-5-(tert-butyl)-4'-chloro-3'-(trifluoromethyl)-[1,1'-biphenyl]-2-ol hydrochloride

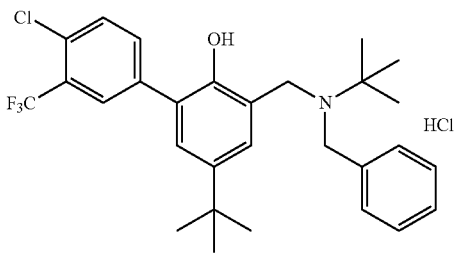 [SMILES: CC(C)(C)c1cc(CN(Cc2ccccc2)C(C)(C)C)c(O)c(-c2ccc(Cl)c(C(F)(F)F)c2)c1 ; Cl]

3-((Benzyl)(tert-butyl)amino)methyl)-5-(tert-butyl)-4'-chloro-3'-(trifluoromethyl)-[1,1'-biphenyl]-2-ol hydrochloride To a solution of 3,6-di-tert-butyl-8-(4-chloro-3-(trifluoromethyl)phenyl)-3,4-dihydro-2H-benzo[e][1,3]oxazine (from Example 50, Step 1) (1.237 g, 2.91 mmol) in tetrahydrofuran (15 mL) was added a solution of phenylmagnesium chloride in tetrahydrofuran (1.0 M, 8.73 mL, 8.73 mmol) at 3-10° C. The reaction mixture was stirred at 3-5° C. for 1 hour. The reaction was quenched with aqueous ammonium chloride and extracted with ethyl acetate. The combined organic layers were washed with brine and water, dried ($Na_2SO_4$) and filtered. After concentration under reduced pressure, the crude product was crystallized from methanol to give the product free base (1.245 g). The free base (0.253 g) was dissolved in ethyl acetate (10 mL) and ethanol (10 mL). To the solution was added 37% HCl (0.099 g), and resulting slurry was concentrated. The resulting residue was treated with heptane, filtered and dried under vacuum at 40° C. to give 3-((benzyl)(tert-butyl)amino)methyl)-5-(tert-butyl)-4'-chloro-3'-(trifluoromethyl)-[1,1'-biphenyl]-2-ol hydrochloride (0.247 g) as a white solid.

HPLC/MS $R_t$=14.89 min, m/z 504 (M+H⁺).

Example 55

5-(tert-Butyl)-3-((tert-butyl(methyl)amino)methyl)-4'-chloro-3'-(trifluoromethyl)-[1,1'-biphenyl]-2-ol hydrochloride

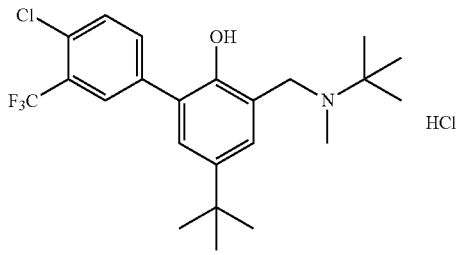 [SMILES: CN(Cc1cc(C(C)(C)C)cc(-c2ccc(Cl)c(C(F)(F)F)c2)c1O)C(C)(C)C ; Cl]

5-(tert-Butyl)-3-((tert-butyl(methyl)amino)methyl)-4'-chloro-3'-(trifluoromethyl)-[1,1'-biphenyl]-2-ol hydrochloride To a suspension of 3,6-di-tert-butyl-8-(4-chloro-3-(trifluoromethyl)phenyl)-3,4-dihydro-2H-benzo[e][1,3]oxazine (from Example 50, Step 1) (0.506 g, 1.19 mmol) in ethanol (10 mL) was added sodium borohydride (0.135 g). The resulting mixture was stirred at room temperature for 1 hour and concentrated under reduced pressure. To the residue ethyl acetate (20 mL) was added, followed by aqueous ammonium chloride. The aqueous layer was extracted with ethyl acetate and the combined organic layers was washed with water, dried ($Na_2SO_4$) and filtered. After removal of the solvent, the residue was crystallized from ethanol. The solid was collected by filtration to give the product free base (0.155 g) as an off-white solid. To the mother liquor was added 37% HCl (0.182 g), and the resulting slurry was concentrated. The residue was treated with heptane and ethyl acetate, and filtered to give 5-(tert-butyl)-3-((tert-butyl(methyl)amino)methyl)-4'-chloro-3%(trifluoromethyl)-[1,1'-biphenyl]-2-ol hydrochloride (0.321 g) as an off-white solid.

HPLC/MS $R_t$=8.41 min, m/z 428 (M+H⁺).

Example 56

4-((tert-Butylamino)methyl)-2,6-bis(4-chlorophenyl)pyridin-3-ol hydrochloride

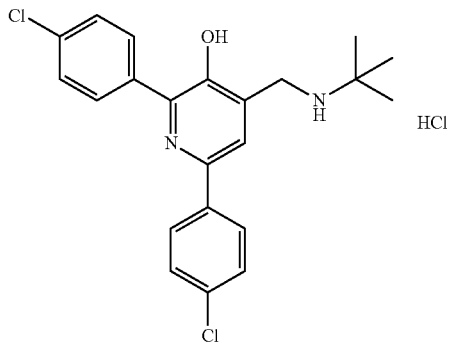 [SMILES: CC(C)(C)NCc1cc(-c2ccc(Cl)cc2)nc(-c2ccc(Cl)cc2)c1O ; Cl]

Step 1: 2-Bromo-6-iodopyridin-3-ol

To a solution of 2-bromo-3-hydroxypyridine (10 g, 57.5 mmol) and potassium carbonate (15.9 g, 114.9 mmol) in water (130 mL) was added iodine (15 g, 59.2 mmol) and the reaction mixture stirred at room temperature for 23 hours. A small amount of solid sodium metabisulfite was added to the reaction mixture. The reaction mixture was then cooled to 0° C. and acidified to pH 6 by the addition of 1 M aqueous hydrochloric acid. The resulting suspension was stirred at 0° C. for 1 hour then filtered to give 2-bromo-6-iodopyridin-3-ol (13.6 g, 79% yield) as a white solid.

HPLC/MS $R_t$=4.59 min, m/z 300 and 302 (M+H$^+$).

Step 2: 2,6-Bis(4-chlorophenyl)pyridin-3-ol

A mixture of 2-bromo-6-iodopyridin-3-ol (1.0 g, 3.335 mmol), 4-chlorophenylboronic acid (1.095 g, 7.00 mmol) and potassium carbonate (0.69 g, 5.00 mmol) in dimethoxyethane (15 mL) and water (5 mL) was purged with nitrogen for 20 minutes. Tetrakis(triphenylphosphine)palladium(0) (193 mg, 0.167 mmol) was then added and the mixture heated at 80° C. in a sealed vial for 20 hours. The cooled reaction mixture was then partitioned between ethyl acetate (80 mL) and water (80 mL). The organic phase was separated, washed with saturated brine (80 mL), dried (MgSO$_4$), filtered and concentrated under reduced pressure to give a yellow semi-solid. The product was purified using flash chromatography on silica eluting with a solvent gradient of 0 to 40% ethyl acetate in hexanes to give 2,6-bis(4-chlorophenyl)pyridin-3-ol (0.4997 g, 47% yield) as an orange syrup.

HPLC/MS $R_t$=7.67 min, m/z 316 and 318 (M+H$^+$).

Step 3: 3-(tert-Butyl)-6,8-bis(4-chlorophenyl)-3,4-dihydro-2H-pyrido[4,3-e][1,3]oxazine A mixture of paraformaldehyde (235 mg, 7.83 mmol) and tert-butylamine (0.83 mL, 7.83 mmol) in 1-propanol (5 mL) was heated at 80° C. under nitrogen for 2 hours. A solution of 2,6-bis(4-chlorophenyl)pyridin-3-ol (420 mg, 1.33 mmol) in 1-propanol (5 mL) was then added and the reaction mixture refluxed for 6 days. The reaction mixture was cooled to room temperature, stood for 24 hours and filtered to afford 3-(tert-butyl)-6,8-bis(4-chlorophenyl)-3,4-dihydro-2H-pyrido[4,3-e][1,3]oxazine (135.8 mg, 25% yield) as an orange crystalline solid.

HPLC/MS $R_t$=4.45 min, m/z 401 and 403 (M+H$^+$ of the hydrolyzed product).

Step 4: 4-((tert-Butylamino)methyl)-2,6-bis(4-chlorophenyl)pyridin-3-ol hydrochloride 1.0 M aqueous hydrochloric acid (10 mL) was added to a solution of 3-(tert-butyl)-6,8-bis(4-chlorophenyl)-3,4-dihydro-2H-pyrido[4,3-e][1,3]oxazine (203.9 mg, 0.493 mmol) in ethanol (20 mL) and the reaction mixture stirred at room temperature for 6 days. The reaction mixture was then concentrated under reduced pressure and the residue partitioned between ethyl acetate (80 mL) and 10% w/v aqueous sodium carbonate solution (80 mL). The organic phase was separated, washed with water (80 mL) and saturated brine (80 mL), dried (MgSO$_4$), filtered and concentrated under reduced pressure to give a yellow solid. The product was purified using flash chromatography on silica eluting with a solvent gradient of 0 to 30% ethyl acetate in hexanes to give the product as cream solid (166.5 mg). The product was dissolved in absolute ethanol (30 mL), 1.0 M aqueous hydrochloric acid (1.66 mL, 1.66 mmol) added, the mixture stood for 20 minutes then concentrated under reduced pressure and the product azeotroped with absolute ethanol (3×60 mL) to give a yellow syrup. The product was dissolved in methanol (1 mL), diethyl ether (8 mL) added and the product allowed to crystallize overnight to afford 4-((tert-butylamino)methyl)-2,6-bis(4-chlorophenyl)pyridin-3-ol hydrochloride (146 mg, 68% yield) as a white crystalline solid.

HPLC/MS $R_t$=4.69 min, m/z 401 and 403 (M+H$^+$); analysis calculated for $C_{22}H_{22}Cl_2N_2OHCl0.25H_2O$: C, 59.74; H, 5.36; N, 6.33; Cl, 24.05. found: C, 59.71; H, 5.32; N, 6.24; Cl, 23.82.

*Plasmodium falciparum* Assay In Vitro

The potential for antimalarial activity against *Plasmodium falciparum* was determined by measuring the incorporation of tritiated hypoxanthine into parasitized red blood cells.

Compound Preparation and Administration

Stock solutions of the test compounds and the reference drug chloroquine (CQ) (Sigma Chemicals C-6628, Lot #059H0919) were prepared in silanized glass vials with AquaSil™ (Pierce, USA) to minimize absorption of the compounds to glassware. All test compounds were dissolved in DMSO (Sigma Cat No. # D8418) to 1 mM concentration, whereas CQ was dissolved in 50% methanol at a concentration of 1.6 mg/ml (base). Stock solutions were stored at −20° C.

Continuous In Vitro Cultivation of *Plasmodium* Falciparum

*P. falciparum* Laboratory Lines

The *P. falciparum* laboratory adapted strains utilized in this project (Table 1) were in vitro cultured and routinely maintained in RPMI-1640-LPLF complete medium, which contained low concentrations of para-amino benzoic acid (0.0005 mg/L) and folic acid (0.01 mg/L).

TABLE 1

*Plasmodium falciparum* strains used in this project.

| Strain | Origin | Drug Resistance Profile |
|---|---|---|
| D6 | Sierra-Leone, Africa | Sensitive to chloroquine and pyrimethamine |
| W2 | Indochina | Resistant to chloroquine and pyrimethamine |

The low concentration of folic acid in RPMI-1640-LPLF prevents inhibition of the compound if its activity targets the parasite's folate metabolic pathway. Parasites were cultured in human red blood cells (RBCs) in vitro at 37° C. in special gas mixture (5% $O_2$, 5% $CO_2$ and 90% $N_2$) as described Trager and Jensen (1979 Science 193:673-675).

Preparation of Cultivation Medium

Base cultivation medium consisted of 10.4 g/L RPMI-1640-LPLF powder (Gibco BRL), 5.97 g/L HEPES buffer (MP Biomedicals, USA), 2.0 g/L D-glucose (BDH chemicals, Australia), 0.05 g/L hypoxanthine (Sigma, USA) and 40 mg/L gentamycin (Pfizer, Australia). The pH of the medium was adjusted to 6.9 and the solution was filtered using 0.2 μm pore size (AcroCap, Gelman Science, USA). Complete medium was prepared by adding sodium bicarbonate solution (final concentration, 0.21%) and drug-free heat-inactivated human plasma, pooled from various blood types, obtained from the Australian Red Cross Blood Service (Brisbane) (final concentration, 10%) to the base RPMI-1640-LPLF. For [$^3$H]-hypoxanthine inhibition growth assay, RPMI-1640-LPLF complete medium which lacked [$^3$H]-hypoxanthine ([$^3$H]-RPMI-1640-LPLF) was used to prevent uptake of hypoxanthine by parasites, as radioactive hypoxanthine uptake is measured as a surrogate marker of growth. All complete medium was used within three days of preparation. See DE (Para) SOP 002 for methodology.

Preparation of Red Blood Cells

Red blood cells (RBC) were required for P. falciparum parasites to proliferate in vitro. O (Rh+) type blood was obtained from the Australian Red Cross Blood Service. The RBC were washed twice in phosphate-buffered saline (PBS) and once in [$^3$H]-RPMI-1640-LPLF complete medium by centrifugation at 1,500×g for 5 min. Following the final wash, the haematocrit was measured as the percent of RBC to total culture volume. The haematocrit was adjusted to 50% by removing or adding [$^3$H]-RPMI-LPLF complete medium. See DE (Para) SOP 003 for methodology.

Continuous Cultivation of P. falciparum and Obtaining Synchronous Parasite Cultures for Drug Susceptibility Assays All P. falciparum strains were grown in RPMI-1640-LPLF complete medium at 4% haematocrit and 1% to 8% parasitaemia at 37° C. in sealed flasks in a gas mixture of 5% $O_2$, 5% $CO_2$ and 90% $N_2$ (BOC Gases, Brisbane, Australia). For drug susceptibility assays cultures were routinely synchronized when the majority of parasites (>85%) were at early trophozoite (ring) stage. Synchronization involved removing the more mature erythrocytic parasite stages by lysis, resulting in the retention only of early trophozoite (ring) stages. Synchronization was performed by re-suspending the infected red blood cell (iRBC) pellet in 5 to 10 times its volume of 5% D-sorbitol (Bacto Laboratories Pty. Ltd., Australia) for 5 min (Lambros and Vanderberg, 1979 J Parasitol 65: 418-420). The mixture was centrifuged (1,500 rpm for 5 min) and the supernatant removed. The iRBC were washed twice using PBS buffer and once using [$^3$H]-RPMI-LPLF plain medium. Following synchronization, a new culture was prepared with an initial parasitaemia of 1% in RPMI-LPLF complete medium. See DE (Para) SOP 008 for methodology.

Evaluation of In Vitro Antimalarial Activity of Test Compounds

[$^3$H]-Hypoxanthine Growth Inhibition Assay

The in vitro antimalarial activities of test compounds and reference compounds were assessed by exposing P. falciparum strains to ten serially diluted two-fold concentrations of each compound. The highest concentration of a compound on the plate ranged from 200 nM to 20,000 nM depending on its antimalarial activity. The stock solutions of the test compounds (made in DMSO) were diluted accordingly in complete [$^3$H]-media, containing 10% heat-inactivated plasma.

Parasite growth was measured by uptake of tritiated [$^3$H]-hypoxanthine into newly synthesized parasitic DNA. The [$^3$H]-hypoxanthine growth inhibition assay (Desjardins et al., 1979 Antimicrobial Agents Chemother 16: 710-718) was used to evaluate the in vitro antimalarial activity of the compounds. Briefly, synchronized parasite cultures (>90% rings, 4 to 8 h post invasion) in [$^3$H]-RPMI-LPLF complete medium with 1% parasitaemia and 2% haematocrit were exposed to the compounds at ten two-fold concentrations. Uninfected RBCs at 2% haematocrit were used as background controls. The plates were incubated in the gas mixture at 37° C. for approximately 24 h, followed by the addition of 0.2 μCi of $^3$H-hypoxanthine to each well and a further 24 h of incubation, and then frozen at −20° C. Plates were thawed and harvested using Tomtech Harvester 96 Mach III and radioactive counts were obtained using Wallac TriLux 1450 Microbeta Liquid Scintillation Counter (Perkin Elmer, USA). All assays were performed in triplicate for each strain and at least on two separate occasions.

Determination of In Vitro Inhibitory Concentrations of the Test Compounds

Tritiated hypoxanthine uptake data were analyzed in Graphpad Prism V5.0 software (GraphPad Software Inc. USA). The concentrations of the test compounds and chloroquine were transformed into logarithmic values. After subtracting the background values, the data from drug-treated wells were normalized against drug-free control wells. Non-linear regression analysis was carried out of the compound's concentration versus parasitic hypoxanthine incorporation. The in vitro antimalarial activity the compound is defined as inhibitory concentrations ($IC_{50}$) and that cause 50% inhibition of parasite growth as determined by measuring [$^3$H]-hypoxanthine incorporation.

In Vitro Antimalarial Activity of the Test Compounds

The in vitro antimalarial activities (expressed as $IC_{50}$) of the test compounds against the D6 and W2 lines of P. falciparum are shown in Table 2.

TABLE 2

In vitro antimalarial activities ($IC_{50}$) of test compounds and chloroquine against P. falciparum strains of D6 and W2.

| Example Number | D6 $IC_{50}$ (nM) | W2 $IC_{50}$ (nM) |
|---|---|---|
| Example 23 | 21 | 9 |
| Example 56 | 32 | 12 |
| Chloroquine | 12 | 133 |

Plasmodium berghei Assay In Vivo

In vivo antimalarial activity was tested in male or female Charles River CD-1 mice that were 4-5 weeks old and weighed 20-25 g They were housed in groups of 3 or 4 in standard plastic cages with wire tops, Bed-o-cob® bedding, 12 hr/day of light, and maintained at 75° F. They were fed a standard Ralston Purina mouse chow and the cages and bottles were changed twice a week. Test compounds were ground in a mortar and pestle and diluted with enough vehicle to give a volume of 10 mL/kg of mouse weight. The oral doses were prepared in 0.5% hydroxyethylcellulose (Union Carbide Corp. WP 4400)/0.1% Tween-80 (Fisher Scientific T164-500). The amount of drug was calculated on the free base weight. The mice were infected intraperitoneally on day 0 with $5 \times 10^4$ erythrocytes parasitized with Plasmodium berghei (KBG-173 strain) from a donor mouse having a parasitemia between 5-10%. On days 3, 4 and 5 the test compounds were administered bid, spaced 6 hr apart, by oral gavage to the mice. Activity was measured by survival, with full activity defined as all animals living at day 31. Partial activity is defined as days of increased survival versus the infected non-treated controls. Results of the testing is shown in Table 3. This in vivo model is a modification of the Thompson Test. For further description see Ager, A. L, Jr. Rodent Malaria Models. In Handbook of Experimental Pharmacology: Antimalarial Drugs. 1. 68/1; Peters, W., Richards, W. H. G., Eds.: Springer-Verlag: Berlin, 1984, pp. 231-33.

| Compound | Dose in mg/kg/day | Number of mice alive at day 31 | Average Days Survival (Value in parentheses for the non-treated control) |
|---|---|---|---|
| Example 5 | 256 | 7/7 | >31* (7.7) |
|  | 128 | 7/7 | >31* (7.7) |
|  | 64 | 7/7 | >31* (7.7) |
|  | 32 | 7/7 | >31* (7.7) |
|  | 16 | 7/7 | >31* (7.7) |
|  | 8 | 7/7 | >31* (9.0) |
|  | 4 | 3/7 | >19.3 (9.0) |
| Example 16 | 32 | 7/7 | >31* (8.0) |
|  | 16 | 7/7 | >31* (8.0) |
|  | 8 | 7/7 | >31* (8.0) |
|  | 4 | 6/7 | >17 (8.0) |
|  | 2 | 3/7 | >20.5 (8.0) |
| Example 18 | 32 | 7/7 | >31* (7.6) |
|  | 16 | 7/7 | >31* (7.6) |
|  | 8 | 7/7 | >31* (7.6) |
|  | 4 | 0/7 | 15.7 (7.6) |
| Example 19 | 16 | 7/7 | >31* (9.1) |
|  | 8 | 7/7 | >31* (9.1) |
|  | 4 | 7/7 | >31* (9.1) |
|  | 2 | 6/7 | >7 (9.1) |
|  | 1 | 2/7 | >19.6 (9.1) |
| Example 22 | 64 | 7/7 | >31* (8.1) |
|  | 32 | 7/7 | >31* (8.1) |
|  | 16 | 7/7 | >31* (8.1) |
|  | 8 | 7/7 | >31* (8.1) |
|  | 4 | 6/7 | >24 (8.1) |
|  | 2 | 2/7 | >16.8 (8.1) |
| Example 23 | 32 | 7/7 | >31* (8.0) |
|  | 16 | 7/7 | >31* (8.0) |
|  | 8 | 7/7 | >31* (8.0) |
|  | 4 | 7/7 | >31* (8.0) |
|  | 2 | 6/7 | >7 (8.0) |
|  | 1 | 3/7 | >15.3 (8.0) |
| Example 24 | 32 | 7/7 | >31* (8.0) |
|  | 16 | 7/7 | >31* (8.0) |
|  | 8 | 6/7 | >16 (8.0) |
|  | 4 | 5/7 | >14.5 (8.0) |
|  | 2 | 3/7 | >17 (8.0) |
| Example 39 | 16 | 7/7 | >31* (11.0) |
|  | 8 | 7/7 | >31* (11.0) |
|  | 4 | 7/7 | >31* (11.0) |
|  | 2 | 1/7 | >23 (11.0) |
| Example 56 | 64 | 6/7 | >20 (10.4) |
|  | 16 | 5/7 | >19.3 (10.4) |
| Chloroquine | 128 | 4/7 | >21.3 (8.6) |
|  | 64 | 2/7 | >18.6 (8.6) |
|  | 16 | 1/7 | >18.8 (8.6) |
|  | 4 | 0/7 | 10.3 (8.6) |

*>31 means all animals survived to the end of the experiment. A > sign in front of a number <31 means some of the animals survived the day 31 day experiment.

As shown, the compounds of the present invention possess potent antimalarial activity and greatly reduced toxicity when administered to mammalian subjects.

What is claimed:
1. A compound of Formula I:

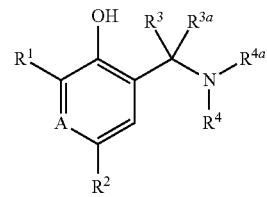

wherein:
$R^1$ is $C_{6-10}$ aryl substituted with 1, 2, or 3 $R^5$;
A is CH;
$R^2$ is $C_{1-10}$ alkyl, $C_{1-10}$ haloalkyl, $C_{1-10}$ alkoxy, $C_{1-10}$ haloalkoxy, $C_{6-10}$ aryl optionally substituted with 1, 2, or 3 $R^5$, heteroaryl optionally substituted with 1, 2, or 3 $R^5$, or arylalkyl optionally substituted with 1, 2, or 3 $R^5$;
$R^3$ and $R^{3a}$ are, independently, hydrogen, $C_{1-10}$ alkyl or $C_{1-10}$ haloalkyl;
$R^4$ and $R^{4a}$ are, independently, hydrogen, $C_{1-10}$ alkyl or $C_{1-10}$ haloalkyl,
or
$R^4$ and $R^{4a}$ together with the nitrogen atom through which they are attached, form a heterocyclic ring of 4 to 7 ring atoms, where one carbon ring atom may be optionally replaced with $NR^6$, O, S, or $SO_2$, and where any carbon ring atom may be optionally substituted with $C_{1-10}$ alkyl, $C_{1-10}$ haloalkyl, $C_{1-10}$ alkoxy, or $C_{1-10}$ haloalkoxy;
each $R^5$ is independently halo, cyano, hydroxy, $C_{1-10}$ alkyl, $C_{1-10}$ haloalkyl, $C_{1-10}$ alkoxy, $C_{1-10}$ haloalkoxy, aryloxy optionally substituted with 1, 2, or 3 $R^7$, amino, $C_{1-10}$ alkylamino, $C_{1-10}$ dialkylamino, $C_{1-10}$ alkylsulfonyl, sulfamoyl, $C_{1-10}$ alkylsulfamoyl or $C_{1-10}$ dialkylsulfamoyl;
or
two adjacent $R^5$ groups taken together equal methylenedioxy;
$R^6$ is $C_{1-10}$ alkyl or $C_{1-10}$ haloalkyl;
$R^7$ is halo, cyano, hydroxy, $C_{1-10}$ alkyl, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylsulfonyl, sulfamoyl, $C_{1-10}$ alkylsulfamoyl or $C_{1-10}$ dialkylsulfamoyl;
provided that when $R^1$ is unsubstituted phenyl, $R^2$ is $C_{6-10}$ aryl substituted with 1, 2, or 3 $R^5$ or heteroaryl optionally substituted with 1, 2, or 3 $R^5$;
or a pharmaceutically acceptable salt, enantiomer, or diastereoisomer thereof;
provided that the compound of Formula I is not:
5-(tert-butyl)-3',4'-dichloro-3-(pyrrolidin-1-ylmethyl)-[1,1'-biphenyl]-2-ol;
5-((3r,5r,7r)-adamantan-1-yl)-4'-chloro-3-((dimethylamino)methyl)-[1,1'-biphenyl]-2-ol;
5-(tert-butyl)-4'-(dimethylamino)-3-((dimethylamino)methyl)-[1,1'-biphenyl]-2-ol;
5-(tert-butyl)-3-((tert-butylamino)methyl)-4'-chloro-[1,1'-biphenyl]-2-ol;
3,3',5,5'-tetrakis((diethylamino)methyl)-[1,1'-biphenyl]-2,2'-diol;
4,4'''-dichloro-5',5''-bis(pyrrolidin-1-ylmethyl)-[1,1':3',1'':3'',1'''-quaterphenyl]-4'',6'-diol;
3,3',5,5'-tetrakis(morpholinomethyl)-[1,1'-biphenyl]-2,2'-diol;

3,3'-bis((diethylamino)methyl)-5,5'-dimethoxy-[1,1'-biphenyl]-2,2'-diol;

or 3-((diethylamino)methyl)-5,5'-dimethoxy-[1,1'-biphenyl]-2,2'-diol;

or a pharmaceutically acceptable salt, enantiomer, or diastereoisomer thereof.

2. The compound according to claim 1 wherein $R^3$ and $R^{3a}$ are H.

3. The compound according to claim 1 wherein $R^4$ is tert-butyl or 1-methylcyclobutyl and $R^{4a}$ is H.

4. The compound according to claim 1 wherein $R^2$ is tert-butyl, $C_{6-10}$ aryl optionally substituted with 1, 2, or 3 $R^5$ or heteroaryl optionally substituted with 1, 2, or 3 $R^5$.

5. The compound according to claim 1 wherein $R^2$ is tert-butyl.

6. The compound according to claim 1 wherein $R^1$ is phenyl substituted with 1, 2, or 3 groups of $R^5$; $R^5$ is halo, cyano, $CF_3$ or $OCF_3$.

7. The compound according to claim 1 wherein:

$R^1$ is phenyl substituted with 1-3 groups of $R^5$;

$R^3$ and $R^{3a}$ are H;

$R^4$ is tert-butyl or 1-methylcyclobutyl and $R^{4a}$ is H; and $R^2$ is tert-butyl, $C_{6-10}$ aryl optionally substituted with 1, 2, or 3 $R^5$ or heteroaryl optionally substituted with 1, 2, or 3 $R^5$.

8. The compound according to claim 1 wherein:

$R^1$ is phenyl substituted with 1, 2, or 3 groups of $R^5$;

$R^3$ and $R^{3a}$ are H;

$R^4$ is tert-butyl and $R^{4a}$ is H; and $R^2$ is tert-butyl.

9. The compound according to claim 1 wherein said compound is:

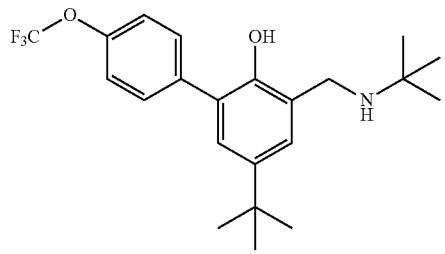 [SMILES: CC(C)(C)NCc1cc(C(C)(C)C)cc(-c2ccc(OC(F)(F)F)cc2)c1O]

5-(tert-butyl)-3-((tert-butylamino)methyl)-4'-(trifluoromethoxy)-[1,1'-biphenyl]-2-ol,

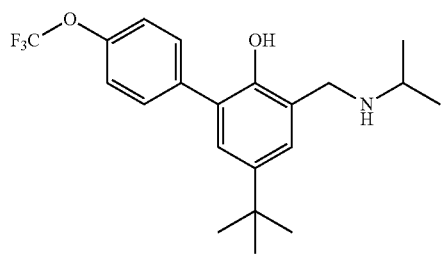 [SMILES: CC(C)NCc1cc(C(C)(C)C)cc(-c2ccc(OC(F)(F)F)cc2)c1O]

5-(tert-butyl)-3-((isopropylamino)methyl)-4'-(trifluoromethoxy)-[1,1'-biphenyl]-2-ol,

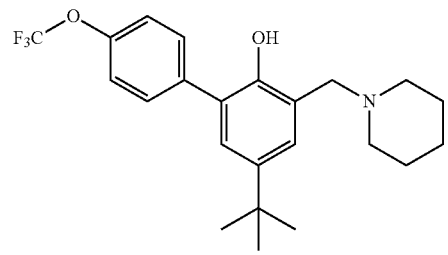 [SMILES: CC(C)(C)c1cc(CN2CCCCC2)c(O)c(-c2ccc(OC(F)(F)F)cc2)c1]

5-(tert-butyl)-3-(piperidin-1-ylmethyl)-4'-(trifluoromethoxy)-[1,1'-biphenyl]-2-ol,

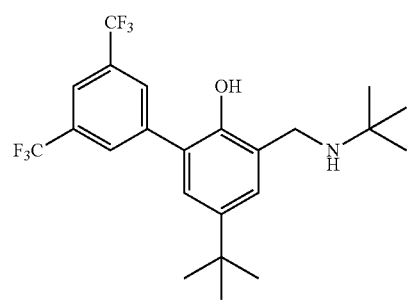 [SMILES: CC(C)(C)NCc1cc(C(C)(C)C)cc(-c2cc(C(F)(F)F)cc(C(F)(F)F)c2)c1O]

5-(tert-butyl)-3-((tert-butylamino)methyl)-3',5'-bis(trifluoromethyl)-[1,1'-biphenyl]-2-ol,

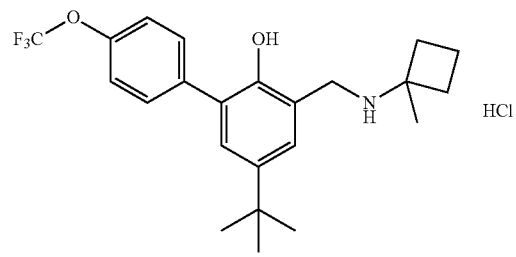 [SMILES: CC1(NCc2cc(C(C)(C)C)cc(-c3ccc(OC(F)(F)F)cc3)c2O)CCC1 ; Cl]

5-(tert-butyl)-3-4(1-methylcyclobutyl)amino)methyl)-4'-(trifluoromethoxy)-[1,1'-biphenyl]-2-ol hydrochloride,

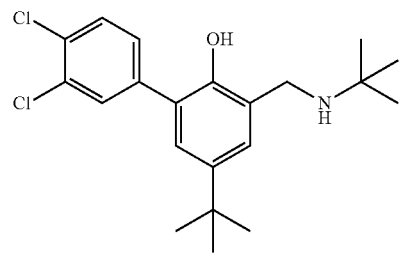 [SMILES: CC(C)(C)NCc1cc(C(C)(C)C)cc(-c2ccc(Cl)c(Cl)c2)c1O]

5-(tert-butyl)-3-((tert-butylamino)methyl)-3',4'-dichloro-[1,1'-biphenyl]-2-ol,

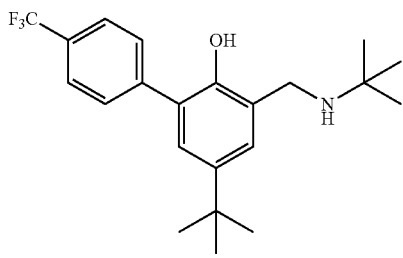 [SMILES: CC(C)(C)NCc1cc(C(C)(C)C)cc(-c2ccc(C(F)(F)F)cc2)c1O]

5-(tert-butyl)-3-((tert-butylamino)methyl)-4'-(trifluoromethyl)-[1,1'-biphenyl]-2-ol,

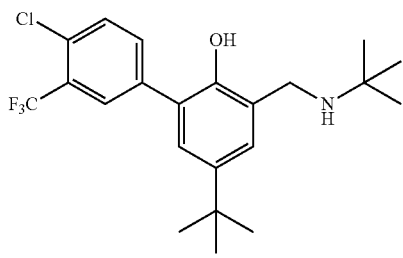 [SMILES: CC(C)(C)NCc1cc(C(C)(C)C)cc(-c2ccc(Cl)c(C(F)(F)F)c2)c1O]

5-(tert-butyl)-3-((tert-butylamino)methyl)-4'-chloro-3'-(trifluoromethyl)-[1,1'-biphenyl]-2-ol,

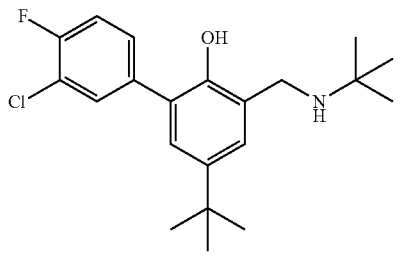

5-(tert-butyl)-3-((tert-butylamino)methyl)-3'-chloro-4'-fluoro-[1,1'-biphenyl]-2-ol,

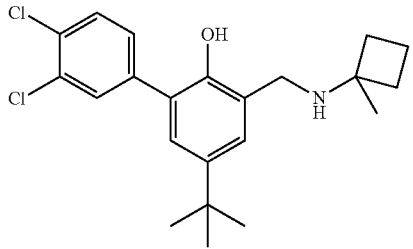 [SMILES: CC1(NCc2cc(C(C)(C)C)cc(-c3ccc(Cl)c(Cl)c3)c2O)CCC1]

5-(tert-butyl)-3',4'-dichloro-3-(((1-methylcyclobutyl)amino)methyl)-[1,1'-biphenyl]-2-ol,

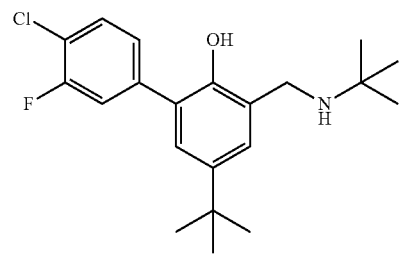

5-(tert-butyl)-3-((tert-butylamino)methyl)-4'-chloro-3'-fluoro-[1,1'-biphenyl]-2-ol,

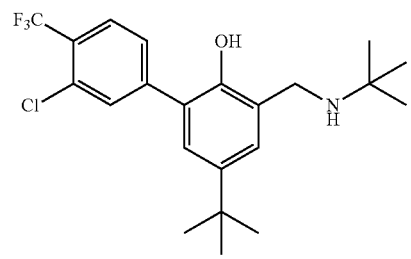 [SMILES: CC(C)(C)NCc1cc(C(C)(C)C)cc(-c2ccc(C(F)(F)F)c(Cl)c2)c1O]

5-(tert-butyl)-3-((tert-butylamino)methyl)-3'-chloro-4'-(trifluoromethyl)-[1,1'-biphenyl]-2-ol,

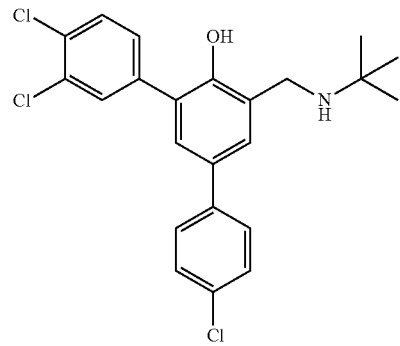

5'-((tert-butylamino)methyl)-3",4,4"-trichloro-[1,1':3',1"-terphenyl]-4'-ol,

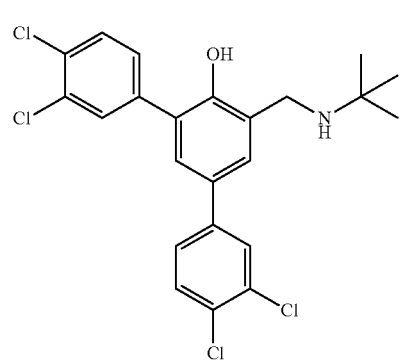 [SMILES: CC(C)(C)NCc1cc(-c2ccc(Cl)c(Cl)c2)cc(-c2ccc(Cl)c(Cl)c2)c1O]

5'-((tert-butylamino)methyl)-3,3",4,4"-tetrachloro-[1,1':3',1"-terphenyl]-4'-ol, or

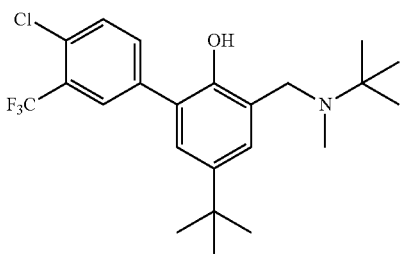 [SMILES: CN(Cc1cc(C(C)(C)C)cc(-c2ccc(Cl)c(C(F)(F)F)c2)c1O)C(C)(C)C]

5-(tert-butyl)-3-((tert-butyl(methyl)amino)methyl)-4'-chloro-3'-(trifluoromethyl)-[1,1'-biphenyl]-2-ol, or a pharmaceutically acceptable salt thereof.

10. The compound according to claim 1 that is a compound of formula IA:

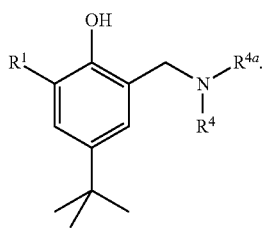

11. The compound according to claim 10, wherein $R^4$ and $R^{4a}$ are, independently, hydrogen or $C_{1-10}$ alkyl or $R^4$ and $R^{4a}$, together with the nitrogen atom through which they are attached, form a heterocyclic ring of 4 to 7 ring atoms.

12. The compound according to claim 10, wherein $R^1$ is unsubstituted naphthyl.

13. The compound according to claim 10, wherein $R^1$ is substituted with 1, 2, or 3 of $R^5$, wherein each $R^5$ is independently —$CF_3$, —$OCF_3$, —$SO_2C_{1-6}$alkyl, F, Cl, Br, —Ophenyl.

14. The compound according to claim 1 that is a compound of formula IB:

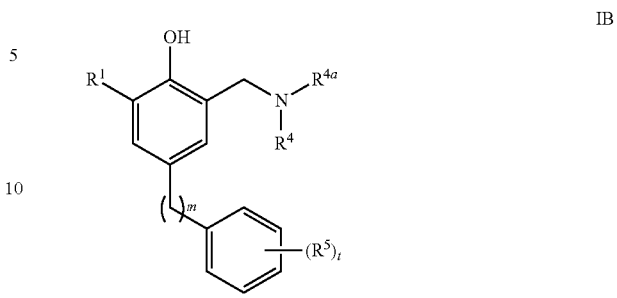

wherein m is from 0 to 4 and t is from 0 to 3.

15. The compound according to claim 14, wherein m is 0.

16. The compound according to claim 14, wherein m is from 1 to 4.

17. The compound according to claim 14, wherein $R^4$ and $R^{4a}$ are, independently, hydrogen or $C_{1-10}$ alkyl or $R^4$ and $R^{4a}$, together with the nitrogen atom through which they are attached, form a heterocyclic ring of 4 to 7 ring atoms.

18. The compound according to claim 14, wherein t is 0.

19. The compound according to claim 14, wherein t is from 1 to 3.

20. The compound according to claim 19, wherein each $R^5$ is independently —$CF_3$, —$OCF_3$, —$SO_2C_{1-6}$alkyl, F, Cl, Br, or —Ophenyl.

21. The compound according to claim 1 wherein $R^2$ is pyridyl optionally substituted with 1, 2, or 3 $R^5$.

22. The compound according to claim 1, wherein $R^2$ is benzofuranyl optionally substituted with 1, 2, or 3 $R^5$.

23. The compound according to claim 1, wherein $R^2$ is —$OCF_3$ or —Oalkaryl.

24. A pharmaceutical composition comprising a compound according to claim 1 and a pharmaceutically acceptable carrier or diluent.

25. A method of treating malaria in a patient comprising administering to the patient a compound according to claim 1.

26. The method according to claim 25 wherein the compound of Formula I is co-administered with at least one other anti-malarial agent that is Amodiaquine, Arteether, Arteflene, Artemether, Artemisinin, Artesunate, Atovaquone, Chloroquine, Clindamycin, Dihydroartemisinin, Doxycycline, Halofantrine, Lumefantrine, Mefloquine, Pamaquine, Piperaquine, Primaquine, Proguanil, Pyrimethamine, Pyronaridine, Quinine, Tafenoquine, or a combination thereof.

* * * * *